United States Patent
Iriyama et al.

(10) Patent No.: US 11,530,409 B2
(45) Date of Patent: Dec. 20, 2022

(54) SINGLE-STRANDED OLIGONUCLEOTIDE

(71) Applicant: NISSAN CHEMICAL CORPORATION, Tokyo (JP)

(72) Inventors: Yusuke Iriyama, Funabashi (JP); Hiroyuki Nakajima, Shiraoka (JP); Tatsuro Kanaki, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 25 days.

(21) Appl. No.: 16/073,114

(22) PCT Filed: Jan. 26, 2017

(86) PCT No.: PCT/JP2017/002831
§ 371 (c)(1),
(2) Date: Dec. 14, 2018

(87) PCT Pub. No.: WO2017/131124
PCT Pub. Date: Aug. 3, 2017

(65) Prior Publication Data
US 2019/0119683 A1 Apr. 25, 2019

(30) Foreign Application Priority Data

Jan. 26, 2016 (JP) .............................. JP2016-012804
Aug. 12, 2016 (JP) .............................. JP2016-158833

(51) Int. Cl.
| C07H 21/04 | (2006.01) |
| C12N 15/113 | (2010.01) |
| A61K 48/00 | (2006.01) |
| A61K 31/7088 | (2006.01) |
| C12P 19/34 | (2006.01) |

(52) U.S. Cl.
CPC ...... *C12N 15/1137* (2013.01); *A61K 31/7088* (2013.01); *A61K 48/00* (2013.01); *C12N 15/113* (2013.01); *C12P 19/34* (2013.01); *C12N 2310/11* (2013.01); *C12N 2310/315* (2013.01); *C12N 2310/32* (2013.01); *C12N 2310/351* (2013.01); *C12N 2310/3513* (2013.01); *C12N 2310/3515* (2013.01)

(58) Field of Classification Search
None
See application file for complete search history.

(56) References Cited

U.S. PATENT DOCUMENTS

| 6,268,490 B1 | 7/2001 | Imanishi et al. |
| 2003/0105309 A1 | 6/2003 | Imanishi et al. |
| 2006/0166908 A1 | 7/2006 | Imanishi et al. |
| 2007/0032441 A1* | 2/2007 | McSwiggen .......... C12N 15/111 514/44 A |
| 2007/0167387 A1 | 7/2007 | Imanishi et al. |
| 2011/0223665 A1 | 9/2011 | Maier et al. |
| 2011/0251261 A1 | 10/2011 | Burnett et al. |
| 2012/0010271 A1 | 1/2012 | Ohgi et al. |
| 2012/0208991 A1 | 8/2012 | Obika et al. |
| 2013/0131147 A1 | 5/2013 | Seth et al. |
| 2014/0302603 A1 | 10/2014 | Yokota et al. |
| 2014/0329886 A1 | 11/2014 | Ohgi et al. |
| 2014/0343123 A1 | 11/2014 | Prakash et al. |
| 2015/0247141 A1 | 9/2015 | Uhlmann et al. |
| 2015/0299695 A1 | 10/2015 | Uhlmann et al. |
| 2015/0315585 A1 | 11/2015 | Uhlmann et al. |
| 2015/0315586 A1 | 11/2015 | Uhlmann et al. |
| 2015/0315587 A1 | 11/2015 | Uhlmann et al. |
| 2015/0315588 A1 | 11/2015 | Uhlmann et al. |
| 2016/0145614 A1 | 5/2016 | Yokota et al. |
| 2017/0349896 A1 | 12/2017 | Albaek et al. |
| 2018/0073024 A1 | 3/2018 | Yokota et al. |
| 2018/0320181 A1 | 11/2018 | Yokota et al. |
| 2021/0254055 A1 | 8/2021 | Iriyama et al. |

FOREIGN PATENT DOCUMENTS

| EP | 1115859 A2 | 3/2000 |
| EP | 3088525 A1 | 11/2016 |
| JP | H08-154687 A | 6/1996 |

(Continued)

OTHER PUBLICATIONS

Behlke et al. Integrated DNA Technologies 2005 at p. 8.*
Cowsert, Lex M., et al. "In vitro evaluation of phosphorothioate oligonucleotides targeted to the E2 mRNA of papillomavirus: potential treatment for genital warts." Antimicrobial agents and chemotherapy 37.2 (1993): 171-177.*
Nishina et al., "DNA/RNA heteroduplex oligonucleotide for highly efficient gene silencing," *Nat. Commun.*, 6: 7969 (2015).
Subramanian et al., "Enhancing antisense efficacy with multimers and multi-targeting oligonucleotides (MTOs) using cleavable linkers," *Nucleic Acids Res.*, 43(19): 9123-9132 (2015).
Japanese Patent Office, International Search Report in International Patent Application No. PCT/JP2017/002831 (dated Apr. 11, 2017).

(Continued)

*Primary Examiner* — Kimberly Chong
(74) *Attorney, Agent, or Firm* — Leydig, Voit & Mayer, Ltd.

(57) ABSTRACT

Provided is a single-stranded oligonucleotide that is capable of controlling a target gene with high efficiency and can be easily produced. The single-stranded oligonucleotide is represented by the formula X-L-Y wherein X and Y hybridize by a first nucleotide sequence portion and a second nucleotide sequence portion. X is composed of 7 to 100 nucleotides, contains at least one modified nucleotide, and has a first nucleotide sequence that is capable of hybridizing with a second oligonucleotide and contains at least four contiguous nucleotides recognized by RNase H. Y is composed of 4 to 100 nucleotides, and has a second nucleotide sequence that is capable of hybridizing with a second oligonucleotide and contains at least one ribonucleotide. At least one of nucleotide sequence X and nucleotide sequence Y has an antisense sequence capable of hybridizing with a target RNA. L is a group derived from a third oligonucleotide that is degraded under physiological conditions.

45 Claims, 11 Drawing Sheets

Specification includes a Sequence Listing.

(56) References Cited

FOREIGN PATENT DOCUMENTS

| | | |
|---|---|---|
| JP | H09-110894 A | 4/1997 |
| JP | H11-137260 A | 5/1999 |
| JP | 2002-526072 A | 8/2002 |
| JP | 2007-525192 A | 9/2007 |
| JP | 2011-528910 A | 12/2011 |
| JP | 2014-527819 A | 10/2014 |
| JP | 2015-502134 A | 1/2015 |
| JP | 2015-529469 A | 10/2015 |
| WO | WO 1998/039352 A1 | 9/1998 |
| WO | WO 2003/068795 A1 | 8/2003 |
| WO | WO 2003/070917 A2 | 8/2003 |
| WO | WO 2004/015075 A2 | 2/2004 |
| WO | WO 2004/015107 A2 | 2/2004 |
| WO | WO 2004/061081 A2 | 7/2004 |
| WO | WO 2005/001055 A2 | 1/2005 |
| WO | WO 2005/019453 A2 | 3/2005 |
| WO | WO 2005/021570 A1 | 3/2005 |
| WO | WO 2011/008730 A2 | 1/2011 |
| WO | WO 2011/052436 A1 | 5/2011 |
| WO | WO 2011/156202 A1 | 12/2011 |
| WO | WO 2012/017919 A1 | 2/2012 |
| WO | WO 2013/089283 A1 | 6/2013 |
| WO | WO 2013/103146 A1 | 7/2013 |
| WO | WO 2014/179620 A1 | 11/2014 |
| WO | WO 2014/192310 A1 | 12/2014 |
| WO | WO 2015/105083 A1 | 7/2015 |
| WO | WO 2015/113922 A1 | 8/2015 |
| WO | WO 2016/152352 A1 | 9/2016 |
| WO | WO 2017/131124 A1 | 8/2017 |

OTHER PUBLICATIONS

Anderson et al., "Bispecific Short Hairpin siRNA Constructs Targeted to CD4, CXCR4, and CCR5 Confer HIV-1 Resistance," *Oligonucleotides*, 13(5): 303-312 (2003).

Seyhan et al., "RNA Interference from Multimeric shRNAs Generated by Rolling Circle Transcription," *Oligonucleotides*, 16(4): 353-363 (2006).

European Patent Office, Extended European Search Report in European Patent Application No. 17744354.6 (dated Jun. 5, 2019).

Japanese Patent Office, International Search Report in International Patent Application No. PCT/JP2018/004052 (dated May 1, 2018).

Hamazaki et al., "Inhibition of Influenza Virus Replication in MDCK Cells by Circular Dumbbell RNA/DNA Chimeras with Closed Alkyl Loop Structures," *Helvetica Chimica Acta*, 85(7): 2183-2194 (2002).

Park et al., "Inhibition of HIV-1 Replication by a New Type of Circular Dumbbell RNA/DNA Chimeric Oligonucleotides," *Biochem. Biophys. Res. Commun.*, 270(3): 953-960 (2000).

Masuda et al., "Synthesis, gene-silencing activity and nuclease resistance of 3'-3'-linked double short hairpin RNA," *Bioorg. Med. Chem.*, 18(23): 8277-8283 (2010).

European Patent Office, Extended European Search Report in European Patent Application No. 18748481.1 (dated Mar. 15, 2021).

U.S. Appl. No. 16/484,064, filed Aug. 6, 2019.

European Patent Office, Communication Pursuant to Article 94(3) EPC in European Patent Application No. 18748481.1 (dated Feb. 22, 2022).

* cited by examiner

| Lane | No. |
|---|---|
| 1 | ss-DNA size marker (15mer, 20mer, 30mer, 40mer, 60mer, 80mer) |
| 2 | Example No. 4 (before) |
| 3 | Example No. 4 (after) |
| 4 | ds-RNA size marker (17bp, 21bp, 25bp, 29bp) |

Lane No.

1   ss-DNA size marker (15mer, 20mer, 30mer, 40mer, 60mer, 80mer)

2   Example No. 5 (before)

3   Example No. 5 (after)

4   ds-RNA size marker (17bp, 21bp, 25bp, 29bp)

SEQUENCE LISTING

```
<160> NUMBER OF SEQ ID NOS: 37

<210> SEQ ID NO 1
<211> LENGTH: 32
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (15)..(30)
<223> OTHER INFORMATION: ribonucleoside
<220> FEATURE:
<221> NAME/KEY: modified_base
<222> LOCATION: (30)..(32)
<223> OTHER INFORMATION: Phosphorothioate bond between nucleic acids
<220> FEATURE:
<221> NAME/KEY: modified_base
<222> LOCATION: (31)..(31)
<223> OTHER INFORMATION: 2'-O-methyladenosine
<220> FEATURE:
<221> NAME/KEY: modified_base
<222> LOCATION: (32)..(32)
<223> OTHER INFORMATION: gm

<400> SEQUENCE: 1
cttagcactg gcctaaaaag gccagugcua ag                              32

<210> SEQ ID NO 2
<211> LENGTH: 32
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
```

```
<223> OTHER INFORMATION: Phosphorothioate bond between nucleic acids
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(18)
<223> OTHER INFORMATION: ribonucleoside
<220> FEATURE:
<221> NAME/KEY: modified_base
<222> LOCATION: (19)..(32)
<223> OTHER INFORMATION: Phosphorothioate bond between nucleic acids
<220> FEATURE:
<221> NAME/KEY: modified_base
<222> LOCATION: (19)..(20)
<223> OTHER INFORMATION: LNA
<220> FEATURE:
<221> NAME/KEY: modified_base
<222> LOCATION: (19)..(19)
<223> OTHER INFORMATION: m5c
<220> FEATURE:
<221> NAME/KEY: modified_base
<222> LOCATION: (31)..(32)
<223> OTHER INFORMATION: LNA
<220> FEATURE:
<221> NAME/KEY: modified_base
<222> LOCATION: (31)..(31)
<223> OTHER INFORMATION: m5c

<400> SEQUENCE: 2
aggccagugc uaagaaaact tagcactggc ct                                    32

<210> SEQ ID NO 3
<211> LENGTH: 30
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(3)
<223> OTHER INFORMATION: gm
<220> FEATURE:
<221> NAME/KEY: modified_base
<222> LOCATION: (4)..(17)
<223> OTHER INFORMATION: ribonucleoside
<220> FEATURE:
<221> NAME/KEY: modified_base
<222> LOCATION: (18)..(30)
<223> OTHER INFORMATION: Phosphorothioate bond between nucleic acids
<220> FEATURE:
<221> NAME/KEY: modified_base
<222> LOCATION: (18)..(19)
<223> OTHER INFORMATION: LNA
<220> FEATURE:
<221> NAME/KEY: modified_base
<222> LOCATION: (28)..(30)
<223> OTHER INFORMATION: LNA
<220> FEATURE:
<221> NAME/KEY: modified_base
<222> LOCATION: (28)..(29)
<223> OTHER INFORMATION: m5c
```

```
<400> SEQUENCE: 3
aggccagugc uaaaaaatta gcactggcct                                              30

<210> SEQ ID NO 4
<211> LENGTH: 14
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (13)..(13)
<223> OTHER INFORMATION: m5c

<400> SEQUENCE: 4
cttagcactg gcct                                                               14

<210> SEQ ID NO 5
<211> LENGTH: 14
<212> TYPE: RNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(3)
<223> OTHER INFORMATION: Phosphorothioate bond between nucleic acids
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (12)..(14)
<223> OTHER INFORMATION: Phosphorothioate bond between nucleic acids
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: gm

<400> SEQUENCE: 5
aggccagugc uaag                                                               14

<210> SEQ ID NO 6
<211> LENGTH: 13
<212> TYPE: DNA
<213> ORGANISM: Artificial Sequence
```

```
<220> FEATURE:
<223> OTHER INFORMATION: Artificially synthesized oligonucleotide
      sequence
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (11)..(12)
<223> OTHER INFORMATION: m5c

<400> SEQUENCE: 6
ttagcactgg cct                                                          13

<210> SEQ ID NO 7
<211> LENGTH: 13
<212> TYPE: RNA
<213> ORGANISM: Artificial Sequence
<220> FEATURE:
<223> OTHER INFORMATION: Artificially synthesized oligonucloetide
      sequence
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(3)
<223> OTHER INFORMATION: gm
<220> FEATURE:
<221> NAME/KEY: modified_base
<222> LOCATION: (11)..(13)
<223> OTHER INFORMATION: Phosphorothioate bond between nucleic acids
<220> FEATURE:
<221> NAME/KEY: modified_base
<222> LOCATION: (12)..(13)
<223> OTHER INFORMATION: 2'-O-methyladenosine

<400> SEQUENCE: 7
aggccagugc uaa                                                          13

<210> SEQ ID NO 8
<211> LENGTH: 14
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(1)
<223> OTHER INFORMATION: m5c
<220> FEATURE:
<221> NAME/KEY: modified_base
```

```
-continued

<222> LOCATION: (13)..(14)
<223> OTHER INFORMATION: LNA
<220> FEATURE:
<221> NAME/KEY: modified_base
<222> LOCATION: (13)..(13)
<223> OTHER INFORMATION: m5c

<400> SEQUENCE: 8
cttagcactg gcct                                                     14

<210> SEQ ID NO 9
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (11)..(12)
<223> OTHER INFORMATION: m5c

<400> SEQUENCE: 9
ttagcactgg cct                                                      13

<210> SEQ ID NO 10
<211> LENGTH: 44
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (14)..(30)
<223> OTHER INFORMATION: ribonucleoside
<220> FEATURE:
<221> NAME/KEY: modified_base
<222> LOCATION: (31)..(44)
<223> OTHER INFORMATION: Phosphorothioate bond between nucleic acids
<220> FEATURE:
<221> NAME/KEY: modified_base
<222> LOCATION: (31)..(32)
```

<223> OTHER INFORMATION: LNA
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (43)..(44)
<223> OTHER INFORMATION: LNA
<220> FEATURE:
<221> NAME/KEY: modified_base
<222> LOCATION: (43)..(43)
<223> OTHER INFORMATION: m5c

<400> SEQUENCE: 10
gcattggtat tcaaaaauga auaccaaugc cttagcactg gcct                    44

<210> SEQ ID NO 11
<211> LENGTH: 44
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(31)
<223> OTHER INFORMATION: ribonucleoside
<220> FEATURE:
<221> NAME/KEY: modified_base
<222> LOCATION: (32)..(33)
<223> OTHER INFORMATION: LNA
<220> FEATURE:
<221> NAME/KEY: modified_base
<222> LOCATION: (32)..(44)
<223> OTHER INFORMATION: Phosphorothioate bond between nucleic acids
<220> FEATURE:
<221> NAME/KEY: modified_base
<222> LOCATION: (33)..(33)
<223> OTHER INFORMATION: m5c
<220> FEATURE:
<221> NAME/KEY: modified_base
<222> LOCATION: (42)..(44)
<223> OTHER INFORMATION: LNA
<220> FEATURE:
<221> NAME/KEY: modified_base
<222> LOCATION: (43)..(43)
<223> OTHER INFORMATION: m5c

<400> SEQUENCE: 11
cttagcactg gcctugaaua ccaaugcaaa agcattggta ttca                    44

<210> SEQ ID NO 12
<211> LENGTH: 27
<212> TYPE: DNA

```
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(13)
<223> OTHER INFORMATION: ribonucleoside
<220> FEATURE:
<221> NAME/KEY: modified_base
<222> LOCATION: (14)..(14)
<223> OTHER INFORMATION: m5c
<220> FEATURE:
<221> NAME/KEY: modified_base
<222> LOCATION: (14)..(15)
<223> OTHER INFORMATION: LNA
<220> FEATURE:
<221> NAME/KEY: modified_base
<222> LOCATION: (14)..(27)
<223> OTHER INFORMATION: Phosphorothioate bond between nucleic acids
<220> FEATURE:
<221> NAME/KEY: modified_base
<222> LOCATION: (26)..(26)
<223> OTHER INFORMATION: m5c
<220> FEATURE:
<221> NAME/KEY: modified_base
<222> LOCATION: (26)..(27)
<223> OTHER INFORMATION: LNA

<400> SEQUENCE: 12
ugaauaccaa ugccuuagca ctggcct                                          27

<210> SEQ ID NO 13
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorotihioate bond between nucleotide
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c

<400> SEQUENCE: 13
```
gcattggtat tca                                                            13

<210> SEQ ID NO 14
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c

<400> SEQUENCE: 14
gcattggtat tca                                                            13

<210> SEQ ID NO 15
<211> LENGTH: 68
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(36)
<223> OTHER INFORMATION: ribonucleoside
<220> FEATURE:
<221> NAME/KEY: modified_base
<222> LOCATION: (37)..(37)
<223> OTHER INFORMATION: m5c
<220> FEATURE:
<221> NAME/KEY: modified_base
<222> LOCATION: (37)..(38)
<223> OTHER INFORMATION: LNA
<220> FEATURE:
<221> NAME/KEY: modified_base
<222> LOCATION: (37)..(50)
<223> OTHER INFORMATION: Phosphorothioate bond between nucleic acids
<220> FEATURE:
<221> NAME/KEY: modified_base
<222> LOCATION: (49)..(49)
<223> OTHER INFORMATION: m5c
<220> FEATURE:
<221> NAME/KEY: modified_base
<222> LOCATION: (49)..(50)

```
<223> OTHER INFORMATION: LNA
<220> FEATURE:
<221> NAME/KEY: modified_base
<222> LOCATION: (51)..(54)
<223> OTHER INFORMATION: ribonucleoside
<220> FEATURE:
<221> NAME/KEY: modified_base
<222> LOCATION: (55)..(55)
<223> OTHER INFORMATION: m5c
<220> FEATURE:
<221> NAME/KEY: modified_base
<222> LOCATION: (55)..(56)
<223> OTHER INFORMATION: LNA
<220> FEATURE:
<221> NAME/KEY: modified_base
<222> LOCATION: (55)..(68)
<223> OTHER INFORMATION: Phosphorothioate bond between nucleic acids
<220> FEATURE:
<221> NAME/KEY: modified_base
<222> LOCATION: (67)..(67)
<223> OTHER INFORMATION: m5c
<220> FEATURE:
<221> NAME/KEY: modified_base
<222> LOCATION: (67)..(68)
<223> OTHER INFORMATION: LNA

<400> SEQUENCE: 15
aggccagugc uaaguuuuag gccagugcua agaaaactta gcactggcct aaaacttagc    60
actggcct                                                            68

<210> SEQ ID NO 16
<211> LENGTH: 66
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(17)
<223> OTHER INFORMATION: ribonucleoside
<220> FEATURE:
<221> NAME/KEY: modified_base
<222> LOCATION: (18)..(18)
<223> OTHER INFORMATION: m5c
<220> FEATURE:
<221> NAME/KEY: modified_base
<222> LOCATION: (18)..(19)
<223> OTHER INFORMATION: LNA
<220> FEATURE:
<221> NAME/KEY: modified_base
<222> LOCATION: (18)..(31)
<223> OTHER INFORMATION: Phosphorothioate bond between nucleic acids
<220> FEATURE:
<221> NAME/KEY: modified_base
<222> LOCATION: (30)..(30)
<223> OTHER INFORMATION: m5c
<220> FEATURE:
<221> NAME/KEY: modified_base
<222> LOCATION: (30)..(31)
```

<223> OTHER INFORMATION: LNA
<220> FEATURE:
<221> NAME/KEY: modified_base
<222> LOCATION: (32)..(53)
<223> OTHER INFORMATION: ribonucleoside
<220> FEATURE:
<221> NAME/KEY: modified_base
<222> LOCATION: (54)..(55)
<223> OTHER INFORMATION: LNA
<220> FEATURE:
<221> NAME/KEY: modified_base
<222> LOCATION: (54)..(66)
<223> OTHER INFORMATION: Phosphorothioate bond between nucleic acids
<220> FEATURE:
<221> NAME/KEY: modified_base
<222> LOCATION: (55)..(55)
<223> OTHER INFORMATION: m5c
<220> FEATURE:
<221> NAME/KEY: modified_base
<222> LOCATION: (64)..(66)
<223> OTHER INFORMATION: LNA
<220> FEATURE:
<221> NAME/KEY: modified_base
<222> LOCATION: (65)..(65)
<223> OTHER INFORMATION: m5c

<400> SEQUENCE: 16
ugaauaccaa ugcaaaactt agcactggcc taaaaaggcc agugcuaagu uuugcauugg    60
tattca                                                               66

<210> SEQ ID NO 17
<211> LENGTH: 66
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(35)
<223> OTHER INFORMATION: ribonucleoside
<220> FEATURE:
<221> NAME/KEY: modified_base
<222> LOCATION: (36)..(36)
<223> OTHER INFORMATION: m5c
<220> FEATURE:
<221> NAME/KEY: modified_base
<222> LOCATION: (36)..(37)
<223> OTHER INFORMATION: LNA
<220> FEATURE:
<221> NAME/KEY: modified_base
<222> LOCATION: (36)..(49)
<223> OTHER INFORMATION: Phosphorothioate bond between nucleic acids
<220> FEATURE:
<221> NAME/KEY: modified_base
<222> LOCATION: (48)..(48)
<223> OTHER INFORMATION: m5c
<220> FEATURE:
<221> NAME/KEY: modified_base
<222> LOCATION: (48)..(49)

<223> OTHER INFORMATION: LNA
<220> FEATURE:
<221> NAME/KEY: modified_base
<222> LOCATION: (50)..(53)
<223> OTHER INFORMATION: ribonucleoside
<220> FEATURE:
<221> NAME/KEY: modified_base
<222> LOCATION: (54)..(55)
<223> OTHER INFORMATION: LNA
<220> FEATURE:
<221> NAME/KEY: modified_base
<222> LOCATION: (54)..(66)
<223> OTHER INFORMATION: Phosphorothioate bond between nucleic acids
<220> FEATURE:
<221> NAME/KEY: modified_base
<222> LOCATION: (55)..(55)
<223> OTHER INFORMATION: m5c
<220> FEATURE:
<221> NAME/KEY: modified_base
<222> LOCATION: (64)..(66)
<223> OTHER INFORMATION: LNA
<220> FEATURE:
<221> NAME/KEY: modified_base
<222> LOCATION: (65)..(65)
<223> OTHER INFORMATION: m5c

<400> SEQUENCE: 17
ugaauaccaa ugcuuuuagg ccagugcuaa gaaaacuuag cacuggccua aaagcauugg    60
tattca                                                              66

<210> SEQ ID NO 18
<211> LENGTH: 42
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (1)..(12)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (13)..(28)
<223> OTHER INFORMATION: ribonucleoside
<220> FEATURE:
<221> NAME/KEY: modified_base
<222> LOCATION: (29)..(29)
<223> OTHER INFORMATION: m5c
<220> FEATURE:
<221> NAME/KEY: modified_base
<222> LOCATION: (29)..(30)
<223> OTHER INFORMATION: LNA
<220> FEATURE:
<221> NAME/KEY: modified_base
<222> LOCATION: (29)..(42)
<223> OTHER INFORMATION: Phosphorothioate bond between nucleic acids
<220> FEATURE:
<221> NAME/KEY: modified_base
<222> LOCATION: (41)..(41)
<223> OTHER INFORMATION: m5c
<220> FEATURE:
<221> NAME/KEY: modified_base
<222> LOCATION: (41)..(42)
<223> OTHER INFORMATION: LNA

<400> SEQUENCE: 18
cuattactat gtaaaaacau aguaauagct tagcactggc ct                    42

<210> SEQ ID NO 19
<211> LENGTH: 42
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (15)..(30)
<223> OTHER INFORMATION: ribonucleoside
<220> FEATURE:
<221> NAME/KEY: modified_base
<222> LOCATION: (31)..(42)
<223> OTHER INFORMATION: Phosphorothioate bond between nucleic acids
<220> FEATURE:
<221> NAME/KEY: modified_base
<222> LOCATION: (41)..(41)
<223> OTHER INFORMATION: gm
<220> FEATURE:
<221> NAME/KEY: modified_base
<222> LOCATION: (42)..(42)
<223> OTHER INFORMATION: um

<400> SEQUENCE: 19
cttagcactg gcctacauag uaaugaaaaa tcattactat gu                    42

<210> SEQ ID NO 20
<211> LENGTH: 26
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(12)
<223> OTHER INFORMATION: ribonucleoside
<220> FEATURE:
<221> NAME/KEY: modified_base
<222> LOCATION: (13)..(13)
<223> OTHER INFORMATION: m5c

```
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (13)..(26)
<223> OTHER INFORMATION: Phosphorothioate bond between nucleic acids
<220> FEATURE:
<221> NAME/KEY: modified_base
<222> LOCATION: (25)..(25)
<223> OTHER INFORMATION: m5c
<220> FEATURE:
<221> NAME/KEY: modified_base
<222> LOCATION: (25)..(26)
<223> OTHER INFORMATION: LNA

<400> SEQUENCE: 20
acauaguaau agcttagcac tggcct                                           26

<210> SEQ ID NO 21
<211> LENGTH: 12
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (1)..(12)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: um

<400> SEQUENCE: 21
cuattactat gu                                                          12

<210> SEQ ID NO 22
<211> LENGTH: 26
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (13)..(13)
<223> OTHER INFORMATION: m5c
<220> FEATURE:
```

```
<221> NAME/KEY: modified_base
<222> LOCATION: (13)..(14)
<223> OTHER INFORMATION: LNA
<220> FEATURE:
<221> NAME/KEY: modified_base
<222> LOCATION: (15)..(24)
<223> OTHER INFORMATION: ribonucleoside
<220> FEATURE:
<221> NAME/KEY: modified_base
<222> LOCATION: (24)..(26)
<223> OTHER INFORMATION: Phosphorothioate bond between nucleic acids
<220> FEATURE:
<221> NAME/KEY: modified_base
<222> LOCATION: (25)..(25)
<223> OTHER INFORMATION: gm
<220> FEATURE:
<221> NAME/KEY: modified_base
<222> LOCATION: (25)..(26)
<223> OTHER INFORMATION: LNA
<220> FEATURE:
<221> NAME/KEY: modified_base
<222> LOCATION: (26)..(26)
<223> OTHER INFORMATION: 2'-O-methyladenosine

<400> SEQUENCE: 22
cttagcactg gcctacauag uaauga                                           26

<210> SEQ ID NO 23
<211> LENGTH: 12
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(12)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: um

<400> SEQUENCE: 23
ucattactat gu                                                          12

<210> SEQ ID NO 24
<211> LENGTH: 45
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
```

```
<222> LOCATION: (1)..(14)
<223> OTHER INFORMATION: phosphorothioate bond between nucleic acids
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (15)..(32)
<223> OTHER INFORMATION: ribonucleoside
<220> FEATURE:
<221> NAME/KEY: modified_base
<222> LOCATION: (33)..(34)
<223> OTHER INFORMATION: LNA
<220> FEATURE:
<221> NAME/KEY: modified_base
<222> LOCATION: (33)..(45)
<223> OTHER INFORMATION: Phosphorothioate bond between nucleic acids
<220> FEATURE:
<221> NAME/KEY: modified_base
<222> LOCATION: (34)..(34)
<223> OTHER INFORMATION: m5c
<220> FEATURE:
<221> NAME/KEY: modified_base
<222> LOCATION: (43)..(45)
<223> OTHER INFORMATION: LNA
<220> FEATURE:
<221> NAME/KEY: modified_base
<222> LOCATION: (44)..(44)
<223> OTHER INFORMATION: m5c

<400> SEQUENCE: 24
cttagcactg gcctaaaaag gccagugcua aggcattggt attca                45

<210> SEQ ID NO 25
<211> LENGTH: 27
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(27)
<223> OTHER INFORMATION: Phosphorothioate bond between nucleic acids
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (25)..(27)
<223> OTHER INFORMATION: LNA
```

```
<220> FEATURE:
<221> NAME/KEY: modified_base
<222> LOCATION: (26)..(26)
<223> OTHER INFORMATION: m5c

<400> SEQUENCE: 25
aggccagugc uaaggcattg gtattca                                              27

<210> SEQ ID NO 26
<211> LENGTH: 14
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA

<400> SEQUENCE: 26
cttagcactg gcct                                                            14

<210> SEQ ID NO 27
<211> LENGTH: 42
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: Phosphorothioate bond between nucleic acids
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (17)..(26)
<223> OTHER INFORMATION: Phosphorothioate bond between nucleic acids
<220> FEATURE:
<221> NAME/KEY: modified_base
<222> LOCATION: (27)..(40)
<223> OTHER INFORMATION: ribonucleoside
<220> FEATURE:
```

```
<221> NAME/KEY: modified_base
<222> LOCATION: (40)..(42)
<223> OTHER INFORMATION: Phosphorothioate bond between nucleic acids
<220> FEATURE:
<221> NAME/KEY: modified_base
<222> LOCATION: (41)..(41)
<223> OTHER INFORMATION: 2'-O-methyladenosine
<220> FEATURE:
<221> NAME/KEY: modified_base
<222> LOCATION: (42)..(42)
<223> OTHER INFORMATION: gm

<400> SEQUENCE: 27
cttagcactg gcctctatta ctatgtaaaa acauaguaau ag                          42

<210> SEQ ID NO 28
<211> LENGTH: 42
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (1)..(8)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (8)..(16)
<223> OTHER INFORMATION: ribonucleoside
<220> FEATURE:
<221> NAME/KEY: modified_base
<222> LOCATION: (17)..(22)
<223> OTHER INFORMATION: Phosphorothioate bond between nucleic acids
<220> FEATURE:
<221> NAME/KEY: modified_base
<222> LOCATION: (22)..(28)
<223> OTHER INFORMATION: ribonucleoside
<220> FEATURE:
<221> NAME/KEY: modified_base
<222> LOCATION: (29)..(29)
<223> OTHER INFORMATION: m5c
<220> FEATURE:
<221> NAME/KEY: modified_base
<222> LOCATION: (29)..(30)
<223> OTHER INFORMATION: LNA
<220> FEATURE:
<221> NAME/KEY: modified_base
<222> LOCATION: (29)..(42)
<223> OTHER INFORMATION: Phosphorothioate bond between nucleic acids
<220> FEATURE:
<221> NAME/KEY: modified_base
<222> LOCATION: (41)..(41)
<223> OTHER INFORMATION: m5c
<220> FEATURE:
<221> NAME/KEY: modified_base
<222> LOCATION: (41)..(42)
<223> OTHER INFORMATION: LNA

<400> SEQUENCE: 28
cuattacuau guaaaaacat aguaauagct tagcactggc ct                          42

<210> SEQ ID NO 29
<211> LENGTH: 30
<212> TYPE: DNA
<213> ORGANISM: Artificial Sequence
<220> FEATURE:
```

```
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(17)
<223> OTHER INFORMATION: ribonucleoside
<220> FEATURE:
<221> NAME/KEY: modified_base
<222> LOCATION: (18)..(19)
<223> OTHER INFORMATION: LNA
<220> FEATURE:
<221> NAME/KEY: modified_base
<222> LOCATION: (18)..(30)
<223> OTHER INFORMATION: Phosphorothioate bond between nucleic acids
<220> FEATURE:
<221> NAME/KEY: modified_base
<222> LOCATION: (28)..(30)
<223> OTHER INFORMATION: LNA
<220> FEATURE:
<221> NAME/KEY: modified_base
<222> LOCATION: (29)..(29)
<223> OTHER INFORMATION: m5c

<400> SEQUENCE: 29
ugaauaccaa ugcaaaagca ttggtattca                                       30

<210> SEQ ID NO 30
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c

<400> SEQUENCE: 30
gcattggtat tca                                                         13

<210> SEQ ID NO 31
<211> LENGTH: 13
```

```
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(11)
<223> OTHER INFORMATION: ribonucleoside
<220> FEATURE:
<221> NAME/KEY: modified_base
<222> LOCATION: (11)..(13)
<223> OTHER INFORMATION: Phosphorothioate bond between nucleic acids
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: cm

<400> SEQUENCE: 31
ugaauaccaa ugc                                                        13

<210> SEQ ID NO 32
<211> LENGTH: 45
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (14)..(30)
<223> OTHER INFORMATION: ribonucleoside
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (31)..(31)
<223> OTHER INFORMATION: LNA
<220> FEATURE:
<221> NAME/KEY: modified_base
<222> LOCATION: (31)..(45)
<223> OTHER INFORMATION: Phosphorothioate bond between nucleic acids
<220> FEATURE:
```

```
<221> NAME/KEY: modified_base
<222> LOCATION: (33)..(33)
<223> OTHER INFORMATION: LNA
<220> FEATURE:
<221> NAME/KEY: modified_base
<222> LOCATION: (36)..(37)
<223> OTHER INFORMATION: LNA
<220> FEATURE:
<221> NAME/KEY: modified_base
<222> LOCATION: (40)..(40)
<223> OTHER INFORMATION: m5c
<220> FEATURE:
<221> NAME/KEY: modified_base
<222> LOCATION: (40)..(40)
<223> OTHER INFORMATION: LNA
<220> FEATURE:
<221> NAME/KEY: modified_base
<222> LOCATION: (42)..(42)
<223> OTHER INFORMATION: m5c
<220> FEATURE:
<221> NAME/KEY: modified_base
<222> LOCATION: (42)..(42)
<223> OTHER INFORMATION: LNA
<220> FEATURE:
<221> NAME/KEY: modified_base
<222> LOCATION: (44)..(45)
<223> OTHER INFORMATION: m5c
<220> FEATURE:
<221> NAME/KEY: modified_base
<222> LOCATION: (44)..(45)
<223> OTHER INFORMATION: LNA

<400> SEQUENCE: 32
cgattggtat cgcaaaagcg auaccaaucg ccattgtcac actcc          45

<210> SEQ ID NO 33
<211> LENGTH: 45
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (1)..(15)
<223> OTHER INFORMATION: Phosphorothioate bond between nucleic acids
<220> FEATURE:
<221> NAME/KEY: modified_base
<222> LOCATION: (3)..(3)
<223> OTHER INFORMATION: LNA
<220> FEATURE:
<221> NAME/KEY: modified_base
<222> LOCATION: (6)..(7)
<223> OTHER INFORMATION: LNA
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (10)..(10)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (12)..(12)
```

<223> OTHER INFORMATION: LNA
<220> FEATURE:
<221> NAME/KEY: modified_base
<222> LOCATION: (14)..(15)
<223> OTHER INFORMATION: m5c
<220> FEATURE:
<221> NAME/KEY: modified_base
<222> LOCATION: (14)..(15)
<223> OTHER INFORMATION: LNA
<220> FEATURE:
<221> NAME/KEY: modified_base
<222> LOCATION: (16)..(32)
<223> OTHER INFORMATION: ribonucleoside
<220> FEATURE:
<221> NAME/KEY: modified_base
<222> LOCATION: (33)..(45)
<223> OTHER INFORMATION: Phosphorothioate bond between nucleic acids
<220> FEATURE:
<221> NAME/KEY: modified_base
<222> LOCATION: (43)..(43)
<223> OTHER INFORMATION: m5c
<220> FEATURE:
<221> NAME/KEY: modified_base
<222> LOCATION: (43)..(45)
<223> OTHER INFORMATION: LNA
<220> FEATURE:
<221> NAME/KEY: modified_base
<222> LOCATION: (45)..(45)
<223> OTHER INFORMATION: m5c

<400> SEQUENCE: 33
ccattgtcac actccgcgau accaaucgaa aacgattggt atcgc            45

<210> SEQ ID NO 34
<211> LENGTH: 51
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(18)
<223> OTHER INFORMATION: ribonucleoside
<220> FEATURE:
<221> NAME/KEY: modified_base
<222> LOCATION: (19)..(19)
<223> OTHER INFORMATION: m5c
<220> FEATURE:
<221> NAME/KEY: modified_base
<222> LOCATION: (19)..(20)
<223> OTHER INFORMATION: LNA
<220> FEATURE:
<221> NAME/KEY: modified_base
<222> LOCATION: (19)..(32)
<223> OTHER INFORMATION: Phosphorothioate bond between nucleic acids
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (31)..(32)
<223> OTHER INFORMATION: LNA
<220> FEATURE:

```
<221> NAME/KEY: modified_base
<222> LOCATION: (33)..(36)
<223> OTHER INFORMATION: ribonucleoside
<220> FEATURE:
<221> NAME/KEY: modified_base
<222> LOCATION: (37)..(37)
<223> OTHER INFORMATION: m5c
<220> FEATURE:
<221> NAME/KEY: modified_base
<222> LOCATION: (37)..(37)
<223> OTHER INFORMATION: LNA
<220> FEATURE:
<221> NAME/KEY: modified_base
<222> LOCATION: (37)..(51)
<223> OTHER INFORMATION: Phosphorothioate bond between nucleic acids
<220> FEATURE:
<221> NAME/KEY: modified_base
<222> LOCATION: (39)..(39)
<223> OTHER INFORMATION: LNA
<220> FEATURE:
<221> NAME/KEY: modified_base
<222> LOCATION: (42)..(43)
<223> OTHER INFORMATION: LNA
<220> FEATURE:
<221> NAME/KEY: modified_base
<222> LOCATION: (46)..(46)
<223> OTHER INFORMATION: m5c
<220> FEATURE:
<221> NAME/KEY: modified_base
<222> LOCATION: (46)..(46)
<223> OTHER INFORMATION: LNA
<220> FEATURE:
<221> NAME/KEY: modified_base
<222> LOCATION: (48)..(48)
<223> OTHER INFORMATION: m5c
<220> FEATURE:
<221> NAME/KEY: modified_base
<222> LOCATION: (48)..(48)
<223> OTHER INFORMATION: LNA
<220> FEATURE:
<221> NAME/KEY: modified_base
<222> LOCATION: (50)..(51)
<223> OTHER INFORMATION: m5c
<220> FEATURE:
<221> NAME/KEY: modified_base
<222> LOCATION: (50)..(51)
<223> OTHER INFORMATION: LNA

<400> SEQUENCE: 34
aggccagugc uaagaaaact tagcactggc ctaaaaccat tgtcacactc c        51

<210> SEQ ID NO 35
<211> LENGTH: 15
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (1)..(15)
<223> OTHER INFORMATION: Phosphorothioate bond between nucleic acids
<220> FEATURE:
<221> NAME/KEY: modified_base
<222> LOCATION: (3)..(3)
<223> OTHER INFORMATION: LNA
<220> FEATURE:
<221> NAME/KEY: modified_base
<222> LOCATION: (6)..(7)
```

```
<223> OTHER INFORMATION: LNA
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (10)..(10)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (12)..(12)
<223> OTHER INFORMATION: LNA
<220> FEATURE:
<221> NAME/KEY: modified_base
<222> LOCATION: (14)..(15)
<223> OTHER INFORMATION: m5c
<220> FEATURE:
<221> NAME/KEY: modified_base
<222> LOCATION: (14)..(15)
<223> OTHER INFORMATION: LNA

<400> SEQUENCE: 35
ccattgtcac actcc                                                15

<210> SEQ ID NO 36
<211> LENGTH: 13
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: Phosphorothioate bond between nucleic acids
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (13)..(13)
<223> OTHER INFORMATION: m5c

<400> SEQUENCE: 36
cgattggtat cgc                                                  13

<210> SEQ ID NO 37
<211> LENGTH: 28
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (1)..(1)
<223> OTHER INFORMATION: gm
```

```
<220> FEATURE:
<221> NAME/KEY: modified_base
<222> LOCATION: (1)..(4)
<223> OTHER INFORMATION: Phosphorothioate bond between nucleic acids
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(13)
<223> OTHER INFORMATION: ribonucleoside
<220> FEATURE:
<221> NAME/KEY: modified_base
<222> LOCATION: (14)..(14)
<223> OTHER INFORMATION: m5c
<220> FEATURE:
<221> NAME/KEY: modified_base
<222> LOCATION: (14)..(14)
<223> OTHER INFORMATION: LNA
<220> FEATURE:
<221> NAME/KEY: modified_base
<222> LOCATION: (14)..(28)
<223> OTHER INFORMATION: Phosphorothioate bond between nucleic acids
<220> FEATURE:
<221> NAME/KEY: modified_base
<222> LOCATION: (16)..(16)
<223> OTHER INFORMATION: LNA
<220> FEATURE:
<221> NAME/KEY: modified_base
<222> LOCATION: (19)..(20)
<223> OTHER INFORMATION: LNA
<220> FEATURE:
<221> NAME/KEY: modified_base
<222> LOCATION: (23)..(23)
<223> OTHER INFORMATION: m5c
<220> FEATURE:
<221> NAME/KEY: modified_base
<222> LOCATION: (23)..(23)
<223> OTHER INFORMATION: LNA
<220> FEATURE:
<221> NAME/KEY: modified_base
<222> LOCATION: (25)..(25)
<223> OTHER INFORMATION: m5c
<220> FEATURE:
<221> NAME/KEY: modified_base
<222> LOCATION: (25)..(25)
<223> OTHER INFORMATION: LNA
<220> FEATURE:
<221> NAME/KEY: modified_base
<222> LOCATION: (27)..(28)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 37
gcgauaccaa ucgccattgt cacactcc                                      28
```

SINGLE-STRANDED OLIGONUCLEOTIDE

CROSS-REFERENCE TO RELATED APPLICATIONS

This patent application is the U.S. national phase of International Patent Application No. PCT/JP2017/002831, filed Jan. 26, 2017, which claims the benefit of Japanese Patent Application No. 2016-012804, filed on Jan. 26, 2016, and Japanese Patent Application No. 2016-158833, filed on Aug. 12, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 33,218 bytes ASCII (Text) file named "740008Sequence-Listing.txt," created Jul. 25, 2018.

TECHNICAL FIELD

The present invention relates to a single-stranded oligonucleotide.

BACKGROUND ART

Antisense oligonucleotides (ASO) are single-stranded DNA, RNA and/or structural analogues thereof composed of about 8 to 30 bases that are complementary to the mRNA or mRNA precursor of a target gene or non-coding RNA (ncRNA) such as ribosomal RNA, transfer RNA or miRNA. ASO suppress the function of mRNA, mRNA precursors or ncRNA by forming a double strand with mRNA, mRNA precursor or ncRNA targeted by that antisense oligonucleotide.

However, practical application of ASO is difficult since they are easily degraded by nucleases in the body and their uptake efficiency into target cells is low.

In order to overcome these two major problems, research has been conducted for many years on chemical modification of the active ingredient in the form of the oligonucleotide per se as well as on drug delivery systems (DDS) capable of delivering an oligonucleotide into a target cell.

Known examples of chemical modification of ASO per se include S-oligo (phosphorothioate), in which the phosphate moiety has been modified, and 2',4'-BNA (bridged nucleic acid)/LNA (locked nucleic acid), in which the sugar moiety has been modified (see Patent Documents 1 to 5).

Known examples of DDS include methods utilizing carriers such as cationic liposomes or polymeric micelles. In addition, Patent Document 6 describes an ASO in which a GalNac (N-acetylgalactosamine) derivative, which is a sugar derivative having the ability to interact with asialoglycoprotein receptors, is bound via a linker, and that expression of a target gene in the liver is suppressed following administration of this ASO.

Patent Document 7 and Non-Patent Document 1 describe that, by bonding tocopherol (Toc) to a double-stranded oligonucleotide (HDO) containing an RNA oligonucleotide complementary to ASO, the HDO is delivered and concentrated in the liver and expression of a target gene in the liver is suppressed in mice. Patent Document 8 describes an ASO in which a GalNac derivative is bound to an HDO via a linker, and that expression is suppressed more efficiently than tocopherol (Toc) modification when the antisense oligonucleotide is administered subcutaneously.

Patent Document 9 describes that an oligonucleotide (HCDO), in which an ASO is bound to the end of an RNA strand of a double-stranded oligonucleotide unit consisting of DNA and RNA, suppresses a target RNA more efficiently than the ASO.

PRIOR ART DOCUMENTS

Non-Patent Documents

Non-Patent Document 1: Nature Communications, Vol. 6, Article No. 7969 (2015)

Patent Documents

Patent Document 1: International Publication No. WO 98/39352
Patent Document 2: International Publication No. WO 2005/021570
Patent Document 3: International Publication No. WO 2003/068795
Patent Document 4: International Publication No. WO 2011/052436
Patent Document 5: International Publication No. WO 2011/156202
Patent Document 6: International Publication No. WO 2014/179620
Patent Document 7: International Publication No. WO 2013/089283
Patent Document 8: International Publication No. WO 2015/105083
Patent Document 9: International Publication No. WO 2014/192310

DISCLOSURE OF THE INVENTION

Problems to be Solved by the Invention

There is a desire for novel nucleic acid pharmaceuticals capable of efficiently suppressing the expression of a target gene when indicated for use as pharmaceuticals in mammals, including humans, in the clinical setting. In addition, in the case of producing double-stranded oligonucleotides (such as the aforementioned HDO or HCDO), a step is required for separately synthesizing the antisense strand and complementary RNA strand followed by hybridizing these strands. Moreover, when administering to animals or cells, it is necessary that the double-stranded oligonucleotide be inhibited from dissociating into single strands, and it can be presumed that there are cases in which considerable effort is required when establishing handling conditions for that purpose.

An object of the present invention is to provide a novel oligonucleotide capable of suppressing expression of a target gene with high efficiency. In addition, an object of the present invention is to provide an oligonucleotide that can be more easily produced than double-stranded oligonucleotides.

Means for Solving the Problems

The inventors of the present invention found that, by coupling an oligodeoxyribonucleotide and a complementary chain containing its corresponding RNA with a linker such as DNA or RNA that is degraded under physiological conditions to obtain a single-stranded oligonucleotide having a structure that partially hybridizes within a molecule thereof and has an antisense sequence capable of controlling expression of a target gene, the single-stranded oligonucleotide demonstrates an antisense effect that is equal to or greater than that of the double-stranded oligonucleotide. In addition, since the single-stranded oligonucleotide consists of a single strand, it can be produced efficiently without requiring a hybridization step for forming a double strand. The present invention includes the aspects indicated below.

1. A single-stranded oligonucleotide represented by the formula:

X-L-Y (wherein, X represents a group derived from a first oligonucleotide composed of 7 to 100 nucleotides that are independently selected from a deoxyribonucleotide, ribonucleotide and sugar-modified nucleotide and that contains at least one nucleotide of which at least one of a sugar moiety, base moiety and phosphate moiety has been modified, Y represents a group derived from a second oligonucleotide composed of 4 to 100 nucleotides that are independently selected from a deoxyribonucleotide, ribonucleotide and sugar-modified nucleotide, and L represents a group derived from a third oligonucleotide that respectively covalently bonds with the first oligonucleotide and the second oligonucleotide at both ends thereof and is degraded under physiological conditions; wherein, the first oligonucleotide has a nucleotide sequence X, and the second oligonucleotide has a nucleotide sequence Y, the nucleotide sequence X contains a first nucleotide sequence that is capable of hybridizing with at least a portion of the second oligonucleotide and contains at least four contiguous nucleotides recognized by RNase H, the nucleotide sequence Y contains a second nucleotide sequence that is capable of hybridizing with at least a portion of the first oligonucleotide and contains at least one ribonucleotide, at least one of the nucleotide sequence X and the nucleotide sequence Y contains at least one antisense sequence capable of hybridizing with a target RNA, and in the case of having two or more antisense sequences, the target RNA hybridized by each antisense sequence may be the same or different), wherein X and Y hybridize by the first nucleotide sequence portion and the second nucleotide sequence portion.

2. The single-stranded oligonucleotide described in 1, wherein X contains at least one sugar-modified nucleotide, and the first nucleotide sequence is the antisense sequence and contains at least four contiguous nucleotides recognized by RNase H when hybridizing with the target RNA.

3. The single-stranded oligonucleotide described in 1 or 2, wherein X bonds to L on the 3'-side and Y bonds to L on the 5'-side.

4. The single-stranded oligonucleotide described in 1 or 2, wherein X bonds to L on the 5'-side and Y bonds to L on the 3'-side.

5. The single-stranded oligonucleotide described in any of 1 to 4, wherein nucleotides contained in the third oligonucleotide are mutually coupled through phosphodiester bonds.

6. The single-stranded oligonucleotide described in any of 1 to 5, wherein the third oligonucleotide is DNA or RNA.

7. The single-stranded oligonucleotide described in any of 1 to 6, wherein the first oligonucleotide contains a sugar-modified nucleotide that bonds adjacent to at least one of the 5'-side and 3'-side of the first nucleotide sequence portion.

8. The single-stranded oligonucleotide described in any of 1 to 7, wherein the first oligonucleotide contains a sugar-modified nucleotide bound adjacent to the 5'-side and 3'-side of the first nucleotide sequence portion.

9. The single-stranded oligonucleotide described in any of 1 to 8, wherein the first oligonucleotide contains a phosphorothioate bond.

10. The single-stranded oligonucleotide described in any of 1 to 9, wherein the first nucleotide sequence is composed of 4 to 20 nucleotides including at least one deoxyribonucleotide.

11. The single-stranded oligonucleotide described in any of 1 to 10, wherein the second nucleotide sequence is a sequence that contains at least four contiguous nucleotides cleaved by RNase H.

12. The single-stranded oligonucleotide described in 11, wherein the second oligonucleotide contains a sugar-modified nucleotide bound adjacent to at least one of the 5'-side and 3'-side of the second nucleotide sequence portion.

13. The single-stranded oligonucleotide described in 11 or 12, wherein at least one of the 5'-side and 3'-side of the second nucleotide sequence portion is coupled to an adjacent nucleotide through a phosphorothioate bond.

14. The single-stranded oligonucleotide described in any of 1 to 13, wherein the nucleotide sequence Y contains at least one antisense sequence.

15. The single-stranded oligonucleotide described in 14, wherein the Y has the second nucleotide sequence portion between the antisense sequence portion and L.

16. The single-stranded oligonucleotide described in 14 or 15, wherein the antisense sequence contained by the nucleotide sequence Y is a sequence that contains at least four contiguous nucleotides recognized by RNase H when hybridizing with a target RNA.

17. The single-stranded oligonucleotide described in 14 or 15, wherein the antisense sequence portion contained by the Y contains at least one sugar-modified nucleotide but does not contain an oligonucleotide strand composed of four contiguous deoxyribonucleotides.

18. The single-stranded oligonucleotide described in 16 or 17, wherein the nucleotide sequence X contains a sequence that is able to hybridize with at least a portion of the antisense sequence portion contained by the Y and contains at least four contiguous nucleotides cleaved by RNase H.

19. The single-stranded oligonucleotide described in any of 1 to 18, wherein X contains the 5'-end or 3'-end.

20. The single-stranded oligonucleotide described in any of 1 to 18, further containing a group represented by the formula:

X'-L'-

(wherein, X' is a group derived from a fourth oligonucleotide composed of 7 to 100 nucleotides that are independently selected from a deoxyribonucleotide, ribonucleotide and sugar-modified nucleotide and that contains at least one nucleotide of which at least one of the sugar moiety, base moiety and phosphate moiety has been modified, and L' represents a group derived from a fifth oligonucleotide that respectively covalently bonds with the first oligonucleotide and the fourth oligonucleotide at both ends thereof and is degraded under physiological conditions; wherein, the fourth oligonucleotide has an antisense sequence capable of hybridizing with a target RNA).

21. The single-stranded oligonucleotide described in 20, wherein X' contains at least one sugar-modified nucleotide, and the antisense sequence possessed by the fourth oligonucleotide contains at least four contiguous nucleotides recognized by RNase H when hybridizing with a target RNA.

22. The single-stranded oligonucleotide described in 20, wherein the antisense sequence portion contained by the fourth oligonucleotide contains at least one sugar-modified nucleotide, but does not contain an oligonucleotide strand composed of four contiguous deoxyribonucleotides.

23. The single-stranded oligonucleotide described in 21 or 22, wherein the antisense sequence portion contained by the fourth oligonucleotide hybridizes with at least a portion of the second oligonucleotide.

24. The single-stranded oligonucleotide described in any of 20 to 23, wherein nucleotides contained in the fifth oligonucleotide are mutually coupled through phosphodiester bonds.

25. The single-stranded oligonucleotide described in any of 20 to 24, wherein the fifth oligonucleotide is DNA or RNA.

26. The single-stranded oligonucleotide described in any of 1 to 25, containing a sugar-modified nucleotide bound adjacent to at least one of the 5'-side and 3'-side of the antisense sequence portion.

27. The single-stranded oligonucleotide described in any of 1 to 26, containing sugar-modified nucleotides bound adjacent to the 5'-side and 3'-side of the antisense sequence portion.

28. The single-stranded oligonucleotide described in any of 1 to 27, wherein the antisense sequence is composed of 4 to 20 nucleotides including at least one deoxyribonucleotide.

29. The single-stranded oligonucleotide described in any of 1 to 28, wherein the antisense sequence portion contains a phosphorothioate bond.

30. The single-stranded oligonucleotide described in any of 1 to 29, wherein Y contains the 5'-end or 3'-end.

31. The single-stranded oligonucleotide described in any of 1 to 30, further containing a group derived from a functional molecule having at least one function selected from the group consisting of a labeling function, a purifying function and a target site delivery function.

32. The single-stranded oligonucleotide described in 31, wherein the functional molecule is selected from the group consisting of sugars, lipids, peptides, proteins and derivatives thereof.

33. The single-stranded oligonucleotide described in 31 or 32, wherein the functional molecule is a lipid selected from the group consisting of cholesterol, tocopherol and tocotrienol.

34. The single-stranded oligonucleotide described in 31 or 32, wherein the functional molecule is a sugar derivative that interacts with an asialoglycoprotein receptor.

35. The single-stranded oligonucleotide described in 31 or 32, wherein the functional molecule is a peptide or protein selected from the group consisting of receptor ligands and antibodies.

36. A pharmaceutical composition containing the single-stranded oligonucleotide described in any of 1 to 35 and a pharmacologically acceptable carrier.

37. A method for controlling the function of a target RNA, including a step for contacting the single-stranded oligonucleotide described in any of 1 to 35 with a cell.

38. A method for controlling the function of a target RNA in a mammal, including a step for administering a pharmaceutical composition containing the single-stranded oligonucleotide described in any of 1 to 35 to the mammal.

39. A use of the single-stranded oligonucleotide described in any of 1 to 35 for controlling the function of a target RNA in a mammal.

40. A method for producing the single-stranded oligonucleotide described in any of 1 to 35, including a step for elongating the nucleotide strand at the 3'-end or 5'-end of an oligonucleotide containing at least one of X, L and Y.

Effects of the Invention

According to the present invention, an oligonucleotide can be provided that is able to control expression of a target gene with high efficiency. In addition, an oligonucleotide can be provided that can be produced more easily than a double-stranded oligonucleotide (such as an HDO or HCDO).

The single-stranded oligonucleotide of the present invention is able to effectively control expression of a target gene by a constituent thereof in the form of an antisense oligonucleotide, and is useful as a nucleic acid pharmaceutical.

BEST MODE FOR CARRYING OUT THE INVENTION

Figure 1:
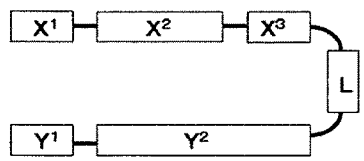
FIG. 1 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

The terms used in the present description are used in the sense in which they are ordinarily used in the art unless specifically indicated otherwise. The following provides an explanation of terms used in the present description. Furthermore, the terms used in the present description have the same meaning both in the case they are used alone and in the case they are used in conjunction with other terms unless specifically indicated otherwise.

"Antisense effect" refers to controlling the function of a target RNA by hybridizing a target RNA selected corresponding to a target gene and an oligonucleotide having a sequence complementary to a partial sequence thereof. For example, in the case the target RNA is mRNA, an antisense effect refers to translation of the aforementioned target RNA being suppressed by hybridization, an effect that converts a splicing function such as exon skipping, or the aforementioned target RNA being degraded as a result of recognition of a hybridized portion. Although examples of oligonucleotides in which the aforementioned antisense effect is demonstrated include DNA and oligodeoxyribonucleotides, oligonucleotides in which an antisense effect is demonstrated are not limited thereto, but rather may be RNA, oligoribonucleotides or oligonucleotides that have been designed to normally demonstrate an antisense function.

"Target RNA" refers to mRNA, mRNA precursor or ncRNA, and includes mRNA transcribed from genomic DNA encoding a target gene, mRNA not subjected to base modification, and mRNA precursor or ncRNA that have not been subjected to splicing. There are no particular limitations on "target RNA" for which the function thereof is controlled by an antisense effect, and examples thereof include RNA associated with genes for which expression increases in various diseases. "Target RNA" may be any RNA synthesized by DNA-dependent RNA polymerase, and is preferably mRNA or mRNA precursor. More preferably, the "target RNA" is mammal mRNA or mRNA precursor and even more preferably human mRNA or mRNA precursor.

"Hybridize" refers to the act of forming a double-strand between oligonucleotides containing complementary sequences or groups derived from those oligonucleotides, and constitutes a phenomenon in which oligonucleotides containing complementary sequences or groups derived from those oligonucleotides form a double strand.

"Complementary" refers two nucleic acid bases being able to form a Watson-Crick base pair (naturally-occurring base pair) or non-Watson-Crick base pair (such as a Hoogsteen base pair) via hydrogen bonds. Two oligonucleotides or groups derived from those oligonucleotides are able to "hybridize" in the case their sequences are complementary. Although it is not necessary for sequences to be completely complementary in order for two oligonucleotides or groups derived from those oligonucleotides to hybridize, complementarity for two oligonucleotides or groups derived from those oligonucleotides to hybridize is preferably 70% or more, more preferably 80% or more and even more preferably 95% or more (such as 95%, 96%, 97%, 98% or 99%). Sequence complementarity can be determined by using a computer program that automatically identifies the partial sequences of oligonucleotides. One example of software used for that purpose is OligoAnalyzer available from Integrated DNA Technologies. This program can also be accessed online from a Web site. A person with ordinary skill in the art is therefore able to easily determine conditions (such as temperature or salt concentration) for enabling hybridization of two oligonucleotides or groups derived from those oligonucleotides. In addition, a person with ordinary skill in the art can easily design an antisense oligonucleotide complementary to target RNA by, for example, using software such as the BLAST program based on nucleotide sequence data of the target RNA. Literature such as the Proceedings of the National Academy of Science, USA (1990, Vol. 87, pp. 2264-2268) or the Journal of Molecular Biology (1990, Vol. 215, p. 403) can be referred to with respect to the BLAST program.

A "group derived from an oligonucleotide" refers to the partial structure of an oligonucleotide formed by removing at least one hydrogen atom or hydroxyl group and the like on the 3'-end or 5'-end of an oligonucleotide, and at least one of the 3'-end or the 5'-end of the oligonucleotide covalently bonds to another group (such as a group derived from an oligonucleotide).

A "nucleotide sequence" refers to the base sequence of nucleotides that compose an oligonucleotide.

A "nucleotide sequence portion" refers to a partial structure of a region having the aforementioned nucleotide sequence in an oligonucleotide strand.

Furthermore, in the present description, a "nucleotide sequence" containing or not containing a nucleotide or oligonucleotide strand has the same meaning as the corresponding "nucleotide sequence portion" containing or not containing that nucleotide or that oligonucleotide strand. In addition, a "nucleotide sequence" has the same meaning as a base sequence of a "nucleotide sequence portion" containing or not containing that nucleotide or that oligonucleotide strand.

A "sequence portion" refers to a partial structure of an oligonucleotide strand. For example, a sequence portion containing nucleotides is a partial structure of a region of an oligonucleotide strand that contains the nucleotides.

A nucleotide sequence being a sequence of selected from nucleotides or a sequence of contiguous nucleotides has the same meaning as the corresponding nucleotide sequence portion being a sequence portion selected from those nucleotides or a sequence portion of contiguous nucleotides, respectively.

"RNase H" is typically known to be a ribonuclease that recognizes a double strand obtained by hybridizing DNA and RNA and cleaves the RNA to form single-stranded DNA. RNase H is not limited to recognizing a double strand obtained by hybridizing DNA and RNA, but can also recognize a double strand in which at least one of the base moiety, phosphodiester bond moiety or sugar moiety of at least one of DNA and RNA has been modified. For example, RNase H can also recognize a double strand obtained by hybridizing an oligodeoxyribonucleotide and an oligoribonucleotide.

Accordingly, DNA can be recognized by RNase H when hybridizing with RNA. This applies similarly in the case at least one of a base moiety, phosphodiester bond moiety and sugar moiety has been modified in at least one of DNA and RNA. For example, a typical example thereof is an oligonucleotide in which a phosphodiester moiety of DNA has been modified to phosphorothioate.

RNA can be cleaved by RNase H when hybridizing with DNA. This applies similarly in the case at least one of a base moiety, phosphodiester bond moiety and sugar moiety has been modified in at least one of DNA and RNA.

Examples of modifying DNA and/or RNA able to be recognized by RNase H are described in the literature, examples of which include Nucleic Acids Research (2014, Vol. 42, No. 8, pp. 5378-5389, Bioorganic and Medicinal Chemistry Letters (2008, Vol. 18, pp. 2296-2300), Molecular Biosystems (2009, Vol. 5, pp. 838-843), Nucleic Acid Therapeutics (2015, Vol. 25, pp. 266-274) and The Journal of Biological Chemistry (2004, Vol. 279, No. 35, pp. 36317-36326).

The RNase H used in the present invention is preferably mammal RNase H, more preferably human RNase H, and particularly preferably human RNase Hl.

A "deoxyribonucleotide" is a molecule that has a base bound to a carbon atom at the 1'-position of 2'-deoxyribose and a phosphate group at the 3'-position or 5'-position. A deoxyribonucleotide in the present invention may be a naturally-occurring deoxyribonucleotide or a deoxyribonucleotide in which a base moiety or phosphodiester bond moiety of a naturally-occurring deoxyribonucleotide has been modified. Modification of a base moiety or modification of a phosphodiester bond moiety on a single deoxyribonucleotide may be carried out on a combination of a plurality of types of modifications. The aforementioned modified deoxyribonucleotides are described in the literature, examples of which include the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365). A "deoxyribonucleotide" in the present invention can also refer to a "sugar deoxyribonucleotide" or "sugar deoxyribose nucleotide".

When the aforementioned "deoxyribonucleotide" composes the single-stranded oligonucleotide of the present invention, normally the 3'-position of the deoxyribonucleotide is coupled to another nucleotide through a phosphodiester bond or modified phosphodiester bond, and the 5'-position of the deoxyribonucleotide is coupled to another nucleotide through a phosphodiester bond or modified phosphodiester bond. A deoxyribonucleotide on the 3'-end of the single-stranded oligonucleotide molecule of the present invention preferably has a hydroxyl group or phosphate group at the 3'-position thereof, and the 5'-position is as previously described. A deoxyribonucleotide on the 5'-end of the single-stranded oligonucleotide molecule preferably has a hydroxyl group or phosphate group on the 5'-side thereof and the 3'-position is as previously described.

An "oligodeoxyribonucleotide" refers to an oligonucleotide composed of the aforementioned deoxyribonucleotides. Deoxyribonucleotides composing the oligodeoxyribonucleotide may each be the same or different.

"DNA" refers to an oligonucleotide composed of naturally-occurring deoxyribonucleotides. The naturally-occurring deoxyribonucleotides composing DNA may be each be the same or different.

A "ribonucleotide" is a molecule having a base bound to a carbon atom at the 1'-position of ribose and a phosphate group at the 2'-position, 3'-position or 5'-position. A ribonucleotide in the present invention may be a naturally-occurring ribonucleotide or a ribonucleotide in which a base moiety or phosphodiester bond moiety of a naturally-occurring ribonucleotide has been modified. Modification of a base moiety or modification of a phosphodiester bond moiety on a single ribonucleotide may be carried out on a combination of a plurality of types of modifications. The aforementioned modified ribonucleotide refers to that described in the literature, examples of which include the Journal of Medicinal Chemistry (2016, Vol. 59, No. 21, pp. 9645-9667), Medicinal Chemistry Communications (2014, Vol. 5, pp. 1454-1471) and Future Medicinal Chemistry (2011, Vol. 3, No. 3, pp. 339-365). A "ribonucleotide" in the present invention can also refer to a "sugar ribonucleotide" or "sugar ribose nucleotide".

When the aforementioned "ribonucleotide" composes the single-stranded oligonucleotide molecule of the present invention, the 3'-position of the ribonucleotide is typically coupled to another nucleotide through a phosphodiester bond or modified phosphodiester bond, and the 5'-position of the ribonucleotide is coupled to another nucleotide through a phosphodiester bond or modified phosphodiester bond. A ribonucleotide on the 3'-end of the single-stranded oligonucleotide molecule of the present invention preferably has a hydroxyl group or phosphate group at the 3'-position thereof and the 5'-position is as previously described. A ribonucleotide on the 5'-end of the single-stranded oligonucleotide molecule of the present invention preferably has a hydroxyl group or phosphate group at the 5'-position thereof and the 3'-position is as previously described.

"Oligoribonucleotide" refers to an oligonucleotide composed of the aforementioned ribonucleotides. The ribonucleotides that compose an oligoribonucleotide may each be the same or different.

"RNA" refers to an oligonucleotide composed of naturally-occurring ribonucleotides. The naturally-occurring ribonucleotides that compose the RNA may each be the same or different.

"Sugar-modified nucleotide" refers to a nucleotide in which the a sugar moiety of the aforementioned deoxyribonucleotide or ribonucleotide is partially substituted with one or more substituents, the entire sugar backbone thereof has been replaced with a sugar backbone differing from ribose or 2'-deoxyribose (in the manner of a 5- or 6-membered sugar backbone such as hexitol or threose), or the entire sugar backbone thereof has been replaced with a 5- or 6-membered, saturated or unsaturated ring (such as cyclohexane, cyclohexene or morpholine) or a partial structure that allows the formation of a 5- or 6-membered ring by hydrogen bonding (such as peptide structure). A base moiety of a "sugar-modified nucleotide" may be a naturally-occurring base or a modified base. In addition, a phosphodiester bond moiety of a "sugar-modified nucleotide" may be a phosphodiester bond or a modified phosphodiester bond. Modification of a base moiety or modification of a phosphodiester bonding site on a single sugar-modified nucleotide may be carried out on a combination of a plurality of types of modifications.

A "sugar-modified nucleotide" may be a bridged nucleotide or non-bridged nucleotide. Examples of sugar-modified nucleotides include nucleotides disclosed as being preferable for use in an antisense method in, for example, Japanese Unexamined Patent Publication No. H10-304889, International Publication No. WO 2005/021570, Japanese Unexamined Patent Publication No. H10-195098, Japanese Translation of PCT Application No. 2002-521310, International Publication No. WO 2007/143315, International Publication No. WO 2008/043753, International Publication No. WO 2008/029619 or International Publication No. 2008/049085 (these documents are to be collectively referred to as "antisense method-related documents"). The aforementioned documents disclose nucleotides such as hexitol nucleotides (HNA), cyclohexene nucleotides (CeNA), peptide nucleic acids (PNA), glycol nucleic acids (GNA), threose nucleotides (TNA), morpholine nucleic acids, tricyclo-DNA (tcDNA), 2'-O-methyl nucleotides, 2'-MOE (2'-O-methoxyethyl) nucleotides, 2'-AP (2'-O-aminopropyl) nucleotide, 2'-fluoronucleotide, 2'-F-arabinonucleotides (2'-F-ANA), bridged nucleotides (BNA (bridged nucleic acids)) and 2'-O-methylcarbamoylethyl nucleotides (MCE). In addition, sugar-modified nucleotides are also disclosed in the literature such as the Journal of Medical Chemistry (2016, Vol. 59, No. 21, pp. 9645-9667), Medicinal Chemistry Communications (2014, Vol. 5, 1454-1471) or Future Medicinal Chemistry (2011, Vol. 3, No. 3, pp. 339-365).

When the aforementioned "sugar-modified nucleotide" composes the single-stranded oligonucleotide molecule of the present invention, the 3'-position of the sugar-modified nucleotide is, for example, coupled to another nucleotide through a phosphodiester bond or modified phosphodiester bond, and the 5'-position of the sugar-modified nucleotide is, for example, coupled to another nucleotide through a phosphodiester bond or modified phosphodiester bond. A sugar-modified nucleotide on the 3'-end of the single-stranded oligonucleotide molecule of the present invention preferably has, for example, a hydroxyl group or phosphate group at the 3'-position thereof, and the 5'-position is as previously described. A sugar-modified nucleotide on the 5'-end of the single-stranded oligonucleotide preferably has, for example, a hydroxyl group or phosphate group at the 5'-position thereof and the 3'-position is as previously described.

The base moieties in a deoxyribonucleotide, ribonucleotide and sugar-modified nucleotide are preferably at least one type selected from the group consisting of adenine (A), guanine (G), thymine (T), cytosine (C), uracil (U) and 5'-methylcytosine (5-me-C).

Examples of modifications of a base moiety in a deoxyribonucleotide, ribonucleotide and sugar-modified nucleotide include halogenation, methylation, ethylation, n-propylation, isopropylation, cyclopropylation, n-butylation, isobutylation, s-butylation, t-butylation, cyclobutylation, hydroxylation, amination, thionation and demethylation. Specific examples include 5-methylation, 5-fluorination, 5-iodination and N4-methylation of cytosine, 2-thionation, 5-demethylation, 5-fluorination, 5-bromination and 5-iodination of thymine, 2-thionation, 5-fluorination, 5-bromination and 5-iodination of uracil, N6-methylation and 8-bromination of adenine, and N2-methylation and 8-bromination of guanine. In addition, examples of modification of sugar moieties in nucleotides are disclosed in the Journal of Medicinal Chemistry (2016, Vol. 59, No. 21, pp. 9645-9667), Medicinal Chemistry Communications (2014, Vol. 5, 1454-1471) and Future Medicinal Chemistry (2011, Vol. 3, No. 3, pp. 339-365), and these can be used in the base moieties of deoxyribonucleotides, ribonucleotides and sugar-modified nucleotides.

Examples of modification of a phosphodiester bond moiety in deoxyribonucleotides, ribonucleotides and sugar-modified nucleotides include phosphorothioation, methylphosphonation (including chiral methylphosphonation), methylthiophosphonation, phosphorodithioation, phosphoroamidation, phosphoroamidothioation and boranophosphorylation.

Examples of modifications in which a sugar moiety of a deoxyribonucleotide or ribonucleotide is partially substituted with a single substituent include 2'-O-methylation, 2'-O-methoxyethylation (MOE), 2'-O-aminopropylation (AP), 2'-fluorination and 2'-O-methylcarbamoylethylation (MCE).

A "bridged nucleotide" refers to a sugar-modified nucleotide in which a bridging unit has been substituted by substitutions at two locations in a sugar moiety, and an example thereof is nucleotide that has been bridged at the 2'-position and 4'-position.

A nucleotide that has been bridged at the 2'-position and 4'-position (2',4'-BNA) is only required to be a nucleotide having a sugar moiety in which the carbon atom at the 2'-position and the carbon atom at the 4'-position are substituted with two or more atoms, and examples thereof include nucleotides having a sugar moiety that has been bridged at a C2-6 alkylene group (wherein the alkylene group is either unsubstituted or substituted with one or more substituents selected from the group consisting of a halogen atom, oxo group and thioxo group, and one or two methylene groups of the alkylene group are not replaced or are independently replaced with a group selected from the group consisting of —O—, —NR$^1$— (wherein, R$^1$ represents a hydrogen atom, C1-6 alkyl group or halo-C1-6 alkyl group) and —S—).

Groups that bridge the 2'-position and 4'-position of 2',4,'-BNA by combining the aforementioned substitutions and replacements may contain a group represented by, for example, —C(O)—O—, —O—C(O)—NR$^1$— (wherein, R$^1$ represents a hydrogen atom, C1-6 alkyl group or halo-C1-6 alkyl group), —C(O)—NR$^1$— (wherein, R$^1$ represents a hydrogen atom, C1-6 alkyl group or halo-C1-6 alkyl group) or —C(S)—NR$^1$— (wherein, R$^1$ represents a hydrogen atom, C1-6 alkyl group or halo-C1-6 alkyl group). Here, a sugar-modified nucleotide containing —C(S)—NR$^1$— can be synthesized from a sugar-modified nucleotide containing —C(O)—NR$^1$— or an intermediate thereof using a thiocarbonylation reagent (such as Lawesson's reagent) and carrying out a protection reaction and deprotection reaction as necessary.

Examples of this BNA include Locked Nucleic Acid® also referred to as LNA, α-L-methyleneoxy(4'-CH$_2$—O-2') BNA, β-D-thio(4'-CH$_2$—S-2')BNA, ethyleneoxy(4'-(CH$_2$)$_2$—O-2')BNA also referred to as ENA, β-D-thio(4'-CH$_2$—S-2')BNA, aminoxy(4'-CH$_2$—O—N(R$^{11}$)-2')BNA (wherein, R$^{11}$ represents H or CH$_3$), oxyamino(4'-CH$_2$—N (R$^{12}$)—O-2') also referred to as 2',4'-BNA$^{NC}$ (wherein, R$^{12}$ represents H or CH$_3$), 2',4'-BNA$^{COC}$, 3'-amino-2',4'-BNA, 5'-methyl BNA, (4'-CH(CH$_3$)—O-2')BNA also referred to as cEt-BNA, (4'-CH(CH$_2$OCH$_3$)—O-2')BNA also referred to as cMOE-BNA, amide-type BNA(4'-C(O)—N(R$^{13}$)-2') BNA (wherein, R$^{13}$ represents H or CH$_3$) also referred to as AmNA, and other BNA known among persons with ordinary skill in the art.

An "oligonucleotide" is a molecule having a structure in which one or more nucleotides are polymerized. When an "oligonucleotide" is composed of one nucleotide, that oligonucleotide can also be referred to as a "nucleotide".

A "nucleotide" refers to a molecule capable of serving as a structural unit of a nucleic acid (oligonucleotide), and normally has a base as constituents thereof. A nucleotide is composed of, for example, a sugar, a base and a phosphoric acid. Nucleotides include the aforementioned deoxyribonucleotides, ribonucleotides and sugar-modified nucleotides. Nucleotides contained in the single-stranded oligonucleotide molecule of the present invention are mutually coupled through respective and independent phosphodiester bonds or the aforementioned modified phosphodiester bonds. The nucleotide on the 3'-end of the single-stranded oligonucleotide molecule of the present invention preferably has a hydroxyl group or phosphate group, more preferably has a hydroxyl group, and normally has a hydroxyl group at the 3'-position thereof. The nucleotide on the 5'-end of the single-stranded oligonucleotide molecule preferably has a hydroxyl group or phosphate group, more preferably has a hydroxyl group, and normally has a hydroxyl group at the 5'-position thereof.

A "nucleotide of which at least one of a sugar moiety, base moiety and phosphate moiety has been modified" refers to a deoxyribonucleotide, in which at least one of the base moiety and phosphate moiety of a naturally-occurring deoxyribonucleotide has been modified, a ribonucleotide in which at least one of a base moiety and phosphate moiety of a naturally-occurring ribonucleotide has been modified, or a sugar-modified nucleotide.

Although there are no particular limitations on "at least four contiguous nucleotides recognized by RNase H" provided they include four or more contiguous nucleotides and are recognized by RNase H, the contiguous nucleotides are preferably independently selected from deoxyribonucleotides and sugar-modified nucleotides, and are more preferably independently selected from deoxyribonucleotides. These contiguous nucleotides may each be the same or different.

Although there are no particular limitations on "at least four contiguous nucleotides cleaved by RNase H" provided they include four contiguous nucleotides and are cleaved by RNase H, they include at least one ribonucleotide. In addition, the four contiguous nucleotides preferably include an oligonucleotide and more preferably include RNA. The contiguous nucleotides are more preferably independently selected from ribonucleotides. In addition, the contiguous nucleotides are more preferably mutually coupled through phosphodiester bonds. These contiguous nucleotides may each be the same or different.

A "C1-C6 alkyl group" refers to a linear or branched saturated hydrocarbon group having 1 to 6 carbon atoms, and examples thereof include a methyl group, ethyl group, n-propyl group, isopropyl group, n-butyl group, isobutyl group, s-butyl group, t-butyl group, n-pentyl group, isopentyl group, neopentyl group, n-hexyl group and isohexyl group.

A "C1-6 alkylene group" refers to a divalent substituent obtained by removing a single hydrogen atom at an arbitrary location from the aforementioned "C1-6 alkyl group", and examples thereof include a methylene group, ethylene (ethanediyl) group, propane-1,3-diyl group, propane-2,2-diyl group, 2,2-dimethylpropane-1,3-diyl group, hexane-1,6-diyl group and 3-methylbutane-1,2-diyl group.

A "C2-6 alkylene group" refers to a linear or branched divalent substituent having 2 to 6 carbon atoms, and examples thereof include an ethylene (ethanediyl) group, propane-1,3-diyl group, 2,2-dimethylpropane-1,3-diyl group, hexane-1,6-diyl group and 3-methylbutane-1,2-diyl group.

The abbreviation "n-" stands for normal, the abbreviation "s-" stands for secondary, and the abbreviation "t-" stands for tertiary.

A "C2-20 alkylene group" refers to a divalent substituent obtained by removing a single hydrogen atom at an arbitrary location from a linear or branched unsaturated hydrocarbon group having 2 to 20 carbon atoms.

A "C8-12 alkylene group" refers to a divalent substituent obtained by removing a single hydrogen atom at an arbitrary location from a linear or branched unsaturated hydrocarbon group having 8 to 12 carbon atoms.

A "C2-20 alkenylene group" refers to a divalent substituent obtained by removing a single hydrogen atom at an arbitrary location from a linear or branched unsaturated hydrocarbon group having 2 to 20 carbon atoms.

A "halogen atom" refers to a fluorine atom, chlorine atom, bromine atom or iodine atom.

A "halo-C1-6 alkyl group" refers to a substituent in which a hydrogen atom at an arbitrary location of the aforementioned "C1-6 alkyl group" has been substituted with one or more halogen atoms independently selected from a group of substituents consisting of a fluorine atom, chlorine atom, bromine atom and iodine atom.

An "oxo group" indicates a substituent in which an oxygen atom is substituted via a double bond (=O). In the case an oxo group is substituted for a carbon atom, the oxo group forms a carbonyl group together with the carbon atom.

A "thioxo group" indicates a substituent in which a sulfur atom is substituted via a double bond (=S). In the case a thioxo group is substituted for a carbon atom, the thioxo group forms a thiocarbonyl group together with the carbon atom.

The sugar-modified nucleotide is not limited to that exemplified here. Numerous sugar-modified nucleotides are known in the art, and sugar-modified nucleotides described in, for example, U.S. Pat. No. 8,299,039 of Tachas, et al. (and particularly columns 17 to 22), the Journal of Medicinal Chemistry (2016, Vol. 59, No. 21, 9645-9667), Medicinal Chemistry Communications (2014, Vol. 5, pp. 1454-1471) or Future Medicinal Chemistry (2011, Vol. 3, No. 3, pp. 339-365), can also be used as embodiments of the present invention.

A person with ordinary skill in the art is able to suitably select and use a sugar-modified nucleotide from among such sugar-modified nucleotides in consideration of such factors as antisense effect, affinity for a partial sequence of a target RNA or resistance to nuclease.

The following provides an explanation of an antisense sequence, antisense sequence portion, and nucleotide sequence portion that hybridizes with an antisense sequence in a molecule thereof as used in the present invention.

An "antisense sequence" refers to a base sequence of nucleotides that compose an oligonucleotide capable of hybridizing with a target RNA.

An "antisense sequence portion" refers to a partial structure of an oligonucleotide strand in a region having the aforementioned antisense sequence.

Furthermore, in the present description, an "antisense sequence" containing or not containing a nucleotide or oligonucleotide strand has the same meaning as the corresponding "antisense sequence portion" containing or not containing that nucleotide or that oligonucleotide strand. In addition, the "antisense sequence" has the same meaning as a base sequence of an "antisense sequence portion" containing or not containing the oligonucleotide strand and the like.

The aforementioned antisense sequence portion is not required to hybridize with the entire target RNA, but rather is only required to hybridize with at least a portion of the target RNA, and normally hybridizes with at least a portion of the target RNA. For example, expression of a target gene is controlled by an oligonucleotide having an antisense sequence complementary to the partial sequence of the target RNA (such as DNA, oligodeoxyribonucleotide or an oligonucleotide designed so as to normally demonstrated an antisense effect) hybridizing with at least a portion of the target RNA. In addition, although it is not necessary to hybridize with the entire antisense sequence portion and may not hybridize with a portion thereof, hybridization with the entire antisense sequence portion is preferable.

Complementarity between the aforementioned antisense sequence and partial sequence of target RNA is preferably 70% or more, more preferably 80% or more and even more preferably 90% or more (such as 95%, 96%, 97%, 98% or 99% or more). Although the sequences are not required to be completely complementary in order for the antisense sequence portion to hybridize with at least a portion of the target RNA, the sequences are more preferably completely complementary.

The aforementioned antisense sequence is preferably a sequence that contains "at least four contiguous nucleotides recognized by RNase H when hybridizing with target RNA", or a sequence "that contains at least one sugar-modified nucleotide but does not contain an oligonucleotide strand composed of four contiguous deoxyribonucleotides".

A person with ordinary skill in the art is able to easily determine a base sequence compatible with an antisense sequence "able to hybridize with target RNA" by using the BLAST program and the like. This applies similarly to a nucleotide sequence compatible with "at least four contiguous nucleotides recognized by RNase H when hybridizing with target RNA".

"At least four contiguous nucleotides recognized by RNase H when hybridizing with target RNA" are normally 4 to 30 contiguous nucleotides, preferably 4 to 20 contiguous nucleotides, more preferably 5 to 16 contiguous nucleotides, even more preferably 6 to 12 contiguous nucleotides, and particularly preferably 8 to 10 contiguous nucleotides. The aforementioned contiguous nucleotides are preferably independently selected from deoxyribonucleotides and sugar-modified nucleotides, and are more preferably independently selected from deoxyribonucleotides. The aforementioned contiguous nucleotides are particularly preferably 8 to 10 contiguous deoxyribonucleotides. These contiguous nucleotides may each be the same or different.

In addition, at least one of the contiguous nucleotides is preferably phosphorothioated from the viewpoint of superior pharmacokinetics. More preferably, at least one of the nucleotides on the 3'-end and 5'-end of these contiguous nucleotides is phosphorothioated. Even more preferably, 80% of these contiguous nucleotides are phosphorothioated, and still more preferably, 90% of these contiguous nucleotides are phosphorothioated. Particularly preferably, all of the contiguous nucleotides are phosphorothioated.

In the case the antisense sequence is a sequence that contains "at least four contiguous nucleotides recognized by RNase H when hybridizing with target RNA", 1 to 10 sugar-modified nucleotides are preferably bound adjacent to at least to the 3'-side and 5'-side of the "at least four contiguous nucleotides recognized by RNase H when hybridizing with target RNA" (antisense sequence portion) from the viewpoint of increasing affinity for a partial sequence of the target RNA or increasing resistance to nuclease, more preferably 1 to 7 sugar-modified nucleotides are bound adjacent to at least one of the 3'-side and 5'-side, and more preferably 2 to 3 sugar-modified nucleotides are bound adjacent to at least one of the 3'-side and 5'-side. Here, although one or a plurality of deoxyribonucleotides, ribonucleotides or both may be contained between a plurality of sugar-modified nucleotides at least on one of the 3'-side and 5'-side, the plurality of sugar-modified nucleotides are preferably contiguous. In addition, the one or a plurality of sugar-modified nucleotides are preferably bound adjacent to both the 3'-side and 5'-side of the aforementioned antisense sequence portion. In the case a plurality of sugar-modified nucleotides are bound adjacent to at least one of the 3'-side and 5'-side of the antisense sequence portion, "a plurality of sugar-modified nucleotides are bound adjacent to" refers to the plurality of sugar-modified nucleotides and an oligonucleotide strand composed of deoxyribonucleotides and ribonucleotides contained between the sugar-modified nucleotides bound adjacent to at least one of the 3'-side and 5'-side of the antisense sequence portion. In the case a plurality of sugar-modified nucleotides are bound adjacent to at least one of the 3'-side and 5'-side, each sugar-modified nucleotide may be the same or different.

Although a sugar-modified nucleotide portion bound adjacent to at least one of the 3'-side and 5'-side of the aforementioned "at least four contiguous nucleotides recognized by RNase H when hybridizing with target RNA" may or may not hybridize with the target RNA, the sugar-modified nucleotide portion preferably hybridizes with the target RNA from the same viewpoint as previous described.

In addition, preferably at least one sugar-modified nucleotide located at the 3'-side and 5'-side of the aforementioned "at least four contiguous nucleotides recognized by RNase H when hybridizing with target RNA" is phosphorothioated from the viewpoint of superior pharmacokinetics, more preferably at least one sugar-modified nucleotide located on the 3'-side and at least one sugar-modified nucleotide located on the 5'-side are phosphorothioated, even more preferably 50% are phosphorothioated, and still more preferably 80% are phosphorothioated. In addition, preferably all are phosphorothioated. In the case a plurality of sugar-modified nucleotides are located on the 3'-side, bonds between the nucleotides are preferably phosphorothioated, and this applies similarly to the case a plurality of sugar-modified nucleotides are located on the 5'-side.

At least a portion of "at least four contiguous nucleotides recognized by RNase H when hybridizing with target RNA" may or may not hybridize within a molecule. Sugar-modified nucleotides bound adjacent to at least one of the 3'-side and 5'-side of "at least four contiguous nucleotides recognized by RNase H when hybridizing with target RNA" also may or may not hybridize within a molecule.

In the case the antisense sequence is a sequence that "contains at least one sugar-modified nucleotide but does not contain an oligonucleotide strand composed of four contiguous deoxyribonucleotides", although the antisense sequence portion (mixmer) may or may not contain a ribonucleotide and may or may not contain a deoxyribonucleotide, it does contain at least one sugar-modified nucleotide, but does not contain an oligonucleotide strand composed of four contiguous deoxyribonucleotides. The antisense sequence portion is preferably a partial structure of an oligonucleotide composed of nucleotides independently selected from deoxyribonucleotides and sugar-modified nucleotides, and the content percentage of sugar-modified nucleotides is, for example, 25% or more. The content percentage of sugar-modified nucleotides is more preferably 30% or more and even more preferably 50% or more from the viewpoint of increasing affinity to a partial sequence of a target RNA or increasing resistance to nuclease. At least one of the nucleotide on the 3'-side and nucleotide on the 5'-side of this antisense sequence portion is preferably a sugar-modified nucleotide, and the nucleotide on the 3'-side and the nucleotide on the 5'-side are more preferably sugar-modified nucleotides from the same viewpoint.

In another aspect, the content percentage of sugar-modified nucleotides of the aforementioned antisense sequence portion is preferably 100%.

The antisense sequence portion that "contains at least one sugar-modified nucleotide but does not contain an oligonucleotide strand composed of four contiguous deoxyribonucleotides" more preferably does not contain an oligonucleotide strand composed of three contiguous deoxyribonucleotides.

The antisense sequence portion (mixmer) that "contains at least one sugar-modified nucleotide but does not contain an oligonucleotide strand composed of four contiguous deoxyribonucleotides" is normally 4 to 30 contiguous nucleotides, preferably 8 to 25 contiguous nucleotides, more preferably 10 to 20 contiguous nucleotides, even more preferably 14 to 16 contiguous nucleotides, and particularly preferably 15 contiguous nucleotides. These contiguous nucleotides may each by the same or different.

In addition, among the nucleotides composing the antisense sequence portion (mixmer) that "contains at least one sugar-modified nucleotide but does not contain an oligonucleotide strand composed of four contiguous deoxyribonucleotides", at least one of the nucleotides is preferably phosphorothioated. More preferably, at least one of the nucleotides on the 3'-end and 5'-end of the antisense sequence portion is phosphorothioated. Among the bonds between nucleotides contained in the antisense sequence portion, more preferably 80% are phosphorothioated, even more preferably 90% are phosphorothioated, and particularly preferably all are phosphorothioated.

Although at least a portion of the antisense sequence portion (mixmer) that "contains at least one sugar-modified nucleotide but does not contain an oligonucleotide strand composed of four contiguous deoxyribonucleotides" may hybridize within a molecule thereof, it preferably does not hybridize within a molecule thereof. Accordingly, the single-stranded oligonucleotide molecule preferably has the antisense sequence portion in the order of the antisense sequence portion (mixmer), a first nucleotide sequence portion, L and a second nucleotide sequence portion, and the number of nucleotides included by Y is set so that the antisense sequence portion does not hybridize within a molecule thereof, or preferably has an antisense sequence portion in the order of the first nucleotide sequence portion, L, the sequence nucleotide sequence portion and the antisense sequence portion (mixmer) and the number of nucleotides included by X (and X') is set so that the antisense sequence portion does not hybridize within a molecule thereof. The difference between the number of nucleotides contained in the single-strand oligonucleotide molecule from the 5'-end of L to 5'-end of the single-stranded oligonucleotide and the number of nucleotides contained in the single-stranded oligonucleotide molecule from the 3'-end of L to the 3'-end of the single-stranded oligonucleotide is preferably close to the number of nucleotides contained in the aforementioned antisense sequence portion, and the aforementioned difference is normally 6 to 30, preferably 8 to 25, more preferably 10 to 20, even more preferably 14 to 16 contiguous nucleotides, and particularly preferably 15 contiguous nucleotides.

One to ten sugar-modified nucleotides may be bound, although not required to be bound, adjacent to at least one of the 3'-side and 5'-side of the antisense sequence portion that "contains at least one sugar-modified nucleotide but does not contain an oligonucleotide strand composed of four contiguous deoxyribonucleotides". In this case, the sugar-modified nucleotides are applied in the same manner as in the case of the aforementioned sequence containing "four contiguous nucleotides recognized by RNase H when hybridizing to target RNA". Although they may or may not hybridize within a molecule thereof, they preferably do not hybridize within a molecule thereof.

Although the "sugar-modified nucleotide" contained in the antisense sequence portion is only required to be a nucleotide for which affinity to a partial sequence of target RNA has been increased or resistance to nuclease has been increased as a result of substitution and the like, it is preferably a 2'-O-methyl nucleotide, 2'-MOE (2'-O-methoxyethyl) nucleotide, 2'-AP (2'-O-aminopropyl) nucleotide, 2'-fluoronucleotide, 2'-F-arabinonucleotide (2'-F-ANA), bridged nucleotide (BNA (bridged nucleic acid)) or 2'-O-methylcarbamoylethyl nucleotide (MCE), and more preferably BNA or 2'-O-methyl nucleotide, even more preferably LNA containing a partial structure represented by the following formula (I) or 2'-O-methyl nucleotide, and particularly preferably LNA. This applies similarly to one or a plurality of sugar-modified nucleotides bound adjacent to the 3'-side of an antisense sequence portion as well as one or a plurality of sugar-modified nucleotides bound adjacent to the 5'-side of the antisense sequence portion.

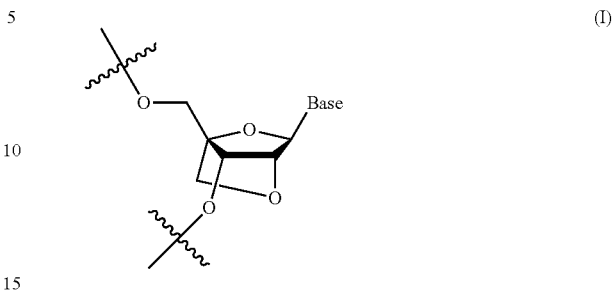

(I)

In the above formula, Base represents a base moiety and is a purin-9-yl group or 2-oxopyrimidin-1-yl group, and the purin-9-yl group and 2-oxopyrimidin-1-yl group may or may not be modified. Here, the 2-oxopyrimidin-1-yl group has the same meaning as a 2-oxo-1H-pyrimidin-1-yl group. In addition, the purin-9-yl group and the 2-oxopyrimidin-1-yl group respectively include tautomers thereof.

The types, numbers and locations of sugar-modified nucleotides, deoxyribonucleotides and ribonucleotides in the antisense sequence portion can have an effect on the antisense effect and the like demonstrated by the single-stranded oligonucleotide disclosed herein. Although the types, numbers and locations thereof are unable to be unconditionally defined since they differ according to the sequence and so forth of the target RNA, a person with ordinary skill in the art is able to determine a preferable aspect thereof while referring to the aforementioned descriptions in the literature relating to antisense methods. In addition, if the antisense effect demonstrated by the single-stranded oligonucleotide following modification of a base moiety, sugar moiety or phosphodiester bond moiety is measured and the resulting measured value is significantly lower than that of the single-stranded oligonucleotide prior to modification (such as if the measured value of the single-stranded oligonucleotide following modification is 30% or more of the measured value of the single-stranded oligonucleotide prior to modification), then that modification can be evaluated as a preferable aspect. As is indicated in, for example, the examples to be subsequently described, measurement of antisense effect can be carried out by introducing a test oligonucleotide into a cell and the like, and measuring the expression level of target RNA, expression level of cDNA associated with the target RNA or the amount of a protein associated with the target RNA, which is controlled by the antisense effect demonstrated by the test oligonucleotide using a known technique such as northern blotting, quantitative PCR or western blotting. This applies similarly to one or a plurality of sugar-modified nucleotides bound adjacent to the 3'-side of the antisense sequence portion, deoxyribonucleotides and ribonucleotides contained between the plurality of sugar-modified nucleotides, one or a plurality of sugar-modified nucleotides bound adjacent to the 5'-side of the antisense sequence portion, and deoxyribonucleotides and ribonucleotides contained between the plurality of sugar-modified nucleotides.

Two nucleotides at least on one of the 3'-side and 5'-side of the antisense sequence portion that "contains at least one sugar-modified nucleotide but does not contain an oligonucleotide strand composed of four contiguous deoxyribonucleotides" are preferably sugar-modified nucleotides, and the sugar-modified nucleotides are preferably bridged nucleotides and particularly preferably LNA. When two nucleotides on the 3'-side of the antisense sequence portion are sugar-modified nucleotides, two or more of the three nucleotides on the 5'-side are preferably sugar-modified nucleotides and are preferably coupled in any order indicated below in order starting from an end of the antisense sequence portion. When two nucleotides on the 5'-side of the antisense sequence portion are sugar-modified nucleotides, two of the three nucleotides on the 3'-side are preferably sugar-modified nucleotides and are preferably coupled in any order indicated below in order starting from an end of the antisense sequence portion. Furthermore, in the orders indicated below, the left side indicates the end side of the antisense sequence portion, while the right side indicates the inside of the antisense sequence portion. The sugar-modified nucleotide is preferably a bridged nucleotide and particularly preferably LNA.

Sugar-modified nucleotide-sugar-modified nucleotide-sugar-modified nucleotide

Sugar-modified nucleotide-sugar-modified nucleotide-deoxyribonucleotide

Sugar-modified nucleotide-deoxyribonucleotide-Sugar-modified nucleotide

In the case a single-stranded oligonucleotide contains a nucleotide sequence portion that hybridizes with the aforementioned antisense sequence portion within a molecule thereof, the type, number and modified location of the sugar-modified nucleotide, deoxyribonucleotide and ribonucleotide in the aforementioned "nucleotide sequence portion that hybridizes with an antisense sequence portion in a molecule thereof" may have an effect on the antisense effect and the like demonstrated by the single-stranded oligonucleotide. Although preferable aspects thereof are unable to be unconditionally defined since the they differ according to the types, sequences and the like of nucleotides targeted for modification, preferable aspects can be specified by measuring the antisense effects possessed by a single-strand oligonucleotide following modification in the same manner as the aforementioned antisense sequence portion. From the viewpoint of the "nucleotide sequence portion that hybridizes with an antisense sequence portion in a molecule thereof" being degraded by a nuclease such as RNase H in a specific cell resulting in the formation of an oligonucleotide containing an antisense sequence portion and facilitating the demonstration of an antisense effect, the "nucleotide sequence portion that hybridizes with an antisense sequence portion in a molecule thereof" preferably contains "at least four contiguous nucleotides cleaved by RNase H" and more preferably contains at least one ribonucleotide. In addition, the "nucleotide sequence portion that hybridizes with an antisense sequence portion in a molecule thereof" preferably contains an oligoribonucleotide and more preferably contains RNA. The coupled nucleotides are more preferably independently selected from ribonucleotides. In addition, the contiguous nucleotides are more preferably mutually coupled through phosphodiester bonds. These contiguous nucleotides may each be the same or different.

Complementarity between the aforementioned antisense sequence portion and the aforementioned "nucleotide sequence portion that hybridizes with an antisense sequence portion in a molecule thereof" is preferably 70% or more, more preferably 80% or more, and even more preferably 90% or more (such as 95%, 96%, 97%, 98% or 99%). Although these sequences are not required to be completely complementary in order for the antisense sequence portion and the "nucleotide sequence portion that hybridizes with an antisense sequence portion in a molecule thereof" to hybridize, they may be completely complementary. In addition, the entire "nucleotide sequence portion that hybridizes with an antisense sequence portion in a molecule thereof" is not required to hybridize with the antisense sequence portion, a portion may not hybridize or the entire sequence may hybridize.

The "nucleotide sequence portion that hybridizes with an antisense sequence portion in a molecule thereof" may partially hybridize with the antisense sequence portion, and the number of nucleotides that partially hybridize is normally selected corresponding to the stability of the structures that hybridize within a molecule thereof, the strength of the antisense effect on the aforementioned target RNA, costs, synthesis yield and other factors.

The following provides an explanation of X, X' and Y in the present invention. Although the present invention has several embodiments, an explanation is first provided of commonalities there between.

X represents a group derived from a first oligonucleotide composed of 7 to 100 nucleotides independently selected from deoxyribonucleotides, ribonucleotides and sugar-modified nucleotides, and the deoxyribonucleotides, ribonucleotides and sugar-modified nucleotides are either respectively and independently not modified or at least one of a sugar moiety, base moiety and phosphate moiety is modified. The first oligonucleotide contains at least one nucleotide of which at least one of the sugar moiety, base moiety and phosphate moiety has been modified. The first oligonucleotide has a nucleotide sequence X, and the nucleotide sequence X is able to hybridize with at least a portion of a second oligonucleotide and contains a first nucleotide sequence containing at least four contiguous nucleotides recognized by RNase H.

The nucleotide sequence X is a base sequence of nucleotides that compose the first oligonucleotide and contains the first nucleotide sequence. The first nucleotide sequence is a base sequence of nucleotides that compose a first nucleotide sequence portion.

The number of nucleotides contained in X is 7 to 100 and preferably 7 to 50. The number of nucleotides contained in X is normally selected corresponding to the strength of the antisense effect on the aforementioned target RNA, stability of the structure hybridized within a molecule thereof, costs, synthesis yield and other factors. The details thereof are subsequently described.

Y represents a group derived from a second oligonucleotide composed of 4 to 100 nucleotides independently selected from deoxyribonucleotides, ribonucleotides and sugar-modified nucleotides, and the deoxyribonucleotides, ribonucleotides and sugar-modified nucleotides are either respectively and independently not modified or at least one of a sugar moiety, base moiety and phosphate moiety is modified. The second oligonucleotide has a nucleotide sequence Y, and the nucleotide sequence Y is able to hybridize with at least a portion of the aforementioned first oligonucleotide and contains a second nucleotide sequence containing at least one ribonucleotide.

The nucleotide sequence Y is a base sequence of nucleotides that compose the second oligonucleotide and contains a second nucleotide sequence. The second nucleotide sequence is a base sequence of nucleotides that compose a second nucleotide sequence portion.

The number of nucleotides contained in Y is 4 to 100 and preferably 4 to 50. The number of nucleotides contained in Y may be the same or different as the number of nucleotides contained in X. The number of nucleotides contained in Y is normally selected corresponding to the strength of the antisense effect on the aforementioned target RNA, stability of the structure hybridized within a molecule thereof, costs, synthesis yield and other factors. Details thereof are subsequently described.

X and Y hybridize within a molecule by the first nucleotide sequence portion and second nucleotide sequence portion.

Although the first nucleotide sequence and the second nucleotide sequence are not required to be completely complementary in order for the first nucleotide sequence portion and the second nucleotide sequence portion to hybridize, complementarity is preferably 70% or more, more preferably 80% or more and even more preferably 90% or more (such as 95%, 96%, 97%, 98% or 99%). The first nucleotide sequence and the second nucleotide sequence may also be completely complementary.

Although the nucleotide sequence X and the nucleotide sequence Y are not required to be completely complementary in order for X and Y to hybridize, complementarity is preferably 70% or more, more preferably 80% or more and even more preferably 90% or more (such as 95%, 96%, 97%, 98% or 99%). Nucleotide sequence X and nucleotide sequence Y may also be completely complementary.

The first nucleotide sequence preferably contains 4 to 25 contiguous nucleotides and more preferably contains 8 to 20 contiguous nucleotides. In order for the first oligonucleotide to be recognized by RNase H in a cell, the first nucleotide sequence is preferably a sequence independently selected from deoxyribonucleotides and sugar-modified nucleotides, and is more preferably a sequence of contiguous deoxyribonucleotides. These contiguous nucleotides may each be the same or different.

In addition, from the viewpoint of superior pharmacokinetics, at least one nucleotide of the first nucleotide sequence portion is preferably phosphorothioated. More preferably, at least one nucleotide of the 3'-side and 5'-side of the first nucleotide sequence portion is phosphorothioated. Even more preferably, 80% of the nucleotides of the first nucleotide sequence portion are phosphorothioated, and still more preferably 90% of the nucleotides are phosphorothioated. Nucleotides contained in the first nucleotide sequence portion are particularly preferably mutually coupled through phosphorothioate bonds. A more detailed description thereof is subsequently described.

The second nucleotide sequence preferably contains at least four contiguous nucleotides cleaved by RNase H, more preferably contains 4 to 25 contiguous nucleotides, and even more preferably contains 8 to 22 contiguous nucleotides. These contiguous nucleotides may each be the same or different. The second nucleotide sequence portion preferably contains an oligoribonucleotide and more preferably contains RNA in order for the second nucleotide sequence portion to be cleaved by RNase H within cells. Nucleotides contained in the second nucleotide sequence portion are particularly preferably mutually coupled through phosphodiester bonds. A more detailed description is subsequently described.

At least one of nucleotide sequence X and nucleotide sequence Y contains an antisense sequence capable of hybridizing with at least a portion of a target RNA.

X' is a group derived from a fourth oligonucleotide composed of 7 to 100 nucleotides independently selected from deoxyribonucleotides, ribonucleotides and sugar-modified nucleotides, and the deoxyribonucleotides, ribonucleotides and sugar-modified nucleotides are either respectively and independently not modified or at least one sugar moiety, base moiety and phosphate moiety is modified. The fourth oligonucleotide contains at least one nucleotide of which at least one of a sugar moiety, base moiety and phosphate moiety has been modified. The fourth oligonucleotide has the nucleotide sequence X' and the nucleotide sequence X' contains a fourth nucleotide sequence that is an antisense sequence capable of hybridizing with a target RNA.

The nucleotide sequence X' is a base sequence of nucleotides that compose the fourth oligonucleotide and contains a fourth nucleotide sequence. The fourth nucleotide sequence is a base sequence of nucleotides that compose a fourth nucleotide sequence portion.

The number of nucleotides contained in X' is 7 to 100, the lower limit thereof is preferably 8, more preferably 10, even more preferably 12 and still more preferably 13. The upper limit of the number of nucleotides contained in X' is preferably 50, more preferably 35, even more preferably 25 and sill more preferably 20. The number of nucleotides contained in X' is preferably 10 to 50, more preferably 10 to 35, even more preferably 12 to 25, still more preferably 13 to 20 and particularly preferably 14 to 15. The number of nucleotides contained in X' is normally selected corresponding to the strength of the antisense effect on the aforementioned target RNA, stability of the structure hybridized within a molecule thereof, costs, synthesis yield and other factors.

The type, number and modified location of sugar-modified nucleotides, deoxyribonucleotides and ribonucleotides in X may have an effect on the antisense effect demonstrated by the single-stranded oligonucleotide. Although preferable aspects thereof are unable to be unconditionally defined since they differ according to the types, sequences and the like of nucleotides targeted for modification, preferable aspects can be specified by measuring the antisense effects possessed by a single-strand oligonucleotide following modification in the same manner as the aforementioned antisense sequence portion. This applies similarly to Y and X'.

In the case two or more of X', Y and X hybridize with the same target RNA, the antisense sequences possessed thereby may each be the same or different. X', Y and X may each separately hybridize with different target RNA.

In the case nucleotide sequence X has an antisense sequence, the antisense sequence preferably either contains "at least four contiguous nucleotides recognized by RNase H when hybridizing with target RNA" or "contains at least one sugar-modified nucleotide but does not contain an oligonucleotide strand composed of four contiguous deoxyribonucleotides", and more preferably contains "at least four contiguous nucleotides recognized by RNase H when hybridizing with target RNA". In the case the first nucleotide sequence is an antisense sequence, the antisense sequence is a sequence that contains "at least four contiguous nucleotides recognized by RNase H when hybridizing with target RNA".

In the case nucleotide sequence Y has an antisense sequence, the antisense sequence either preferably contains "at least four contiguous nucleotides recognized by RNase H when hybridizing with target RNA" or "contains at least one sugar-modified nucleotide but does not contain an oligonucleotide strand composed of four contiguous deoxyribonucleotides", and more preferably contains "at least four contiguous nucleotides recognized by RNase H when hybridizing with target RNA". This applies similarly to the case of nucleotide sequence X' containing an antisense sequence.

In the case the aforementioned antisense sequence portion hybridizes within a molecule thereof in the manner described below, the antisense sequence portion preferably contains "at least four contiguous nucleotides recognized by RNase H when hybridizing with target RNA" from the viewpoint of facilitating the formation of an oligonucleotide containing an antisense sequence portion and demonstrating an antisense effect as a result of the antisense sequence portion being recognized by a nuclease such as RNase H within a specific cell and a "nucleotide sequence portion that hybridizes with the antisense sequence portion within a molecule thereof" being degraded.

In the case nucleotide sequence X has an antisense sequence, Y may contain a "nucleotide sequence portion that hybridizes with the antisense sequence portion within a molecule thereof" (eighth nucleotide sequence portion). In the case the first nucleotide sequence is an antisense sequence, the antisense sequence portion (first nucleotide sequence portion) hybridizes with the second nucleotide sequence portion.

In the case nucleotide sequence X' has an antisense sequence, Y may contain a "nucleotide sequence portion that hybridizes with the antisense sequence portion within a molecule thereof" (sixth nucleotide sequence portion).

In the case nucleotide sequence Y has an antisense sequence, X may contain a "nucleotide sequence portion that hybridizes with the antisense sequence portion within a molecule thereof" (seventh nucleotide sequence portion).

Next, explanations are respectively provided of [A] the case of nucleotide sequence X containing an antisense sequence, and the case of nucleotide sequence Y containing an antisense sequence as described in section [B] to be subsequently described.

[A] Case of Nucleotide Sequence X Containing Antisense Sequence

In the case nucleotide sequence X contains an antisense sequence, the first nucleotide sequence is preferably an antisense sequence. In addition, in another aspect thereof, the aforementioned X preferably has the first nucleotide sequence portion between the aforementioned antisense sequence portion and L. Although the following provides an explanation in a given order, embodiments of the present invention are not limited thereto, but rather, for example, the first nucleotide sequence may partially overlap the aforementioned antisense sequence.

[A-1] Case in which First Nucleotide Sequence is Antisense Sequence

In the case the first nucleotide sequence is an antisense sequence, the aforementioned antisense sequence in the form of the first nucleotide sequence is a sequence that contains "at least four contiguous nucleotides recognized by RNase H when hybridizing with target RNA". Preferable aspects of the aforementioned first nucleotide sequence and first nucleotide sequence portion are the same as a sequence containing "at least four contiguous nucleotides recognized by RNase H when hybridizing with target RNA" as described regarding the antisense sequence and antisense sequence portion. In addition, 1 to 10 sugar-modified nucleotides are preferably bound adjacent to at least one of the 3'-side and 5'-side of the first nucleotide sequence portion, and this one or a plurality of sugar-modified nucleotides are the same as one or a plurality of sugar-modified nucleotides adjacent to at least one of the 3'-side and 5'-side of "at least four contiguous nucleotides recognized by RNase H when hybridizing with target RNA" (antisense sequence portion).

In addition, in the case the single-stranded oligonucleotide contains a partial structure in the form of X'-L-X, the aforementioned fourth nucleotide sequence that is an antisense sequence contained by nucleotide sequence X' is preferably either a sequence containing "at least four contiguous nucleotides recognized by RNase H when hybridizing with target RNA" or a sequence that "contains at least one sugar-modified nucleotide but does not contain an oligonucleotide strand composed of four contiguous deoxyribonucleotides", and is more preferably a sequence containing "at least four contiguous nucleotides recognized by RNase H when hybridizing with target RNA". Preferred embodiments of the antisense sequence contained by the aforementioned nucleotide sequence X' are the same as previously described with respect to the antisense sequence and the antisense sequence portion, and the one or a plurality of sugar-modified nucleotides bound adjacent to the 3'-side of the antisense sequence portion and the one or a plurality of sugar-modified nucleotides bound adjacent to the 5'-side of the antisense sequence portion are the same as above.

In addition to the characteristics previously described as commonalities, the first nucleotide sequence preferably contains 4 to 20 contiguous nucleotides, more preferably contains 5 to 16 contiguous nucleotides, even more preferably contains 6 to 12 contiguous nucleotides, still more preferably contains 8 to 10 contiguous nucleotides, and particularly preferably contains 8 to 10 contiguous deoxyribonucleotides.

In a certain aspect, the lower limit of the number of nucleotides contained in X is preferably 8, more preferably 10, even more preferably 12, and still more preferably 13. The upper limit of the number of nucleotides contained in X is preferably 50, more preferably 35, even more preferably 25, and still more preferably 20. The number of nucleotides contained in X is preferably 10 to 50, more preferably 10 to 35, even more preferably 12 to 25, still more preferably 13 to 20, and particularly preferably 13 to 15.

In a certain aspect, the difference between the number of nucleotides contained in Y and the number of nucleotides contained in X is preferably within 10, more preferably within 5, even more preferably within 4, still more preferably within 2, and particularly preferably 0.

In addition, in the case the single-stranded oligonucleotide contains a partial structure in the form of X'-L'-X, in a certain aspect, the difference between the number of nucleotides contained in Y and the number of nucleotides contained in X is preferably within 10, more preferably within 5, even more preferably within 4, still more preferably within 2 and particularly preferably 0. The number of nucleotides contained in X' is as previously explained as a commonality.

In the case the single-stranded oligonucleotide contains a partial structure in the form of X'-L'-X, in a different aspect thereof, the difference between the number of nucleotides contained in X'-L'-X and the number of nucleotides contained in Y is preferably within 10, more preferably within 5, even more preferably within 4, still more preferably within 2, and particularly preferably 0. The number of nucleotides contained in X' is as previously described as a commonality.

In addition, in this case, Y may further contain a sixth nucleotide sequence containing at least one ribonucleotide that is able to hybridize with the fourth nucleotide sequence portion in addition to the second nucleotide sequence portion, and may further contain a tenth nucleotide sequence capable of hybridizing with a group derived from a fifth oligonucleotide in the form of L'. Namely, Y may have the second nucleotide sequence portion and the sixth nucleotide sequence portion coupled in that order, or may have the second nucleotide sequence portion, the tenth nucleotide sequence portion and the sixth nucleotide sequence portion coupled in that order. Preferable aspects of the sixth nucleotide sequence are the same as the second nucleotide sequence subsequently described. Preferable aspects of the tenth nucleotide sequence portion are the same as the subsequently described L'.

In addition, in this case, as will be subsequently described, although at least one of the 5'-side and 3'-side of the second nucleotide sequence portion may be coupled to the adjacent nucleotide through a phosphorothioate bond, in this case, it is preferably coupled through a phosphodiester bond. Although one or a plurality of sugar-modified nucleotides may be bound adjacent to at least one of the 5'-side and 3'-side of the second nucleotide sequence, sugar-modified nucleotides are preferably not bound in this case. At least one of the 5'-side and 3'-side of the sixth nucleotide sequence portion is preferably coupled to an adjacent nucleotide through a phosphorothioate bond, and aspects thereof are the same as in the case of the second nucleotide sequence to be subsequently described. One or a plurality of sugar-modified nucleotides are preferably bound adjacent to at least one of the 5'-side and 3'-side of the sixth nucleotide sequence portion, and aspects thereof are the same as the case of the second nucleotide sequence to be subsequently described.

In addition to the aforementioned commonalities, the second nucleotide sequence preferably contains 4 to 20 contiguous nucleotides, more preferably contains 5 to 16 contiguous nucleotides, even more preferably contains 6 to 12 contiguous nucleotides, still more preferably contains 8 to 12 contiguous nucleotides and particularly preferably contains 10 to 12 contiguous nucleotides.

From the viewpoint of facilitating the demonstration of an antisense effect by forming an oligonucleotide that is at least a portion of the first oligonucleotide and contains the aforementioned antisense sequence portion as a result of degradation by RNA nucleases such as RNase A being suppressed until the single-stranded oligonucleotide is delivered to the nucleus of a specific cell along with group derived from the second oligonucleotide being degraded by nucleases such as RNase H in a specific cell, at least one of the 5'-side and the 3'-side of the second nucleotide sequence portion is preferably coupled to an adjacent nucleotide through a phosphorothioate bond. In the case Y bonds to L on the 5'-side, the 3'-side of the second nucleotide sequence portion is more preferably coupled to an adjacent nucleotide through a phosphorothioate bond, while in the case Y bonds to L on the 3'-side, the 5'-side of the second nucleotide sequence portion is more preferably coupled to an adjacent nucleotide through a phosphorothioate bond. In addition, from the viewpoint of suppressing degradation by enzymes such as RNA nucleases, 5 to 10 sugar-modified nucleotides are preferably bound adjacent to at least one of the 5'-side and 3'-side of the second nucleotide sequence portion. In the case Y bonds to L on the 5'-side, 1 to 7 sugar-modified nucleotides are more preferably bound adjacent to the 3'-side of the second nucleotide sequence portion, and 2 or 3 sugar-modified nucleotides are even more preferably bound. In the case Y bonds to L on the 3'-side, 1 to 7 sugar-modified nucleotides are more preferably bound adjacent to the 5'-side of the second nucleotide sequence portion, and 2 or 3 sugar-modified nucleotides are even more preferably bound. Here, although a plurality of deoxyribonucleotides, ribonucleotides or both may be contained between the plurality of sugar-modified nucleotides on at least one of the 3'-side and 5'-side, the plurality of sugar-modified nucleotides are preferably contiguous. In the case a plurality of sugar-modified nucleotides are bound adjacent to at least one of the 3'-side and 5'-side of the second nucleotide sequence portion, "a plurality of sugar-modified nucleotides are bound adjacent to" refers to the plurality of sugar-modified nucleotides and an oligonucleotide strand composed of deoxyribonucleotides and ribonucleotides contained between the sugar-modified nucleotides being bound adjacent to". In the case a plurality of sugar-modified nucleotides are bound adjacent to at least one of the 3'-side and 5'-side of the second nucleotide sequence portion, each sugar-modified nucleotide may be the same or different.

Although the sugar-modified nucleotide portion bound adjacent to at least one of the 3'-side and 5'-side of the aforementioned second nucleotide sequence portion may or may not hybridize with a portion of the first oligonucleotide, it preferably hybridizes with a portion of the first oligonucleotide.

The sugar-modified nucleotide bound adjacent to at least one of the 5'-side and 3'-side of the aforementioned second nucleotide sequence portion is preferably a 2'-O-methyl nucleotide, 2'-MOE (2'-O-methoxyethyl) nucleotide, 2'-AP (2'-O-aminopropyl) nucleotide, 2'-fluoronucleotide, 2'-F-arabinonucleotide (2'-F-ANA), bridged nucleotide (BNA (bridged nucleic acid)) or 2'-O-methylcarbamoylethyl nucleotide (MCE), and more preferably BNA or 2'-O-methyl nucleotide, even more preferably LNA containing a partial structure represented by the following formula (I) or 2'-O-methyl nucleotide, and particularly preferably a 2'-O-methyl nucleotide.

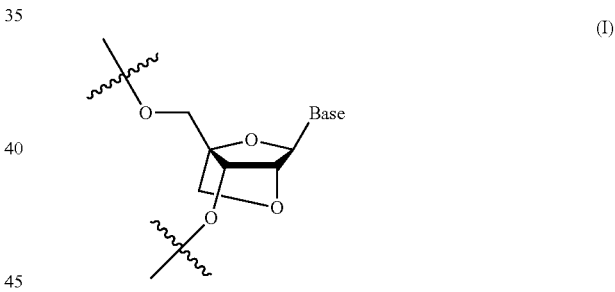

(I)

In the above formula, Base represents a base moiety and is a purin-9-yl group or 2-oxopyrimidin-1-yl group, and the purin-9-yl group and 2-oxopyrimidin-1-yl group may or may not be modified.

Although the number of nucleotides of the oligonucleotide adjacent to at least one of the 5'-side and 3'-side of the second nucleotide sequence portion may be the same or different as the number of nucleotides adjacent to at least one of the 5'-side and 3'-side of the first nucleotide sequence portion (such as an antisense sequence portion hybridized by the second nucleotide sequence portion), that difference is preferably within 3, more preferably within 1, and there is particularly preferably no difference there between. In the case an oligonucleotide strand containing one or a plurality of the aforementioned sugar-modified nucleotides bonds adjacent to the 3'-side of the second nucleotide sequence portion, although the number of nucleotides of that oligonucleotide strand may be the same or different as the number of nucleotides of an oligonucleotide strand containing one or a plurality of sugar-modified nucleotides bound adjacent to the 5'-side of the first nucleotide sequence portion, that difference is preferably within 3, more preferably within 1, and there is particularly preferably no difference there between. In the case an oligonucleotide strand containing one or a plurality of the aforementioned sugar-modified nucleotides bonds adjacent to the 5'-side of the second nucleotide sequence portion, although the number of nucleotides of the oligonucleotide strand may be the same or different as the number of nucleotides of an oligonucleotide strand containing one or a plurality of sugar-modified nucleotides bound adjacent to the 3'-side of the first nucleotide sequence portion, that difference is preferably within 3, more preferably within 1 and there is particularly preferably no difference.

As another aspect thereof, in the case the nucleotide sequence Y contains an antisense sequence, the aforementioned Y preferably has a second nucleotide sequence portion between the aforementioned antisense sequence portion and L. The sequence of the aforementioned antisense sequence portion is the same as the antisense sequence contained by nucleotide sequence Y in the case the nucleotide sequence Y contains an antisense sequence as described in section [B] to be subsequently described.

In the case nucleotide sequence Y contains an antisense sequence, the second nucleotide sequence is similar to the second nucleotide sequence previously described as a commonality in addition to the second nucleotide sequence in the case the nucleotide sequence Y contains an antisense sequence as described in section [B] to be subsequently described. In the case the first nucleotide sequence is an antisense sequence and the nucleotide sequence Y contains an antisense sequence, the second nucleotide sequence preferably contains 4 to 25 contiguous nucleotides, more preferably contains 10 to 25 contiguous nucleotides, even more preferably contains 12 to 22 contiguous nucleotides, and particularly preferably contains 12 to 18 contiguous nucleotides.

In an aspect of a nucleotide bound adjacent to the second nucleotide sequence portion, bonding with that nucleotide is similar to the case the nucleotide sequence Y of [B] to be subsequently described contains an antisense sequence.

In the case the nucleotide sequence Y contains an antisense sequence, in a certain aspect thereof, the number of nucleotides contained in X is preferably 10 to 35, more preferably 12 to 25, even more preferably 12 to 16, and particularly preferably 14 to 15.

The number of nucleotides contained in Y is preferably larger than the number of nucleotides contained in X by about the same number of nucleotides contained in an "antisense sequence portion contained by Y". The difference between the number of nucleotides contained in Y and the number of nucleotides contained in X is preferably 6 to 30, more preferably 8 to 25, even more preferably 10 to 20 and still more preferably 13 to 15.

In the case nucleotide sequence Y contains an antisense sequence, in another aspect thereof, the number of nucleotides contained in X is preferably 20 to 40, more preferably 24 to 38, even more preferably 26 to 38, still more preferably 28 to 33, and even more preferably still 30 to 32.

In this case, the difference between the number of nucleotides contained in Y and the number of nucleotides contained in X is preferably within 10, more preferably within 5, even more preferably within 4, still more preferably within 2, and particularly preferably 0.

In this case, nucleotide sequence X may further contain a seventh nucleotide sequence that is capable of hybridizing with an antisense sequence portion contained by Y and contains at least one ribonucleotide. In the case nucleotide sequence X contains the seventh nucleotide sequence, the single-stranded oligonucleotide represented by the aforementioned X-L-Y has a seventh nucleotide sequence portion, a first nucleotide sequence portion, L, a second nucleotide sequence portion and an antisense sequence portion contained by Y in that order.

Preferable aspects of the aforementioned seventh nucleotide sequence portion are similar to the aforementioned "nucleotide sequence portion that hybridizes with an antisense sequence portion in a molecule thereof". Among these, the seventh nucleotide sequence preferably contains 10 to 20 nucleotides, more preferably contains 12 to 19 nucleotides, and even more preferably contains 13 to 15 nucleotides.

From the viewpoint of facilitating the demonstration of an antisense effect by forming an oligonucleotide that is at least a portion of the first oligonucleotide and contains the aforementioned antisense sequence portion, and further forming an oligonucleotide that is at least a portion of the second oligonucleotide and contains the aforementioned antisense sequence portion contained by Y as a result of degradation by RNA nucleases such as RNase A being suppressed until the single-stranded oligonucleotide is delivered to the nucleus of a specific cell along with group derived from the second oligonucleotide being degraded by nucleases such as RNase H in a specific cell, at least one of the 5'-side and the 3'-side of the seventh nucleotide sequence portion is preferably coupled to an adjacent nucleotide through a phosphorothioate bond. In the case X bonds to L on the 5'-side, the 3'-side of the seventh nucleotide sequence portion is more preferably coupled to an adjacent nucleotide through a phosphorothioate bond, while in the case X bonds to L on the 3'-side, the 5'-side of the seventh nucleotide sequence portion is more preferably coupled to an adjacent nucleotide through a phosphorothioate bond. In addition, from the viewpoint of suppressing degradation by enzymes such as RNA nucleases, 1 to 10 sugar-modified nucleotides are preferably bound adjacent to at least one of the 5'-side and 3'-side of the seventh nucleotide sequence portion. In the case X bonds to L on the 5'-side, 1 to 7 sugar-modified nucleotides are more preferably bound adjacent to the 3'-side of the seventh nucleotide sequence portion, and 2 or 3 sugar-modified nucleotides are even more preferably bound. In the case X bonds to L on the 3'-side, 1 to 7 sugar-modified nucleotides are more preferably bound adjacent to the 5'-side of the seventh nucleotide sequence portion, and 2 or 3 sugar-modified nucleotides are even more preferably bound. Here, although a plurality of deoxyribonucleotides, ribonucleotides or both may be contained between the plurality of sugar-modified nucleotides on at least one of the 3'-side and 5'-side, the plurality of sugar-modified nucleotides are preferably contiguous. In the case a plurality of sugar-modified nucleotides are bound adjacent to at least one of the 3'-side and 5'-side of the seventh nucleotide sequence portion, "a plurality of sugar-modified nucleotides are bound adjacent to" refers to the plurality of sugar-modified nucleotides and an oligonucleotide strand composed of deoxyribonucleotides and ribonucleotides contained between the sugar-modified nucleotides being bound adjacent to". In the case a plurality of sugar-modified nucleotides are bound adjacent to at least one of the 3'-side and 5'-side of the seventh nucleotide sequence portion, each sugar-modified nucleotide may be the same or different.

Although the sugar-modified nucleotide portion bound adjacent to at least one of the 3'-side and 5'-side of the aforementioned seventh nucleotide sequence portion may or may not hybridize with a portion of the second oligonucleotide, it preferably hybridizes with a portion of the second oligonucleotide.

Although the number of nucleotides of the oligonucleotide adjacent to at least one of the 5'-side and 3'-side of the seventh nucleotide sequence portion may be the same or different from the number of nucleotides of the oligonucleotide adjacent to at least one of the 5'-side and 3'-side of the antisense sequence portion contained by the aforementioned Y, that difference is preferably within 3, more preferably within 1, and is particularly preferably the same. In the case an oligonucleotide strand containing the aforementioned one or a plurality of nucleotides bound adjacent to the 3'-side of the seventh nucleotide sequence portion, although the number of nucleotides thereof may be the same or different from the number of nucleotides of the oligonucleotide strand containing one or a plurality of sugar-modified nucleotides bound adjacent to the 5'-side of the antisense sequence portion contained by Y, that difference is preferably within 3, more preferably within 1, and particularly preferably the same. In the case an oligonucleotide strand containing the aforementioned one or a plurality of sugar-modified nucleotides is bound to the 5'-side of the seventh nucleotide sequence portion, although the number of nucleotides of that oligonucleotide strand may be the same or different from the number of nucleotides of the oligonucleotide strand containing one or a plurality of sugar-modified nucleotides bound adjacent to the 3'-side of the antisense sequence portion contained by Y, that difference is preferably within 3, more preferably within 1, and particularly preferably the same.

The aspect of a sugar-modified nucleotide portion bound adjacent to at least one of the 3'-side and 5'-side of the aforementioned seventh nucleotide sequence portion is similar to a sugar-modified nucleotide portion bound adjacent to at least one of the 3'-side and 5'-side of the aforementioned second nucleotide sequence portion.

[A-2] Case in which X has First Nucleotide Sequence Portion Between Aforementioned Antisense Sequence Portion and L Although the first nucleotide sequence portion and the aforementioned antisense sequence portion may be bound directly or may be bound indirectly with an oligonucleotide interposed there between, they are preferably bound indirectly containing an oligonucleotide.

Although the antisense sequence may be a sequence that contains "at least four contiguous nucleotides recognized by RNase H when hybridizing with target RNA", or a sequence "that contains at least one sugar-modified nucleotide but does not contain an oligonucleotide strand composed of four contiguous deoxyribonucleotides", the antisense sequence is preferably a sequence that contains "at least four contiguous nucleotides recognized by RNase H when hybridizing with target RNA". A preferable aspect and so forth of the sequence is similar to that in the explanation of the aforementioned antisense sequence and antisense sequence portion, and similar to one or a plurality of sugar-modified nucleotides bound adjacent to the 3'-side of an antisense sequence portion as well as one or a plurality of sugar-modified nucleotides bound adjacent to the 5'-side of an antisense sequence portion.

In the case the antisense sequence is a sequence that contains "at least four contiguous nucleotides recognized by RNase H when hybridizing with target RNA", and the first nucleotide sequence portion and the aforementioned antisense sequence portion are bound indirectly with an oligonucleotide interposed there between, the oligonucleotide preferably contains one or a plurality of sugar-modified nucleotides bound adjacent to at least one of the 3'-side and 5'-side of the aforementioned antisense sequence portion. Aspects of the sugar-modified nucleotides are as previously described. In addition, the oligonucleotide preferably further includes an oligonucleotide that is degraded under physiological conditions. An aspect of an oligonucleotide that is degraded under physiological conditions is similar to L' to be subsequently described. Accordingly, the first oligonucleotide preferably has the first nucleotide sequence portion, a group derived from the aforementioned oligonucleotide that is degraded under physiological conditions, the aforementioned one or a plurality of sugar-modified nucleotides, an antisense sequence portion contained by the aforementioned X, and the aforementioned one or a plurality of sugar-modified nucleotides in that order.

In the case the antisense sequence is a sequence "that contains at least one sugar-modified nucleotide but does not contain an oligonucleotide strand composed of four contiguous deoxyribonucleotides", and the first nucleotide sequence portion and the antisense sequence portion contained by X are bound indirectly with an oligonucleotide interposed there between, the oligonucleotide is preferably an oligonucleotide that is degraded under physiological conditions. An aspect of an oligonucleotide that is degraded under physiological conditions is similar to L' to be subsequently described.

In addition, in the case the single-stranded oligonucleotide contains a partial structure in the form of X'-L'-X, the antisense sequence contained by nucleotide sequence X' in the form of the fourth nucleotide sequence is similar to the fourth nucleotide sequence described in section [A-1].

In addition to the previously described commonalities, the first nucleotide sequence preferably contains 8 to 17 contiguous nucleotides therefrom and more preferably contains 8 to 10 contiguous nucleotides.

In addition to the previously described commonalities, the second nucleotide sequence preferably contains 4 to 20 contiguous nucleotides therefrom, more preferably contains 8 to 19 contiguous nucleotides, and even more preferably contains 9 to 11 contiguous nucleotides.

A sugar-modified nucleotide portion bound adjacent to at least one of the 3'-side and 5'-side of the aforementioned second nucleotide sequence portion is similar to a sugar-modified nucleotide portion bound adjacent to at least one of the 3'-side and 5'-side of the second nucleotide sequence described in detail in the aforementioned section [A-1].

The number of nucleotides contained in X is preferably 10 to 50, more preferably 20 to 40, even more preferably 20 to 30, still more preferably 22 to 28, and particularly preferably 25 to 28.

In a certain embodiment, the number of nucleotides contained in Y is preferably 4 to 25, more preferably 8 to 20, even more preferably 10 to 20, and particularly preferably 10 to 16.

In this case, the number of nucleotides contained in X is larger than the number of nucleotides contained in Y, and the difference there between is preferably near the number of nucleotides contained by the aforementioned antisense sequence portion, preferably 6 to 30, more preferably 8 to 25, even more preferably 10 to 20, and still more preferably 12 to 15.

In addition, in a different embodiment, the number of nucleotides contained in Y is preferably 10 to 50, more preferably 20 to 40, even more preferably 20 to 30, still preferably 22 to 28, and particularly preferably 25 to 28.

In this case, the difference between the number of nucleotides contained in Y and the number of nucleotides contained in X is preferably within 10, more preferably within 5, even more preferably within 4, still more preferably within 2, and particularly preferably 0.

In this case, in addition to the second nucleotide sequence portion, Y may further contain an eighth nucleotide sequence portion that is capable of hybridizing with an antisense sequence portion possessed by the aforementioned X and contains at least one ribonucleotide, and may further contain a ninth nucleotide sequence portion capable of hybridizing with an oligonucleotide that couples the first nucleotide sequence portion and the aforementioned antisense sequence portion possessed by X. Namely, Y may have the second nucleotide sequence portion and the eighth nucleotide sequence portion coupled in this order, or may have the second nucleotide sequence portion, the ninth nucleotide sequence portion, and the eighth nucleotide sequence portion coupled in this order.

A preferable aspect of the aforementioned eighth nucleotide sequence portion is similar to the aforementioned "nucleotide sequence portion that hybridizes with the antisense sequence portion within a molecule thereof", and similar to the aforementioned second nucleotide sequence portion.

An aspect of a sugar-modified nucleotide portion bound adjacent to at least one of the 3'-side and 5'-side of the aforementioned eighth nucleotide sequence portion is similar to a sugar-modified nucleotide portion bound adjacent to at least one of the 3'-side and 5'-side of the second nucleotide sequence portion. Although a sugar-modified nucleotide portion bound adjacent to at least one of the 3'-side and 5'-side of the eighth nucleotide sequence portion may or may not hybridize with a portion of the first oligonucleotide, it preferably hybridizes with a portion of the first oligonucleotide. Although the number of nucleotides of an oligonucleotide strand containing one or a plurality of sugar-modified nucleotides adjacent to at least one of the 5'-side and 3'-side of the eighth nucleotide sequence portion may be the same as or different from the number of nucleotides of an oligonucleotide strand containing one or a plurality of sugar-modified nucleotides adjacent to at least one of the 5'-side and 3'-side of the aforementioned antisense sequence portion contained by X, the difference there between is preferably within 3, more preferably within 1, and are particularly preferably the same. In the case the aforementioned oligonucleotide strand containing one or a plurality of sugar-modified nucleotides is bound adjacent to the 3'-side of the eighth nucleotide sequence portion, although the number of nucleotides thereof may be the same as or different from the number of nucleotides of the aforementioned oligonucleotide strand containing one or a plurality of sugar-modified nucleotides bound adjacent to the 5'-side of the aforementioned antisense sequence portion contained by X, the difference there between is preferably within 3, more preferably within 1, and are particularly preferably the same. In the case the aforementioned oligonucleotide strand containing one or a plurality of sugar-modified nucleotides is bound adjacent to the 5'-side of the eighth nucleotide sequence portion, although the number of nucleotides thereof may be the same as or different from the number of nucleotides of the oligonucleotide strand containing one or a plurality of sugar-modified nucleotides bound adjacent to the 3'-side of the aforementioned antisense sequence portion contained by X, the difference there between is preferably within 3, more preferably within 1, and are particularly preferably the same.

In this case, although at least one of the 5'-side and 3'-side of the second nucleotide sequence portion may be coupled to an adjacent nucleotide through a phosphorothioate bond, it is preferably coupled through a phosphodiester bond. In addition, although one or a plurality of sugar-modified nucleotides may be bound adjacent to at least one of the 5'-side and 3'-side of the second nucleotide sequence portion, it is preferably not bound.

A preferable aspect of a ninth nucleotide sequence portion is similar to L' to be subsequently described.

In addition, in the case the single-stranded oligonucleotide contains a partial structure in the form of X'-L'-X, the difference between the number of nucleotides contained in Y and the number of nucleotides contained in X in a certain embodiment is preferably within 10, more preferably within 5, even more preferably within 4, still more preferably within 2, and particularly preferably 0.

In the case the single-stranded oligonucleotide contains a partial structure in the form of X'-L'-X, the difference between the number of nucleotides contained in X'-L'-X and the number of nucleotides contained in Y in another embodiment is preferably within 10, more preferably within 5, even more preferably within 4, still more preferably within 2, and particularly preferably 0.

In addition, in this case, in addition to the second nucleotide sequence portion, Y may further contain a sixth nucleotide sequence portion that is capable of hybridizing with the fourth nucleotide sequence portion and contains at least one ribonucleotide, and may further contain a tenth nucleotide sequence portion capable of hybridizing with a group derived from the fifth oligonucleotide in the form of L'. Namely, Y may have the second nucleotide sequence portion, the eighth nucleotide sequence portion and the sixth nucleotide sequence portion coupled in this order, may have the second nucleotide sequence portion, the eight nucleotide sequence portion, the tenth nucleotide sequence portion and the sixth nucleotide sequence portion coupled in this order, may have the second nucleotide sequence portion, the ninth nucleotide sequence portion, the eighth nucleotide sequence portion and the sixth nucleotide sequence portion coupled in this order, or may have the second nucleotide sequence portion, the ninth nucleotide sequence portion, the eighth nucleotide sequence portion, the tenth nucleotide sequence portion and the sixth nucleotide sequence portion coupled in this order. The sixth nucleotide sequence is similar to the sixth nucleotide sequence described in the aforementioned section [A-1]. The eighth nucleotide sequence and the ninth nucleotide sequence are as previously described.

In addition, in this case, although at least one of the 5'-side and 3'-side of the second nucleotide sequence portion may be coupled to an adjacent nucleotide through a phosphorothioate bond, in this case, it is preferably coupled through a phosphodiester bond. Although one or a plurality of sugar-modified nucleotides may be bound adjacent to at least one of the 5'-side and 3'-side of the second nucleotide sequence portion, in this case, it is preferably not bound. Similarly, although at least one of the 5'-side and 3'-side of the eighth nucleotide sequence portion may be coupled to an adjacent nucleotide through a phosphorothioate bond, in this case it is preferably coupled through a phosphodiester bond. Although one or a plurality of sugar-modified nucleotides may be bound adjacent to at least one of the 5'-side and 3'-side of the eighth nucleotide sequence portion, in this case it is preferably not bound. At least one of the 5'-side and 3'-side of the sixth nucleotide sequence portion is preferably coupled to an adjacent nucleotide through a phosphorothioate bond, and an aspect thereof is similar to the case of the second nucleotide sequence described in detailed in the aforementioned section [A-1]. One or a plurality of sugar-modified nucleotides are preferably bound adjacent to at least one of the 5'-side and 3'-side of the sixth nucleotide sequence portion, and an aspect thereof is similar to the case of the second nucleotide sequence described in detail in the aforementioned section [A-1].

Moreover, in the case nucleotide sequence Y contains an antisense sequence, the aforementioned Y preferably has the second nucleotide sequence portion between the aforementioned antisense sequence portion and L, and the aforementioned antisense sequence portion is similar to the case of the nucleotide sequence Y containing an antisense sequence as described in section [B] to be subsequently described.

In this case, an aspect of the second nucleotide sequence portion is similar to the aspect of the second nucleotide sequence portion in the case the nucleotide sequence Y further contains an antisense sequence as described in section [A-1]. An aspect of a nucleotide bound adjacent to the second nucleotide sequence portion and bonding with that nucleotide are similar to the case the nucleotide sequence Y of [B] to be subsequently described contains an antisense sequence.

In this case, nucleotide sequence X may further contain a seventh nucleotide sequence that is able to hybridize with an antisense sequence portion contained by Y and contains at least one ribonucleotide.

In this case, in a certain aspect, the single-stranded oligonucleotide represented by the formula X-L-Y may have an antisense sequence portion contained by X, a seventh nucleotide sequence portion, a first nucleotide sequence portion, L, a second nucleotide sequence portion and an antisense sequence portion contained by Y in this order, or may further have the aforementioned ninth nucleotide sequence portion and the aforementioned eighth nucleotide sequence portion in this order.

In another aspect, a single-stranded oligonucleotide represented by the formula X-L-Y may have a seventh nucleotide sequence portion, an antisense sequence portion contained by X, a first nucleotide sequence portion, L, a second nucleotide sequence portion, the aforementioned ninth nucleotide sequence portion, the aforementioned eighth nucleotide sequence portion, and an antisense sequence portion contained by Y in this order.

[B] Case of Nucleotide Sequence Y Containing Antisense Sequence

The aforementioned Y preferably has a second nucleotide sequence portion between the aforementioned antisense sequence portion and L. The second nucleotide sequence portion and the aforementioned antisense sequence portion may be bound directly or may be bound indirectly with an oligonucleotide interposed there between.

The antisense sequence is preferably a sequence that contains "at least four contiguous nucleotides recognized by RNase H when hybridizing with target RNA", or a sequence "that contains at least one sugar-modified nucleotide but does not contain an oligonucleotide strand composed of four contiguous deoxyribonucleotides", and the antisense sequence is more preferably a sequence that contains "at least four contiguous nucleotides recognized by RNase H when hybridizing with target RNA". A preferable aspect of the sequence is similar to the explanation of the aforementioned antisense sequence and antisense sequence portion, and one or a plurality of sugar-modified nucleotides bound adjacent to the 3'-side of an antisense sequence portion and one or a plurality of sugar-modified nucleotides bound adjacent to the 5'-side of an antisense sequence portion are similar to the above.

In the case the antisense sequence is a sequence that contains "at least four contiguous nucleotides recognized by RNase H when hybridizing with target RNA", the second nucleotide sequence portion and the aforementioned antisense sequence portion are preferably bound indirectly with an oligonucleotide interposed there between. The oligonucleotide is preferably one or a plurality of sugar-modified nucleotides bound adjacent to at least one of the 3'-side and 5'-side of the aforementioned antisense sequence portion, and aspects thereof are as previously described.

In the case the antisense sequence is a sequence "that contains at least one sugar-modified nucleotide but does not contain an oligonucleotide strand composed of four contiguous deoxyribonucleotides", although the second nucleotide sequence portion and the aforementioned antisense sequence portion may be bound directly or may be bound indirectly with an oligonucleotide interposed there between, they are preferably bound directly. In the case they are bound indirectly with an oligonucleotide interposed there between, the oligonucleotide is similar to L' to be subsequently described.

From the viewpoint of facilitating the demonstration of an antisense effect by forming an oligonucleotide that is a portion of the second oligonucleotide and contains the aforementioned antisense sequence portion as a result of degradation by RNA nucleases such as RNase A being suppressed until the single-stranded oligonucleotide is delivered to the nucleus of a specific cell along with the second nucleotide sequence portion being degraded by RNase H in a specific cell, the 5'-side and the 3'-side of the second nucleotide sequence portion are preferably coupled to adjacent nucleotides through phosphodiester bonds.

In addition, at least one sugar-modified nucleotide is preferably bound adjacent to at least one of the 5'-side and 3'-side of the second nucleotide sequence portion. In the case Y is bound to L on the 5'-side, at least one sugar-modified nucleotide is more preferably bound adjacent to the 3'-side of the second nucleotide sequence portion, and in the case Y is bound to L on the 3'-side, at least one sugar-modified nucleotide is more preferably bound adjacent to the 5'-side of the second nucleotide sequence portion.

In the case the antisense sequence contains "at least four contiguous nucleotides recognized by RNase H when hybridizing with target RNA", the sugar-modified nucleotide is preferably one or a plurality of sugar-modified nucleotides bound adjacent to at least one of the 3'-side and 5'-side of the antisense sequence portion, and aspects thereof are similar to that previously described.

In the case the antisense sequence "contains at least one sugar-modified nucleotide but does not contain an oligonucleotide strand composed of four contiguous deoxyribonucleotides", the sugar-modified nucleotide is preferably one sugar-modified nucleotide on the 3'-side or 5'-side of the antisense sequence portion, and aspects thereof are similar to that previously described.

In addition to aspects of the second nucleotide sequence described in the previously described commonalities, the second nucleotide sequence preferably contains 4 to 25 contiguous nucleotides, more preferably contains 10 to 22 contiguous nucleotides, even more preferably contains 10 to 16 contiguous nucleotides, still more preferably contains 12 to 14 contiguous nucleotides, and particularly preferably contains 12 to 13 contiguous nucleotides.

Similar to that previously described, from the viewpoint of facilitating the demonstration of an antisense effect by forming an oligonucleotide that is at least a portion of the second oligonucleotide and contains the aforementioned antisense sequence portion as a result of degradation by RNA nucleases such as RNase A being suppressed until the first single-stranded oligonucleotide is delivered to the nucleus of a specific cell along with a group derived from the second oligonucleotide being degraded by RNase H in a specific cell, at least one of the 5'-side and the 3'-side of the first nucleotide sequence portion is preferably coupled to an adjacent nucleotide through a phosphorothioate bond. In the case X is bound to L on the 5'-side, the 3'-side of the first nucleotide sequence portion is more preferably coupled to an adjacent nucleotide through a phosphorothioate bond, and in the case X is bound to L on the 3'-side, the 5'-side of the first nucleotide sequence portion is more preferably coupled to an adjacent nucleotide through a phosphorothioate bond. In a certain embodiment, nucleotides contained in the first oligonucleotide are mutually coupled through phosphorothioate bonds.

In addition, from the viewpoint of inhibiting degradation by enzymes such as RNA nucleases, 1 to 10 sugar-modified nucleotides are preferably bound adjacent to at least one of the 5'-side and 3'-side of the first nucleotide sequence portion. In the case X bonds to L on the 5'-side, 1 to 7 sugar-modified nucleotides are more preferably bound adjacent to the 3'-side of the first nucleotide sequence portion, and 2 or 3 sugar-modified nucleotides are even more preferably bound. In the case X bonds to L on the 3'-side, 1 to 7 sugar-modified nucleotides are more preferably bound adjacent to the 5'-side of the first nucleotide sequence portion, and 2 or 3 sugar-modified nucleotides are even more preferably bound. Here, although a plurality of deoxyribonucleotides, ribonucleotides or both may be contained between the plurality of sugar-modified nucleotides on at least one of the 3'-side and 5'-side, the plurality of sugar-modified nucleotides are preferably contiguous. In the case a plurality of sugar-modified nucleotides are bound adjacent to at least one of the 3'-side and 5'-side of the first nucleotide sequence portion, "a plurality of sugar-modified nucleotides are bound adjacent to" refers to the plurality of sugar-modified nucleotides and an oligonucleotide strand composed of deoxyribonucleotides and ribonucleotides contained among the sugar-modified nucleotides being bound adjacent to. In the case a plurality of sugar-modified nucleotides are bound adjacent to at least one of the 3'-side and 5'-side of the first nucleotide sequence portion, each of the sugar-modified nucleotides may be the same or different.

Although the aforementioned sugar-modified nucleotide portion bound adjacent to at least one of the 3'-side and 5'-side of the first nucleotide sequence portion may or may not hybridize with a portion of the second oligonucleotide, it preferably hybridizes with a portion of the second oligonucleotide.

The aforementioned sugar-modified nucleotide portion bound adjacent to at least one of the 3'-side and 5'-side of the first nucleotide sequence portion is similar to the sugar-modified nucleotide portion bound adjacent to at least one of the 3'-side and 5'-side of the second nucleotide sequence previously described in detail in the aforementioned section [A-1].

Aspects of the first nucleotide sequence are similar to the first nucleotide sequence described in the aforementioned commonalities, and include 4 to 20 contiguous nucleotides, preferably 6 to 16 contiguous nucleotides, more preferably 8 to 12 contiguous nucleotides, and particularly preferably 9 to 11 contiguous deoxyribonucleotides.

In a certain embodiment, the number of nucleotides contained in X is preferably 7 to 50, more preferably 8 to 30, even more preferably 10 to 20, and particularly preferably 10 to 16.

In this case, the number of nucleotides contained in X is smaller than the number of nucleotides contained in Y, and the difference there between is preferably 6 to 30, more preferably 8 to 25, even more preferably 10 to 20, and particularly preferably 13 to 15. Nucleotide sequence X may further contain a seventh nucleotide sequence that is able to hybridize with an antisense sequence portion contained by Y and contains at least one ribonucleotide. In this case, in a certain embodiment, a single-stranded oligonucleotide represented by the formula X-L-Y may have a seventh nucleotide sequence portion, a first nucleotide sequence portion, L, and second nucleotide sequence portion and an antisense sequence portion contained by Y in this order.

Aspects of the seventh nucleotide sequence are as previously described in section [A-1].

In this case, the number of nucleotides contained in X is preferably 10 to 50, more preferably 20 to 45, even more preferably 25 to 40, still more preferably 26 to 38, and particularly preferably 28 to 33.

The difference between the number of nucleotides contained in Y and the number of nucleotides contained in X is preferably within 10, more preferably within 5, even more preferably within 4, still more preferably within 2, and particularly preferably 0.

Nucleotide sequence X may further contain an antisense sequence, and aspects in this case are as explained in sections [A-1] and [A-2].

In addition, in the case the single-stranded oligonucleotide contains a partial structure in the form of X'-L'-X, the aforementioned fourth nucleotide sequence contained by nucleotide sequence X' is similar to the fourth nucleotide sequence described in section [A-1].

Next, an explanation is provided of L, L' and a functional molecule. The following are common to the aforementioned several aspects.

L is a group derived from an oligonucleotide that is degraded under physiological conditions and is a linker that links the previously described X and Y. L links the aforementioned X and Y in the order of X-L-Y.

L' is a group derived from an oligonucleotide that is degraded under physiological conditions, and is a linker that links the aforementioned X and X'. L' links the aforementioned X and X' in the order of X'-L'-X.

L and X are preferably coupled through a covalent bond, and for example, sugar moieties of each of the terminal nucleotides of L and X (including partial structures in which sugar moieties have been substituted from the sugar backbone in the case of sugar-modified nucleotides) are preferably coupled through a phosphodiester bond. L and Y are preferably coupled through a covalent bond, and for example, sugar moieties of each of the terminal nucleotides of L and Y (including partial structures in which sugar moieties have been substituted from the sugar backbone in the case of sugar-modified nucleotides) are preferably coupled through a phosphodiester bond. Similarly, a second nucleotide sequence portion in Y and L are preferably coupled through a phosphodiester bond. Similarly, L' and X' are preferably coupled through a phosphodiester bond, and L' and X are preferably coupled through a phosphodiester bond.

Here, a "group derived from an oligonucleotide that is degraded under physiological conditions" is only required to be a group derived from an oligonucleotide that is degraded by various enzymes such as DNases (deoxyribonucleases) or RNases (ribonucleases) under physiological conditions, and a base moiety, sugar moiety or phosphate bond may or may not be chemically modified in all or a portion of the nucleotides that compose the oligonucleotide.

L is preferably more rapidly degraded than the previously described antisense sequence portion. L is a preferably a group derived from an oligonucleotide coupled through a phosphodiester bond, more preferably a group derived from an oligodeoxyribonucleotide or oligoribonucleotide, and even more preferably a group derived from DNA or RNA. L' is similar to L.

Although L may or may not contain a sequence partially complementary to the group derived from an oligonucleotide of L, L is preferably a group derived from an oligonucleotide that does not contain a sequence partially complementary to the group derived from an oligonucleotide of L. Examples of groups derived from such oligonucleotides include (N)n coupled through phosphodiester bonds (wherein, N respectively and independently represents an adenosine, uridine, cytidine, guanosine, 2'-deoxyadenosine, thymidine, 2'-deoxycytidine and 2'-deoxyguanosine, and n represents an integer (number of repeats) of 1 to 40). Among these, n is preferably 3 to 20, more preferably 4 to 10, even more preferably 4 to 7, still more preferably 4 or 5, and particularly preferably 4. L' is similar to L. In another aspect of L', n is preferably 2 to 5 and more preferably 2 to 4.

L' may have the same sequence as L or may have a different sequence.

A functional molecule may be bound directly or indirectly to the first oligonucleotide, second oligonucleotide, third oligonucleotide, fourth oligonucleotide or fifth oligonucleotide. In the case the first oligonucleotide contains an antisense sequence portion, the functional molecule is preferably bound to the second oligonucleotide. Although the functional molecule and second oligonucleotide may be bound directly or indirectly through another substance, the second oligonucleotide and functional molecule are preferably bound by covalent bonding, ionic bonding or hydrogen bonding. From the viewpoint of high bond stability, the second oligonucleotide and functional molecule are preferably bound directly with covalent bonds or are more preferably bound with covalent bonds through a linker (linking group). In the case the second oligonucleotide contains an antisense sequence portion, the functional molecule is preferably bound to the first oligonucleotide. Bonding between the functional molecule and first oligonucleotide is the same as bonding between the functional molecule and second oligonucleotide.

In the case the first oligonucleotide and second oligonucleotide each have an antisense sequence portion and when the second oligonucleotide contains the antisense sequence portion farthest from L, the functional molecule is preferably bound to the first oligonucleotide, and when the first oligonucleotide contains the antisense sequence portion farthest from L, the functional molecule is preferably bound to the second oligonucleotide. Bonding between the functional molecule and first oligonucleotide or second oligonucleotide is the same as previously described. In the case the fourth oligonucleotide contains an antisense sequence portion, the functional molecule is preferably bound to the second oligonucleotide. Bonding between the functional molecule and second oligonucleotide is the same as previously described.

In the case the aforementioned functional molecule is bound to a single-stranded oligonucleotide by covalent bonds, the aforementioned functional molecule is preferably bound directly or indirectly to the 3'-end or 5'-end of the single-stranded oligonucleotide molecule. Bonding between the aforementioned linker or functional molecule and a terminal nucleotide of the single-stranded oligonucleotide molecule is selected according to the functional molecule.

The aforementioned linker or functional molecule and the terminal nucleotide of the single-stranded oligonucleotide molecule are preferably coupled through a phosphodiester bond or modified phosphodiester bond and more preferably coupled through a phosphodiester bond. In a certain embodiment, a terminal nucleotide of the second oligonucleotide and the aforementioned linker or functional molecule are preferably coupled through a phosphodiester bond or modified phosphodiester bond, and more preferably coupled through a phosphodiester bond. In a certain embodiment, a terminal nucleotide of the first oligonucleotide and the aforementioned linker or functional molecule are preferably coupled through a phosphodiester bond or modified phosphodiester bond and are preferably coupled through a phosphodiester bond.

The aforementioned linker or functional molecule may be directly coupled to an oxygen atom at the 3'-position possessed by the nucleotide on the 3'-end of the single-stranded oligonucleotide molecule, or may be directly coupled to an oxygen atom at the 5'-position possessed by the nucleotide on the 5'-end.

There are no particular limitations on the structure of the "functional molecule", and a desired function is imparted to the single-stranded nucleotide as a result of bonding therewith. Examples of desired functions include a labeling function, purifying function and delivery function to a target site. Examples of molecules that impart a labeling function include fluorescent proteins and compounds such as luciferase. Examples of molecules that impart a purifying function include compounds such as biotin, avidin, His-tag peptide, GST-tag peptide or FLAG-tag peptide.

In addition, from the viewpoint of efficiently delivering a single-stranded oligonucleotide to a target site (such as a target cell) with high specificity and extremely effectively suppressing expression of a target gene with that single-stranded oligonucleotide, a molecule having a function that causes the single-stranded oligonucleotide to be delivered to a target site is preferably bound as a functional molecule. Publications such as the European Journal of Pharmaceuticals and Biopharmaceutics, Vol. 107, pp. 321-340 (2016), Advanced Drug Delivery Reviews, Vol. 104, pp. 78-92 (2016), or Expert Opinion on Drug Delivery, Vol. 11, pp. 791-822 (2014) can be referred to regarding molecules having such a delivery function.

Examples of molecules that impart a delivery function to target RNA include lipids and sugars from the viewpoint of, for example, being able to efficiently deliver a single-stranded oligonucleotide to the liver and the like with high specificity. Examples of such lipids include cholesterol, fatty acids, fat-soluble vitamins such as vitamin E (tocopherols, tocotrienols), vitamin A, vitamin D or vitamin K, intermediate metabolites such as acylcarnitine or acyl CoA, glycolipids, glycerides and derivatives thereof. Among these, cholesterol and vitamin E (tocopherols, tocotrienols) are preferable from the viewpoint of higher safety. Among these, tocopherols are more preferable, tocopherol is even more preferable, and α-tocopherol is particularly preferable. Examples of sugars include sugar derivatives that interact with asialoglycoprotein receptors.

"Asialoglycoprotein receptors" are present on the surface of liver cells and have an action that recognizes a galactose radical of an asialoglycoprotein and incorporates molecules thereof into the cell where they are degraded. "Sugar derivatives that interact with asialoglycoprotein receptors" are preferably compounds that have a structure that resembles a galactose residue and are incorporated into cells due to interaction with asialoglycoprotein receptors, and examples thereof include GalNac (N-acetylgalactosamine) derivatives, galactose derivatives and lactose derivatives. In addition, from the viewpoint of being able to efficiently deliver the single-stranded oligonucleotide of the present invention to the brain with high specificity, examples of "functional molecules" include sugars (such as glucose or sucrose). In addition, from the viewpoint of being able to efficiently deliver the single-stranded oligonucleotide to various organs with high specificity by interacting with various proteins on the cell surface of those organs, examples of "functional molecules" include receptor ligands, antibodies, and peptides or proteins of fragments thereof.

Since the linker used to intermediate bonding between a functional molecule and the first oligonucleotide, second oligonucleotide, third oligonucleotide, fourth oligonucleotide or fifth oligonucleotide is only required to be able to demonstrate the function possessed by the functional molecule as a single-stranded oligonucleotide, there are no particular limitations on the linker provided it stably bonds the functional molecule and the oligonucleotide. Although examples of the linker include groups derived from oligonucleotides having 2 to 20 nucleotides, groups derived from polypeptides having 2 to 20 amino acids, alkylene groups having 2 to 20 carbon atoms and alkenylene groups having 2 to 20 carbon atoms, the linker is preferably a C2-20 alkylene group or C2-20 alkenylene group (wherein, methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—). Here, the linker may also contain a group represented by —C(O)—O—, —O—C(O)—NR$^1$— (wherein, R$^1$ represents a hydrogen atom, C1-6 alkyl group or halo-C1-6 alkyl group), —C(O)—NR$^1$— (wherein, R$^1$ represents a hydrogen atom, C1-6 alkyl group or halo-C1-6 alkyl group), —C(S)—NR$^1$— (wherein, R$^1$ represents a hydrogen atom, C1-6 alkyl group or halo-C1-6 alkyl group) or NR$^1$—C(O)—NR$^1$ (wherein, R$^1$ respectively and independently represents a hydrogen atom, C1-6 alkyl group or halo-C1-6 alkyl group) by combining the aforementioned substitutions and replacements.

More preferably, the linker is a C2-20 alkylene group (wherein, methylene groups of the alkylene group are respectively and independently not-replaced or replaced with —O—, and or not-replaced methylene groups are respectively and independently unsubstituted or substituted with a hydroxyl group or protected hydroxyl group), even more preferably a C8-12 alkylene group (wherein, methylene groups of the alkylene group are respectively and independently not-replaced or replaced with —O—, and not-replaced methylene groups are respectively and independently unsubstituted or substituted with a hydroxyl group), and particularly preferably a 1,8-octylene group. In addition, as another aspect thereof, the linker is particularly preferably a group represented by the following formula (III).

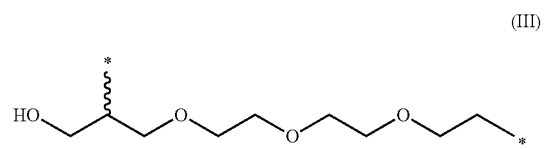

(III)

In the above formula, one asterisk (*) represents a bonding site with a group derived from an oligonucleotide (atom that composes a nucleotide), while the other asterisk (*) represents a bonding site with a group derived from a functional molecule (atom that composes a group derived from a functional molecule).

As another aspect thereof, the linker is more preferably a C2-20 alkylene group (wherein methylene groups of the alkylene group are respectively and independently not-replaced or replaced with —O— or —NR$^B$— (wherein R$^B$ represents a hydrogen atom or C1-6 alkyl group), and not-replaced methylene groups respectively and independently are unsubstituted or substituted with an oxo group), even more preferably a group represented by the formula —N(H)C(O)—(CH$_2$)$_e$—N(H)C(O)—(CH$_2$)$_e$—C(O)— (wherein, e respectively and independently represents an integer of 1 to 6), and particularly preferably a group represented by the formula

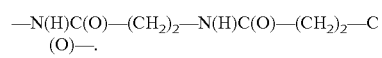

There are no particular limitations on the protective group of the aforementioned "protected hydroxyl group" since it is only required to be stable during bonding between a functional molecule and oligonucleotide. Examples thereof include arbitrary protective groups described in, for example, Protective Groups in Organic Synthesis, 3rd edition, published by John Wiley & Sons (1999). Specific examples thereof include a methyl group, benzyl group, p-methoxybenzyl group, tert-butyl group, methoxymethyl group, methoxyethyl group, 2-tetrahydropyranyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, trimethylsilyl group, triethylsilyl group, triisopropylsilyl group, tert-butyldimethylsilyl group, [(triisopropylsilyl)oxy]methyl (Tom) group, 1-(4-chlorophenyl)-4-ethoxypiperidin-4-yl (Cpep) group, triphenylmethyl (trityl) group, monomethoxytrityl group, dimethoxytrityl (DMTr) group, trimethoxytrityl group, 9-phenylxanthen-9-yl (Pixyl) group and 9-(p-methoxyphenyl)xanthen-9-yl (MOX) group. The protective group of the "protected hydroxyl group" is preferably a benzoyl group, trimethylsilyl group, triethylsilyl group, triisopropylsilyl group, tert-butyldimethylsilyl group, triphenylmethyl (trityl) group, monomethoxytrityl group, dimethoxytrityl group, trimethoxytrityl group, 9-phenylxanthen-9-yl group or 9-(p-methoxyphenyl)xanthen-9-yl group, more preferably a monomethoxytrityl group, dimethoxytrityl group or trimethoxytrityl group, and even more preferably a dimethoxytrityl group.

The following lists examples of preferable single-stranded oligonucleotides used in nucleic acid pharmaceuticals.

1) A single-stranded oligonucleotide represented by the formula:

X-L-Y (wherein, X represents a group derived from a first oligonucleotide composed of 7 to 100 nucleotides that are independently selected from a deoxyribonucleotide, ribonucleotide and sugar-modified nucleotide and that contains at least one nucleotide of which at least one of a sugar moiety, base moiety and phosphate moiety has been modified, Y represents a group derived from a second oligonucleotide composed of 4 to 100 nucleotides that are independently selected from a deoxyribonucleotide, ribonucleotide and sugar-modified nucleotide, and L represents a group derived from a third oligonucleotide that respectively covalently bonds with the first oligonucleotide and the second oligonucleotide at both ends thereof and is degraded under physiological conditions, and the third oligonucleotide contains a phosphodiester bond; wherein, the first oligonucleotide has a nucleotide sequence X, and the second oligonucleotide has a nucleotide sequence Y, the nucleotide sequence X contains a first nucleotide sequence that is capable of hybridizing with at least a portion of the second oligonucleotide and contains at least four contiguous nucleotides recognized by RNase H, the nucleotide sequence Y contains a second nucleotide sequence that is capable of hybridizing with at least a portion of the first oligonucleotide and contains at least one ribonucleotide, at least one of the nucleotide sequence X and the nucleotide sequence Y contains at least one antisense sequence capable of hybridizing with a target RNA, and in the case of having two or more antisense sequences, the target RNA hybridized by each antisense sequence may be the same or different), wherein X and Y hybridize by the first nucleotide sequence portion and the second nucleotide sequence portion.

2) The single-stranded oligonucleotide described in 1), wherein X bonds to L on the 3'-side and Y bonds to L on the 5'-side.

3) The single-stranded oligonucleotide described in 1), wherein X bonds to L on the 5'-side and Y bonds to L on the 3'-side.

4) The single-stranded oligonucleotide described in any of 1) to 3), wherein complementarity between the antisense sequence and target RNA sequence is 70% or more.

5) The single-stranded oligonucleotide described in any of 1) to 4), wherein complementarity between the first nucleotide sequence and the second nucleotide sequence is 70% or more.

6) The single-stranded oligonucleotide described in any of 1) to 5), wherein nucleotides contained in the single-stranded oligonucleotide represented by the formula X-L-Y are mutually coupled through at least one type of bond respectively and independently selected from the group consisting of a phosphodiester bond, phosphorothioate bond, methyl phosphonate bond, methyl thiophosphonate bond, phosphorodithioate bond and phosphoroamidate bond.

7) The single-stranded oligonucleotide described in any of 1) to 6), wherein each nucleotide contained in the single-stranded oligonucleotide represented by formula X-L-Y is mutually coupled through at least one type of bond respectively and independently selected from the group consisting of a phosphodiester bond and phosphorothioate bond.

8) The single-stranded oligonucleotide described in any of 1) to 7), wherein nucleotides contained in the third oligonucleotide are mutually coupled through phosphodiester bonds.

9) The single-stranded oligonucleotide described in any of 1) to 8), wherein the third oligonucleotide is composed of 3 to 10 nucleotides independently selected from the group consisting of deoxyribonucleotides and ribonucleotides.

10) The single-stranded oligonucleotide described in any of 1) to 9), wherein the third oligonucleotide is composed of 4 to 7 nucleotides independently selected from the group consisting of deoxyribonucleotides and ribonucleotides.

11) The single-stranded oligonucleotide described in any of 1) to 10), wherein the third oligonucleotide is an oligodeoxyribonucleotide or oligoribonucleotide.

12) The single-stranded oligonucleotide described in 1) to 11), wherein the third oligonucleotide is DNA or RNA.

13) The single-stranded oligonucleotide described in any of 1) to 12), wherein the third oligonucleotide is RNA.

14) The single-stranded oligonucleotide described in any of 1) to 13), wherein the first oligonucleotide contains a sugar-modified nucleotide bound adjacent to at least one of the 5'-side and 3'-side of the first nucleotide sequence portion.

15) The single-stranded oligonucleotide described in any of 1) to 14), wherein the first oligonucleotide contains a phosphorothioate bond.

16) The single-stranded oligonucleotide described in any of 1) to 15), wherein the first nucleotide sequence is a sequence containing nucleotides mutually coupled through a phosphorothioate bond.

17) The single-stranded oligonucleotide described in any of 1) to 16), wherein the first nucleotide sequence is a sequence composed of 4 to 20 nucleotides including at least one deoxyribonucleotide.

18) The single-stranded oligonucleotide described in any of 1) to 17), wherein the first nucleotide sequence is a sequence composed of 4 to 20 deoxyribonucleotides.

19) The single-stranded oligonucleotide described in any of 1) to 18), wherein the second nucleotide sequence is a sequence containing at least four contiguous nucleotides cleaved by RNase H.

20) The single-stranded oligonucleotide described in any of 1) to 19), wherein the second nucleotide sequence is a sequence composed of 4 to 25 ribonucleotides.

21) The single-stranded oligonucleotide described in any of 1) to 20), wherein the second oligonucleotide contains sugar-modified nucleotides bound adjacent to at least one of the 5'-side and 3'-side of the second nucleotide sequence portion.

22) The single-stranded oligonucleotide described in any of 1) to 21), wherein the second oligonucleotide contains a phosphodiester bond.

23) The single-stranded oligonucleotide described in any of 1) to 22), wherein at least one of the 5'-side and 3'-side of the second nucleotide sequence portion is coupled to an adjacent nucleotide through a phosphodiester bond.

24) The single-stranded oligonucleotide described in any of 1) to 23), wherein the second nucleotide sequence is a sequence containing nucleotides mutually coupled through a phosphodiester bond.

25) The single-stranded oligonucleotide described in any of 1) to 24), wherein X contains at least one sugar-modified nucleotide and the nucleotide sequence X contains at least one antisense sequence.

26) The single-stranded oligonucleotide described in 25), wherein the first nucleotide sequence is the antisense sequence.

27) The single-stranded oligonucleotide described in 25) or 26), wherein the first nucleotide sequence is a sequence containing at least four contiguous nucleotides recognized by RNase H when hybridizing with a target RNA.

28) The single-stranded oligonucleotide described in any of 25) to 27), wherein the first oligonucleotide contains a sugar-modified nucleotide bound adjacent to at least one of the 5'-side and 3'-side of the first nucleotide sequence portion.

29) The single-stranded oligonucleotide described in any of 25) to 28), wherein nucleotides contained in the first oligonucleotide are mutually coupled through phosphorothioate bonds.

30) The single-stranded oligonucleotide described in any of 25) to 29), wherein the second nucleotide sequence is a sequence composed of 4 to 20 ribonucleotides.

31) The single-stranded oligonucleotide described in any of 25) to 30), wherein at least one the 5'-side and 3'-side of the second nucleotide sequence portion is coupled to an adjacent nucleotide through a phosphorothioate bond.

32) The single-stranded oligonucleotide described in 25), wherein the X has the first nucleotide sequence portion between the antisense sequence portion and L.

33) The single-stranded oligonucleotide described in 32), wherein the X contains an oligonucleotide that is degraded under physiological conditions between the first nucleotide sequence portion and the antisense sequence portion.

34) The single-stranded oligonucleotide described in 33), wherein the oligonucleotide contained by the X that is degraded under physiological conditions is composed of 2 to 10 nucleotides independently selected from the group consisting of deoxyribonucleotides and ribonucleotides.

35) The single-stranded oligonucleotide described in 33) or 34), wherein nucleotides contained in the oligonucleotide contained by the X that is degraded under physiological conditions are mutually coupled through phosphodiester bonds.

36) The single-stranded oligonucleotide described in any of 33) to 35), wherein the oligonucleotide contained by the X that is degraded under physiological conditions is DNA or RNA composed of 2 to 7 nucleotides.

37) The single-stranded oligonucleotide described in any of 32) to 36), wherein the antisense sequence portion contained by the X contains a phosphorothioate bond.

38) The single-stranded oligonucleotide described in any of 32) to 37), wherein the antisense sequence contained by the nucleotide sequence X is a sequence containing nucleotides mutually coupled through a phosphorothioate bond.

39) The single-stranded oligonucleotide described in any of 32) to 38), wherein the first oligonucleotide contains a sugar-modified nucleotide bound adjacent to at least one of the 5'-side and 3'-side of the antisense sequence portion contained by the X.

40) The single-stranded oligonucleotide described in any of 32) to 39), wherein the first oligonucleotide contains sugar-modified nucleotides bound adjacent to the 5'-side and 3'-side of the antisense sequence portion contained by the X.

41) The single-stranded oligonucleotide described in 39) or 40), wherein a sugar-modified nucleotide bound adjacent to at least one of the 5'-side and 3'-side of the antisense sequence portion contained by the X is coupled to at least one of the 5'-side and 3'-side of the antisense sequence portion contained by the X through a phosphorothioate bond.

42) The single-stranded oligonucleotide described in any of 32) to 41), wherein the antisense sequence contained by the nucleotide sequence X is a sequence composed of 4 to 30 nucleotides independently selected from sugar-modified nucleotides and deoxyribonucleotides.

43) The single-stranded oligonucleotide described in any of 32) to 42), wherein the antisense sequence contained by the nucleotide sequence X is a sequence composed of 4 to 20 nucleotides including at least one deoxyribonucleotide.

44) The single-stranded oligonucleotide described in any of 32) to 43), wherein the antisense sequence contained by the nucleotide sequence X is a sequence containing at least four contiguous nucleotides recognized by RNase H when hybridizing with a target RNA.

45) The single-stranded oligonucleotide described in any of 32) to 44), wherein the antisense sequence contained by the nucleotide sequence X is a sequence composed of 4 to 20 deoxyribonucleotides.

46) The single-stranded oligonucleotide described in any of 32) to 43), wherein the antisense sequence portion contained by the X contains at least one sugar-modified nucleotide but does not contain an oligonucleotide strand composed of four contiguous deoxyribonucleotides.

47) The single-stranded oligonucleotide described in 46), wherein at least one of a nucleotide on the 3'-side and a nucleotide on the 5'-side of the antisense sequence portion contained by the X is a sugar-modified nucleotide.

48) The single-stranded oligonucleotide described in 46) or 47), wherein the nucleotide on the 3'-side and the nucleotide on the 5'-side of the antisense sequence portion contained by the X are sugar-modified nucleotides.

49) The single-stranded oligonucleotide described in any of 32) to 42), wherein the antisense sequence contained by the nucleotide sequence X is a sequence composed of 4 to 30 sugar-modified nucleotides.

50) The single-stranded oligonucleotide described in any of 32) to 49), wherein nucleotide sequence Y contains a sequence that is capable of hybridizing with at least a portion of the antisense sequence portion contained by the X and contains at least four contiguous nucleotides cleaved by RNase H.

51) The single-stranded oligonucleotide described in 50), wherein the sequence containing the at least four contiguous nucleotides cleaved by RNase H is a sequence composed of 4 to 20 ribonucleotides.

52) The single-stranded oligonucleotide described in 50) or 51), wherein the second oligonucleotide contains a sugar-modified nucleotide bound adjacent to at least one of the 5'-side and 3'-side of a sequence portion containing the at least four contiguous nucleotides cleaved by RNase H.

53) The single-stranded oligonucleotide described in any of 50) to 52), wherein at least one of the 5'-side and 3'-side of the sequence portion containing the at least four contiguous nucleotides cleaved by RNase H is coupled to an adjacent nucleotide through a phosphorothioate bond.

54) The single-stranded oligonucleotide described in any of 32) to 53), wherein at least one of the 5'-side and 3'-side of the second nucleotide sequence portion is coupled to an adjacent nucleotide through a phosphorothioate bond.

55) The single-stranded oligonucleotide described in any of 1) to 28) and 32) to 53), wherein the nucleotide sequence Y contains at least one antisense sequence.

56) The single-stranded oligonucleotide described in 55), wherein the Y has the second nucleotide sequence portion between the antisense sequence portion and L.

57) The single-stranded oligonucleotide described in 55) or 56), wherein the 5'-side and 3'-side of the second nucleo- 58) The single-stranded oligonucleotide described in any of 55) to 57), wherein the antisense sequence portion contained by the Y contains a phosphorothioate bond.

59) The single-stranded oligonucleotide described in any of 55) to 58), the antisense sequence contained by the Y is a sequence containing nucleotides mutually coupled through a phosphorothioate bond.

60) The single-stranded oligonucleotide described in any of 55) to 59), wherein the second oligonucleotide contains a sugar-modified nucleotide bound adjacent to at least one of the 5'-side and 3'-side of the antisense sequence portion contained by the Y.

61) The single-stranded oligonucleotide described in any of 55) to 60), wherein the second oligonucleotide contains sugar-modified nucleotides bound adjacent to the 5'-side and 3'-side of the antisense sequence portion contained by the Y.

62) The single-stranded oligonucleotide described in 60) or 61), wherein the sugar-modified nucleotide bound adjacent to at least one of the 5'-side and 3'-side of the antisense sequence portion contained by the Y is bound to at least one of the 5'-side and 3'-side of the antisense sequence portion contained by the Y through a phosphorothioate bond.

63) The single-stranded oligonucleotide described in any of 55) to 62), wherein the antisense sequence contained by the nucleotide sequence Y is a sequence composed of 4 to 30 nucleotides independently selected from sugar-modified nucleotides and deoxyribonucleotides.

64) The single-stranded oligonucleotide described in any of 55) to 63), wherein the antisense sequence contained by the Y is a sequence composed of 4 to 20 nucleotides including at least one deoxyribonucleotide.

65) The single-stranded oligonucleotide described in any of 55) to 64), wherein the antisense sequence contained by the nucleotide sequence Y is a sequence containing at least four contiguous nucleotides recognized by RNase H when hybridizing with a target RNA.

66) The single-stranded oligonucleotide described in any of 55) to 65), wherein the antisense sequence contained by the Y is a sequence composed of 4 to 20 deoxyribonucleotides.

67) The single-stranded oligonucleotide described in any of 55) to 63), wherein the antisense sequence portion contained by the Y contains at least one sugar-modified nucleotide but does not contain an oligonucleotide strand composed of four contiguous deoxyribonucleotides.

68) The single-stranded oligonucleotide described in 67), wherein at least one of a nucleotide on the 3'-side and a nucleotide on the 5'-side of the antisense sequence portion contained by the Y is a sugar-modified nucleotide.

69) The single-stranded oligonucleotide described in 67) or 68), wherein the nucleotide on the 3'-side and the nucleotide on the 5'-side of the antisense sequence portion contained by the Y are sugar-modified nucleotides.

70) The single-stranded oligonucleotide described in any of 55) to 63), wherein the antisense sequence contained by the nucleotide sequence Y is a sequence composed of 4 to 30 sugar-modified nucleotides.

71) The single-stranded oligonucleotide described in any of 55) to 70), wherein the nucleotide sequence X contains a sequence that is capable of hybridizing with at least a portion of the antisense sequence portion contained by the Y and contains at least four contiguous nucleotides cleaved by RNase H.

72) The single-stranded oligonucleotide described in 71), wherein the sequence containing the at least four contiguous nucleotides cleaved by RNase H is a sequence composed of 4 to 20 ribonucleotides.

73) The single-stranded oligonucleotide described in 71) or 72), wherein the first oligonucleotide contains a sugar-modified nucleotide bound adjacent to at least one of the 5'-side and 3'-side of the sequence portion containing the at least four contiguous nucleotides cleaved by RNase H.

74) The single-stranded oligonucleotide described in any of 71) to 73), wherein at least one of the 5'-side and 3'-side of the sequence portion containing the at least four contiguous nucleotides cleaved by RNase H is coupled to an adjacent nucleotide through a phosphorothioate bond.

75) The single-stranded oligonucleotide described in any of 1) to 74) further containing a group represented by formula

X'-L'-

(wherein, X' represents a group derived from a fourth oligonucleotide composed of 7 to 100 nucleotides that are independently selected from a deoxyribonucleotide, ribonucleotide and sugar-modified nucleotide and that contains at least one nucleotide of which at least one of the sugar moiety, base moiety and phosphate moiety has been modified, and L' represents a group derived from a fifth oligonucleotide that respectively covalently bonds with the first oligonucleotide and the fourth oligonucleotide at both ends thereof and is degraded under physiological conditions; wherein, the fourth oligonucleotide has a nucleotide sequence X' and the nucleotide sequence X' contains an antisense sequence capable of hybridizing with a target RNA).

76) The single-stranded oligonucleotide described in 75), wherein X' contains a 5'-end or a 3'-end.

77) The single-stranded oligonucleotide described in 75) or 76), wherein complementarity between an antisense sequence contained by nucleotide sequence X' and a target RNA sequence is 70% or more.

78) The single-stranded oligonucleotide described in any of 75) to 77), wherein nucleotides contained in the single-stranded oligonucleotide represented by formula X'-L'-X-L-Y are mutually coupled through at least one type of bond respectively and independently selected from the group consisting of a phosphodiester bond, phosphorothioate bond, methyl phosphonate bond, methyl thiophosphonate bond, phosphorodithioate bond and phosphoroamidate bond.

79) The single-stranded oligonucleotide described in any of 75) to 78), wherein each nucleotide contained in the single-stranded oligonucleotide represented by the formula X'-L'-X-L-Y is mutually coupled through at least one type of bond respectively and independently selected from a phosphodiester bond and phosphorothioate bond.

80) The single-stranded oligonucleotide described in any of 75) to 79), wherein the fifth oligonucleotide contains a phosphodiester bond.

81) The single-stranded oligonucleotide described in any of 75) to 80), wherein nucleotides contained in the fifth oligonucleotide are mutually coupled through phosphodiester bonds.

82) The single-stranded oligonucleotide described in any of 75) to 81), wherein the fifth oligonucleotide is composed of 3 to 10 nucleotides independently selected from the group consisting of deoxyribonucleotides and ribonucleotides.

83) The single-stranded oligonucleotide described in any of 75) to 82), wherein the fifth oligonucleotide is an oligodeoxyribonucleotide or oligoribonucleotide composed of 3 to 7 nucleotides.

84) The single-stranded oligonucleotide described in any of 75) to 83), wherein the fifth oligonucleotide is an oligodeoxyribonucleotide or oligoribonucleotide composed of 4 or 5 nucleotides.

85) The single-stranded oligonucleotide described in any of 75) to 84), wherein the fifth oligonucleotide is DNA or RNA.

86) The single-stranded oligonucleotide described in any of 75) to 85), wherein the fifth oligonucleotide is RNA.

87) The single-stranded oligonucleotide described in any of 75) to 86), wherein the fourth oligonucleotide contains a phosphorothioate bond.

88) The single-stranded oligonucleotide described in any of 75) to 87), wherein the antisense sequence contained by the nucleotide sequence X' is a sequence containing nucleotides mutually coupled through a phosphorothioate bond.

89) The single-stranded oligonucleotide described in any of 75) to 88), wherein nucleotides contained in the fourth oligonucleotide are mutually coupled through phosphorothioate bonds.

90) The single-stranded oligonucleotide described in any of 75) to 89), wherein the fourth oligonucleotide contains a sugar-modified nucleotide bound adjacent to at least one of the 5'-side and 3'-side of the antisense sequence portion contained by the X'.

91) The single-stranded oligonucleotide described in any of 75) to 90), wherein the fourth oligonucleotide contains sugar-modified nucleotides bound adjacent to the 5'-side and 3'-side of the antisense sequence portion contained by the X'.

92) The single-stranded oligonucleotide described in any of 75) to 91), wherein the antisense sequence contained by the nucleotide sequence X' is a sequence composed of 4 to 30 nucleotides independently selected from sugar-modified nucleotides and deoxyribonucleotides.

93) The single-stranded oligonucleotide described in any of 75) to 92), wherein the antisense sequence contained by the nucleotide sequence X' is a sequence composed of 4 to 20 nucleotides including at least one deoxyribonucleotide.

94) The single-stranded oligonucleotide described in any of 75) to 93), wherein X' contains at least one sugar-modified nucleotide, and the antisense sequence contained by the nucleotide sequence X' is a sequence containing four contiguous nucleotides recognized by RNase H when hybridizing with a target RNA.

95) The single-stranded oligonucleotide described in any of 75) to 94), wherein the antisense sequence contained by the nucleotide sequence X' is a sequence composed of 4 to 20 deoxyribonucleotides.

96) The single-stranded oligonucleotide described in any of 75) to 93), wherein the antisense sequence portion contained by the X' contains at least one sugar-modified nucleotide but does not contain an oligonucleotide strand composed of four contiguous deoxyribonucleotides.

97) The single-stranded oligonucleotide described in 96), wherein at least one of a nucleotide on the 3'-side and a nucleotide on the 5'-side of the antisense sequence portion contained by the X' is a sugar-modified nucleotide.

98) The single-stranded oligonucleotide described in 96) or 97), wherein the nucleotide on the 3' side and the nucleotide on the 5'-side of the antisense sequence portion contained by the nucleotide sequence X' are sugar-modified nucleotides.

99) The single-stranded oligonucleotide described in any of 75) to 92), wherein the antisense sequence contained by the nucleotide sequence X' is a sequence composed of 4 to 30 sugar-modified nucleotides.

100) The single-stranded oligonucleotide described in any of 75) to 99), wherein nucleotide sequence Y contains a sequence that is capable of hybridizing with at least a portion of the antisense sequence portion contained by the X' and contains at least four contiguous nucleotides cleaved by RNase H.

101) The single-stranded oligonucleotide described in 100), wherein the sequence containing the at least four contiguous nucleotides cleaved by RNase H is a sequence composed of 4 to 20 ribonucleotides.

102) The single-stranded oligonucleotide described in 100) or 101), wherein the second oligonucleotide contains a sugar-modified nucleotide bound adjacent to at least one of the 5'-side and 3'-side of a sequence portion containing the at least four contiguous nucleotides cleaved by RNase H.

103) The single-stranded oligonucleotide described in any of 100) to 102), wherein at least one of the 5'-side and 3'-side of the sequence portion containing the at least four contiguous nucleotides cleaved by RNase H is coupled to an adjacent nucleotide through a phosphorothioate bond.

104) The single-stranded oligonucleotide described in any of 1) to 74), wherein X' contains a 5'-end or a 3'-end.

105) The single-stranded oligonucleotide described in any of 1) to 103), wherein Y contains a 5'-end or a 3'-end.

106) The single-stranded oligonucleotide described in any of 1) to 103), further containing a group derived from a functional molecule having at least one function selected from the group consisting of a labeling function, a purifying function and a target site delivery function.

107) The single-stranded oligonucleotide described in any of 1) to 103), wherein the group derived from a functional molecule is directly or indirectly bound to a second oligonucleotide.

108) The single-stranded oligonucleotide described in any of 1) to 103), wherein the group derived from a functional molecule is directly or indirectly bound to a first oligonucleotide.

109) The single-stranded oligonucleotide described in any of 106) to 108), wherein the group derived from a functional molecule is bound to a first oligonucleotide or second oligonucleotide directly by covalent bonding or through a C2-20 alkylene group, C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—).

110) The single-stranded oligonucleotide described in any of 106) to 109), wherein the C2-20 alkylene group or C2-20 alkenylene group coupled to the group derived from a functional molecule are bound with a phosphodiester bond or modified phosphodiester bond.

111) The single-stranded oligonucleotide described in any of 106) to 110), wherein the C2-20 alkylene group or C2-20 alkenylene group coupled to the group derived from a functional molecule and the first oligonucleotide or second oligonucleotide are coupled through a phosphodiester bond.

112) The single-stranded oligonucleotide described in any of 106) to 111), wherein the functional molecule is selected from the group consisting of sugars, lipids, peptides, proteins and derivatives thereof.

113) The single-stranded oligonucleotide described in any of 106) to 112), wherein the functional molecule is a lipid selected from the group consisting of cholesterol, fatty acids, fat-soluble vitamins, glycolipids and glycerides.

114) The single-stranded oligonucleotide described in any of 106) to 113), wherein the functional molecule is a lipid selected from the group consisting of cholesterol, tocopherol and tocotrienol.

115) The single-stranded oligonucleotide described in any of 106) to 114), wherein the functional molecule is a tocopherol, and the hydroxyl group of the tocopherol is bound to the first oligonucleotide or second oligonucleotide through a C2-20 alkylene group (wherein, methylene groups of the alkylene group are respectively and independently not-replaced or replaced with —O—, and not-replaced methylene groups are respectively and independently unsubstituted or substituted with a hydroxyl group).

116) The single-stranded oligonucleotide described in 115), wherein the hydroxyl group of the tocopherol is bound to the first oligonucleotide or second oligonucleotide through a 1,8-octylene group.

117) The single-stranded oligonucleotide described in any of 106) to 112), wherein the functional molecule is a sugar derivative that interacts with an asialoglycoprotein receptor.

118) The single-stranded oligonucleotide described in any of 106) to 112), wherein the functional molecule is a peptide or protein selected from the group consisting of receptor ligands and antibodies.

119) The single-stranded oligonucleotide described in any of 1) to 118), wherein the sugar-modified nucleotide is respectively and independently a 2'-O-methyl nucleotide, 2'-O-methoxyethyl nucleotide, 2'-O-aminopropyl nucleotide, 2'-fluoronucleotide, 2'-F-arabinonucleotide, bridged nucleotide or 2'-O-methylcarbamoylethyl nucleotide.

120) The single-stranded oligonucleotide described in any of 1) to 119), wherein the sugar-modified nucleotide is respectively and independently a 2'-O-methyl nucleotide or LNA.

121) The single-stranded oligonucleotide described in 75), which contains a partial structure represented by the formula X'-L'-X—, and the partial structure is represented by the formula

X'$^1$—X'$^2$—X'$^3$-L'-X$^1$—X$^2$—X$^3$—

(wherein, X'$^1$ represents a group derived from an oligonucleotide that is composed of 1 to 10 nucleotides independently selected from deoxyribonucleotides, ribonucleotides and sugar-modified nucleotides and includes at least one sugar-modified nucleotide, X'$^2$ represents an antisense sequence portion contained by X', X'$^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a fifth oligonucleotide, L' represents a group derived from an oligonucleotide composed of 2 to 7 nucleotides independently selected from deoxyribonucleotides and ribonucleotides, X$^1$ represents a group derived from an oligonucleotide that is composed of 1 to 10 nucleotides independently selected from deoxyribonucleotides, ribonucleotides and sugar-modified nucleotides and includes at least one sugar-modified nucleotide, X$^2$ represents a first nucleotide sequence portion, and the first nucleotide sequence is an antisense sequence that is a sequence containing at least four contiguous nucleotides recognized by RNase H when hybridizing with a target RNA, and X$^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide).

122) The single-stranded oligonucleotide described in 121), wherein X'$^1$ represents a group derived from an oligonucleotide composed of 2 or 3 nucleotides independently selected from sugar-modified nucleotides, X'$^2$ represents a group derived from an oligonucleotide composed of 8 to 10 deoxyribonucleotides, and X'$^3$ represents a group derived from an oligonucleotide composed of 2 or 3 nucleotides independently selected from sugar-modified nucleotides.

123) The single-stranded oligonucleotide described in 121) or 122), wherein X'$^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and X'$^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

124) The single-stranded oligonucleotide described in any of 121) to 123), wherein X'$^1$ represents a group derived from an oligonucleotide composed of 2 or 3 LNA, and X'$^3$ represents a group derived from an oligonucleotide composed of 2 or 3 nucleotides independently selected from LNA.

125) The single-stranded oligonucleotide described in 75), which contains a partial structure represented by the formula X'$_Z$-L'-X—, and the partial structure is represented by the formula

X'$_Z$-L'-X$^1$—X$^2$—X$^3$—

(wherein, X'$_Z$ represents an antisense sequence portion that contains at least one sugar-modified nucleotide but does not contain an oligonucleotide strand composed of four contiguous nucleotides, and covalently binds with a fifth nucleotide, L' represents a group derived from an oligonucleotide composed of 2 to 7 nucleotides independently selected from deoxyribonucleotides and ribonucleotides, X$^1$ represents a group derived from an oligonucleotide that is composed of 1 to 10 nucleotides independently selected from deoxyribonucleotides, ribonucleotides and sugar-modified nucleotides and includes at least one sugar-modified nucleotide, X$^2$ represents a first nucleotide sequence portion, and the first nucleotide sequence is an antisense sequence that is a sequence containing at least four contiguous nucleotides recognized by RNase H when hybridizing with a target RNA, and X$^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide).

126) The single-stranded oligonucleotide described in 125), wherein $X'_Z$ represents a group derived from an oligonucleotide composed of 6 to 30 nucleotides independently selected from deoxyribonucleotides and sugar-modified nucleotides, and L' represents a group derived from an oligonucleotide composed of 2 to 5 nucleotides independently selected from deoxyribonucleotides.

127) The single-stranded oligonucleotide described in 125) or 126), wherein $X'_Z$ represents a group derived from an oligonucleotide composed of 6 to 30 nucleotides independently selected from deoxyribonucleotides, LNA, 2'-O-methyl nucleotide, 2'-O-methoxyethyl nucleotide and 2'-O-methylcarbamoylethyl nucleotide.

128) The single-stranded oligonucleotide described in 125) or 126), wherein $X'_Z$ represents a group derived from an oligonucleotide composed of 6 to 30 nucleotides independently selected from deoxyribonucleotides and LNA.

129) The single-stranded oligonucleotide described in any of 121) to 128), wherein $X^1$ represents a group derived from an oligonucleotide composed of 2 or 3 nucleotides independently selected from sugar-modified nucleotides, $X^2$ represents a group derived from an oligonucleotide composed of 8 to 10 deoxyribonucleotides, and $X^3$ represents a group derived from an oligonucleotide composed of 2 or 3 nucleotides independently selected from sugar-modified nucleotides.

130) The single-stranded oligonucleotide described in 121) to 129), wherein $X^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and $X^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

131) The single-stranded oligonucleotide described in any of 121) to 130), wherein $X^1$ represents a group derived from an oligonucleotide composed of 2 or 3 LNA, and $X^3$ represents a group derived from an oligonucleotide composed of 2 or 3 nucleotides independently selected from LNA.

132) The single-stranded oligonucleotide described in any of 1) to 24), wherein the partial structure represented by formula X— is represented by the formula

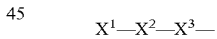

(wherein, $X^4$ represents a group derived from an oligonucleotide that is composed of 1 to 10 nucleotides independently selected from deoxyribonucleotides, ribonucleotides and sugar-modified nucleotides, and includes at least one sugar-modified nucleotide, $X^5$ represents a group derived from an oligonucleotide that is composed of 4 to 20 nucleotides independently selected from deoxyribonucleotides, ribonucleotides and sugar-modified nucleotides and includes at least one ribonucleotide, $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^2$ represents a first nucleotide sequence portion, and the first nucleotide sequence is an antisense sequence that is a sequence containing at least four contiguous nucleotides recognized by RNase H when hybridizing with a target RNA, and $X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide).

133) The single-stranded oligonucleotide described in 132), wherein $X^4$ represents a group derived from an oligonucleotide composed of 2 or 3 nucleotides independently selected from sugar-modified nucleotides, $X^5$ represents a group derived from an oligonucleotide composed of 10 to 19 ribonucleotides, $X^1$ represents a group derived from an oligonucleotide composed of 2 or 3 nucleotides independently selected from sugar-modified nucleotides, $X^2$ represents a group derived from an oligonucleotide composed of 8 to 10 deoxyribonucleotides, and $X^3$ represents a group derived from an oligonucleotide composed of 2 or 3 nucleotides independently selected from sugar-modified nucleotides.

134) The single-stranded oligonucleotide described in 132) or 133), wherein $X^4$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, $X^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and $X^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

135) The single-stranded oligonucleotide described in any of 132) to 134), wherein $X^4$ represents a group derived from an oligonucleotide composed of 2 or 3 2'-O-methyl nucleotides, $X^1$ represents a group derived from an oligonucleotide composed of 2 or 3 LNA, and $X^3$ represents a group derived from an oligonucleotide composed of 2 or 3 LNA.

136) The single-stranded oligonucleotide described in any of 1) to 24), wherein the partial structure represented by formula X— is represented by the formula

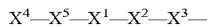

(wherein, $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^2$ represents a first nucleotide sequence portion, and the first nucleotide sequence is an antisense sequence that is a sequence containing at least four contiguous nucleotides recognized by RNase H when hybridizing with a target RNA, and $X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide).

137) The single-stranded oligonucleotide described in 136), wherein $X^1$ represents a group derived from an oligonucleotide composed of 2 or 3 nucleotides independently selected from sugar-modified nucleotides, $X^2$ represents a group derived from an oligonucleotide composed of 8 to 10 deoxyribonucleotides, and $X^3$ represents a group derived from an oligonucleotide composed of 2 or 3 nucleotides independently selected from sugar-modified nucleotides.

138) The single-stranded oligonucleotide described in 136) or 137), wherein $X^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and $X^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

139) The single-stranded oligonucleotide described in any of 136) to 138), wherein $X^1$ represents a group derived from an oligonucleotide composed of 2 or 3 LNA, and $X^3$ represents a group derived from an oligonucleotide composed of 2 or 3 LNA.

140) The single-stranded oligonucleotide described in any of 1) to 24), wherein the partial structure represented by formula X— is represented by the formula $X_Z^1-X_Z^2-X_Z^3-X^0-X^2-$ (wherein, $X_Z^1$ represents a group derived from an oligonucleotide that is composed of 1 to 10 nucleotides independently selected from deoxyribonucleotides, ribonucleotides and sugar-modified nucleotides, and includes at least one sugar-modified nucleotide, $X_Z^2$ represents an antisense sequence portion contained by X, $X_Z^3$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^0$ represents a group derived from an oligonucleotide composed of 2 to 7 nucleotides independently selected from deoxyribonucleotides and ribonucleotides, and $X^2$ represents a first nucleotide sequence portion that covalently bonds with a third oligonucleotide.

141) The single-stranded oligonucleotide described in 140), wherein $X_Z^1$ represents a group derived from an oligonucleotide composed of 2 or 3 nucleotides independently selected from sugar-modified nucleotides, $X_Z^2$ represents a group derived from an oligonucleotide composed of 8 to 10 deoxyribonucleotides, $X_Z^3$ represents a group derived from an oligonucleotide composed of 2 or 3 nucleotides independently selected from sugar-modified nucleotides, and $X^2$ represents a group derived from an oligonucleotide composed of 8 to 17 deoxyribonucleotides.

142) The single-stranded oligonucleotide described in 140) or 141), wherein $X_Z^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and $X_Z^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

143) The single-stranded oligonucleotide described in any of 140) to 142), wherein $X_Z^1$ represents a group derived from an oligonucleotide composed of 2 or 3 LNA, and $X_Z^3$ represents a group derived from an oligonucleotide composed of 2 or 3 LNA.

144) The single-stranded oligonucleotide described in any of 1) to 24), wherein the partial structure represented by formula X— is represented by the formula $X_Z-X^0-X^2-$ (wherein, $X_Z$ represents an antisense sequence portion that contains at least one sugar-modified nucleotide but does not contain an oligonucleotide strand composed of four contiguous deoxyribonucleotides, $X^0$ represents a group derived from an oligonucleotide composed of 2 to 7 nucleotides independently selected from deoxyribonucleotides and ribonucleotides, and $X^2$ represents a first nucleotide sequence portion that covalently bonds with a third oligonucleotide).

145) The single-stranded oligonucleotide described in 144), wherein $X_Z$ represents a group derived from an oligonucleotide composed of 6 to 30 nucleotides independently selected from deoxyribonucleotides and sugar-modified nucleotides, $X^0$ represents a group derived from an oligonucleotide composed of 2 to 5 nucleotides independently selected from deoxyribonucleotides, and $X^2$ represents a group derived from an oligonucleotide composed of 8 to 17 deoxyribonucleotides.

146) The single-stranded oligonucleotide described in 144) or 145), wherein $X_Z$ represents a group derived from an oligonucleotide composed of 6 to 30 nucleotides independently selected from deoxyribonucleotide, LNA, 2'-O-methyl nucleotide, 2'-O-methoxyethyl nucleotide and 2'-O-methylcarbamoylethyl nucleotide.

147) The single-stranded oligonucleotide described in 144) or 145), wherein $X_Z$ represents a group derived from an oligonucleotide composed of 6 to 30 nucleotides independently selected from deoxyribonucleotides and LNA.

148) The single-stranded oligonucleotide described in any of 1) to 24), wherein the partial structure represented by formula X— is represented by the formula $X^1-X^2-$ (wherein, $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, and $X^2$ represents a first nucleotide sequence portion that covalently bonds with a third oligonucleotide).

149) The single-stranded oligonucleotide described in 148), wherein $X^1$ represents a group derived from an oligonucleotide composed of 2 or 3 nucleotides independently selected from sugar-modified nucleotides, and $X^2$ represents a group derived from an oligonucleotide composed of 8 to 12 deoxyribonucleotides.

150) The single-stranded oligonucleotide described in 148) or 149), wherein $X^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

151) The single-stranded oligonucleotide described in 148) to 150), wherein $X^1$ represents a group derived from an oligonucleotide composed of 2 or 3 2'-O-methyl nucleotides.

152) The single-stranded oligonucleotide described in any of 1) to 24) and 121) to 147), wherein the partial structure represented by formula —Y is represented by the formula $-Y^2-Y^1$ (wherein, $Y^2$ represents a group derived from an oligonucleotide that is a second nucleotide sequence portion composed of 4 to 20 nucleotides independently selected from deoxyribonucleotides, ribonucleotides and sugar-modified nucleotides and includes at least one ribonucleotide, and the oligonucleotide covalently bonds with a third oligonucleotide, and $Y^1$ represents a group derived from an oligonucleotide that is composed of 1 to 10 nucleotides independently selected from deoxyribonucleotides, ribonucleotides and sugar-modified nucleotides and includes at least one sugar-modified nucleotide).

153) The single-stranded oligonucleotide described in 152), wherein $Y^2$ represents a group derived from an oligonucleotide composed of 10 to 13 ribonucleotides, and $Y^1$ represents a group derived from an oligonucleotide composed of 2 or 3 nucleotides independently selected from sugar-modified nucleotides.

154) The single-stranded oligonucleotide described in 152) or 153), wherein $Y^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

155) The single-stranded oligonucleotide described in 152) to 154), wherein $Y^1$ represents a group derived from an oligonucleotide composed of 2 or 3 2'-O-methyl nucleotides.

156) The single-stranded oligonucleotide described in any of 1) to 24) and 121) to 147), wherein the partial structure represented by formula —Y is represented by the formula $$-Y^2-Y^1$$

(wherein, $Y^2$ represents a group derived from an oligonucleotide that contains a second nucleotide sequence portion, is composed of 4 to 40 nucleotides independently selected from deoxyribonucleotides, ribonucleotides and sugar-modified nucleotides and includes at least one ribonucleotide, and the oligonucleotide covalently bonds with a third oligonucleotide, and $Y^1$ represents a group derived from an oligonucleotide that is composed of 1 to 10 nucleotides independently selected from deoxyribonucleotides, ribonucleotides and sugar-modified nucleotides and includes at least one sugar-modified nucleotide).

157) The single-stranded oligonucleotide described in 156), wherein $Y^2$ represents a group derived from an oligonucleotide composed of 25 to 36 ribonucleotides, and $Y^1$ represents a group derived from an oligonucleotide composed of 2 or 3 nucleotides independently selected from sugar-modified nucleotides.

158) The single-stranded oligonucleotide described in 156) or 157), wherein $Y^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

159) The single-stranded oligonucleotide described in 156) to 158), wherein $Y^1$ represents a group derived from an oligonucleotide composed of 2 or 3 2'-O-methyl nucleotides.

160) The single-stranded oligonucleotide described in any of 1) to 24) and 121) to 151), wherein the partial structure represented by formula —Y is represented by the formula $$-Y^0-Y_Z^3-Y_Z^2-Y_Z^1$$

(wherein, $Y^0$ represents a second nucleotide sequence portion that covalently bonds with a third oligonucleotide, $Y_Z^3$ represents a group derived from an oligonucleotide that is composed of 1 to 10 nucleotides independently selected from deoxyribonucleotides, ribonucleotides and sugar-modified nucleotides and includes at least one sugar-modified nucleotide, $Y_Z^2$ represents an antisense sequence portion contained by Y, and $Y_Z^1$ represents a group derived from an oligonucleotide that is composed of 1 to 10 nucleotides independently selected from deoxyribonucleotides, ribonucleotides and sugar-modified nucleotides and includes at least one sugar-modified nucleotide).

161) The single-stranded oligonucleotide described in 160), wherein $Y^0$ represents a group derived from an oligonucleotide composed of 10 to 22 ribonucleotides, $Y_Z^3$ represents a group derived from an oligonucleotide composed of 2 or 3 nucleotides independently selected from sugar-modified nucleotides, $Y_Z^2$ represents a group derived from an oligonucleotide composed of 8 to 10 deoxyribonucleotides, and $Y_Z^1$ represents a group derived from an oligonucleotide composed of 2 or 3 nucleotides independently selected from sugar-modified nucleotides.

162) The single-stranded oligonucleotide described in 160) or 161), wherein $Y_Z^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and $Y_Z^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

163) The single-stranded oligonucleotide described in 160) to 162), wherein $Y_Z^1$ represents a group derived from an oligonucleotide composed of 2 or 3 LNA, and $Y_Z^3$ represents a group derived from an oligonucleotide composed of 2 or 3 LNA.

164) The single-stranded oligonucleotide described in any of 1) to 24) and 121) to 151), wherein the partial structure represented by formula —Y is represented by the formula $$-Y^0-Y_Z$$

(wherein, $Y^0$ represents a second nucleotide sequence portion that covalently bonds with a third oligonucleotide, and $Y_Z$ represents an antisense sequence portion that contains at least one sugar-modified nucleotide but does not contain an oligonucleotide strand composed of four contiguous deoxyribonucleotides).

165) The single-stranded oligonucleotide described in 164), wherein $Y^0$ represents a group derived from an oligonucleotide composed of 10 to 22 ribonucleotides, and $Y_Z$ represents a group derived from an oligonucleotide composed of 6 to 30 nucleotides independently selected from deoxyribonucleotides and sugar-modified nucleotides.

166) The single-stranded oligonucleotide described in 164) or 165), wherein $Y_Z$ represents a group derived from an oligonucleotide composed of 6 to 30 nucleotides independently selected from deoxyribonucleotide, LNA, 2'-O-methyl nucleotide, 2'-O-methoxyethyl nucleotide and 2'-O-methylcarbamoylethyl nucleotide.

167) The single-stranded oligonucleotide described in 164) or 165), wherein $Y_Z$ represents a group derived from an oligonucleotide composed of 6 to 30 nucleotides independently selected from deoxyribonucleotides and LNA.

B-1) A single-stranded nucleotide represented by the formula X-L-Y (wherein, X represents a group derived from a first oligonucleotide that is composed of 7 to 100 nucleotides independently selected from deoxyribonucleotides, ribonucleotides and sugar-modified nucleotides and includes at least one sugar-modified nucleotide, the first oligonucleotide has a first nucleotide sequence capable of hybridizing with a target RNA, and the first nucleotide sequence is a sequence containing at least four contiguous nucleotides recognized by RNase H when hybridizing with the target RNA, Y represents a group derived from a second oligonucleotide composed of 4 to 100 nucleotides independently selected from deoxyribonucleotides, ribonucleotides and sugar-modified nucleotides, and the second oligonucleotide has a second nucleotide sequence that is capable of hybridizing with the first oligonucleotide and contains at least one ribonucleotide, and L represents a group derived from a third oligonucleotide that respectively covalently bonds with the first oligonucleotide and the second oligonucleotide at both ends thereof and is degraded under physiological conditions); wherein, X and Y hybridize by the first nucleotide sequence portion and the second nucleotide sequence portion within a molecule thereof.

B-2) The single-stranded oligonucleotide described in B-1), wherein X bonds to L on the 3'-side and Y bonds to L on the 5'-side.

B-3) The single-stranded oligonucleotide described in B-1), wherein X bonds to L on the 5'-side and Y bonds to L on the 3'-side.

B-4) The single-stranded oligonucleotide described in any of B-1) to B-3), wherein complementarity between the first nucleotide sequence and a target RNA sequence is 70% or more.

B-5) The single-stranded oligonucleotide described in any of B-1) to B-4), wherein complementarity between the first nucleotide sequence and the second nucleotide sequence is 70% or more.

B-6) The single-stranded oligonucleotide described in any of B-1) to B-5), wherein nucleotides contained in the third oligonucleotide are mutually coupled through phosphodiester bonds.

B-7) The single-stranded oligonucleotide described in any of B-1) to B-6), wherein the third oligonucleotide is composed of 3 to 10 nucleotides independently selected from the group consisting of deoxyribonucleotides and ribonucleotides.

B-8) The single-stranded oligonucleotide described in any of B-1) to B-7), wherein the third oligonucleotide is an oligodeoxyribonucleotide or oligoribonucleotide.

B-9) The single-stranded oligonucleotide described in any of B-1) to B-8), wherein the third oligonucleotide is DNA or RNA.

B-10) The single-stranded oligonucleotide described in any of B-1) to B-9), wherein the third oligonucleotide is RNA.

B-11) The single-stranded oligonucleotide described in any of B-1) to B-10), wherein the third oligonucleotide is an oligonucleotide composed of 4 or 5 adenosines.

B-12) The single-stranded oligonucleotide described in any of B-1) to B-11), wherein the first oligonucleotide contains a sugar-modified nucleotide bound adjacent to at least one of the 5'-side and 3'-side of the first nucleotide sequence portion.

B-13) The single-stranded oligonucleotide described in any of B-1) to B-12), wherein the first oligonucleotide contains sugar-modified nucleotides bound adjacent to the 5'-side and 3'-side of the first nucleotide sequence portion.

B-14) The single-stranded oligonucleotide described in any of B-1) to B-13), wherein the first oligonucleotide contains a phosphorothioate bond.

B-15) The single-stranded oligonucleotide described in any of B-1) to B-14), wherein the first nucleotide sequence is a sequence containing nucleotides mutually coupled through a phosphorothioate bond.

B-16) The single-stranded oligonucleotide described in any of B-1) to B-15), wherein nucleotides contained in the first oligonucleotide are mutually coupled through phosphorothioate bonds.

B-17) The single-stranded oligonucleotide described in any of B-1) to B-16), wherein the first nucleotide sequence is a sequence composed of 4 to 20 nucleotides including at least one deoxyribonucleotide.

B-18) The single-stranded oligonucleotide described in any of B-1) to B-17), wherein the first nucleotide sequence is a sequence composed of 4 to 20 deoxyribonucleotides.

B-19) The single-stranded oligonucleotide described in any of B-1) to B-18), wherein the second nucleotide sequence is a sequence that contains at least four contiguous nucleotides cleaved by RNase H.

B-20) The single-stranded oligonucleotide described in any of B-1) to B-19), wherein the second nucleotide sequence is a sequence composed of 4 to 20 ribonucleotides.

B-21) The single-stranded oligonucleotide described in B-19) or B-20), wherein at least one of the 5'-side and 3'-side of the second nucleotide sequence portion is coupled to an adjacent nucleotide through a phosphorothioate bond.

B-22) The single-stranded oligonucleotide described in of B-19) to B-21), wherein the second oligonucleotide contains a sugar-modified nucleotide bound adjacent to at least one of the 5'-side and 3'-side of the second nucleotide sequence portion.

B-23) The single-stranded oligonucleotide described in any of B-1) to B-22), wherein Y contains a 5'-end or 3'-end.

B-24) The single-stranded oligonucleotide described in any of B-1) to B-22), which further contains a group derived from a functional molecule having at least one function selected from the group consisting of a labeling function, a purifying function or delivery function to a target RNA.

B-25) The single-stranded oligonucleotide described in B-24), wherein the group derived from a functional molecule is indirectly or directly bound to the second oligonucleotide.

B-26) The single-stranded oligonucleotide described in B-24) or B-25), wherein the group derived from a functional molecule is bound to the second oligonucleotide directly by covalent bonding or through a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—).

B-27) The single-stranded oligonucleotide described in any of B-24) to B-26), wherein the functional molecule is selected from the group consisting of sugars, lipids, peptides, proteins and derivatives thereof.

B-28) The single-stranded oligonucleotide described in any of B-24) to B-27), wherein the functional molecule is a lipid selected from the group consisting of cholesterol, fatty acids, fat-soluble vitamins, glycolipids and glycerides.

B-29) The single-stranded oligonucleotide described in any of B-24) to B-28), wherein the functional molecule is a lipid selected from the group consisting of cholesterol, tocopherol and tocotrienol.

B-30) The single-stranded oligonucleotide described in any of B-24) to B-29), wherein the functional molecule includes tocopherol, and the hydroxyl group of the tocopherol is bound to the second oligonucleotide through a C2-20 alkylene group (wherein, methylene groups of the alkylene group are respectively and independently not-replaced or replaced with —O—, and not-replaced methylene groups are respectively and independently unsubstituted or substituted with a hydroxyl group).

B-31) The single-stranded oligonucleotide described in any of B-24) to B-30), wherein the functional molecule includes tocopherol, and the hydroxyl group of the tocopherol is bound to the second oligonucleotide through a 1,8-octylene group or group represented by the following formula (II):

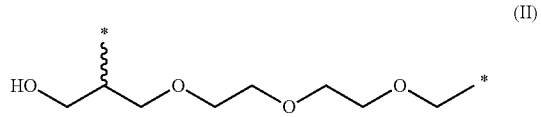

(wherein, one asterisk (*) represents a bonding site with the second oligonucleotide, while the other asterisk (*) represents a bonding site with tocopherol).

B-32) The single-stranded oligonucleotide described in any of B-24) to B-27), wherein the functional molecule is a sugar derivative that interacts with an asialoglycoprotein receptor.

B-33) The single-stranded oligonucleotide described in any of B-24) to B-27), wherein the functional molecule is a peptide or protein selected from the group consisting of receptor ligands and antibodies.

B-34) The single-stranded oligonucleotide described in any of B-1) to B-33), wherein X contains a 5'-end or 3'-end.

B-35) The single-stranded oligonucleotide described in any of B-1) to B-33), further containing a group represented by formula

X'-L'-

(wherein, X' represents a group derived from a fourth oligonucleotide that is composed of 7 to 100 nucleotides independently selected from deoxyribonucleotides, ribonucleotides and sugar-modified nucleotides and includes at least one sugar-modified nucleotide, the fourth oligonucleotide has a fourth nucleotide sequence capable of hybridizing with a target RNA, the fourth nucleotide sequence is a sequence that contains at least four contiguous nucleotides recognized by RNase H when hybridizing with the target RNA, and L' represents a group derived from a fifth oligonucleotide that respectively covalently bonds with the first oligonucleotide and the fourth oligonucleotide at both ends thereof and is degraded under physiological conditions; wherein, the target RNA hybridized by the first nucleotide sequence portion and the target RNA hybridized by the fourth nucleotide sequence portion may be the same or different).

B-36) The single-stranded oligonucleotide described in B-35), wherein X' contains a 5'-end or a 3'-end.

B-37) The single-stranded oligonucleotide described in B-35) or B-36), wherein complementarity between the fourth nucleotide sequence and the target RNA sequence is 70% or more.

B-38) The single-stranded oligonucleotide described in any of B-35) to B-37), wherein nucleotides contained in the fifth oligonucleotide are mutually coupled through phosphodiester bonds.

B-39) The single-stranded oligonucleotide described in any of B-35) to B-38), wherein the fifth oligonucleotide is composed of 3 to 10 nucleotides independently selected from the group consisting of deoxyribonucleotides and ribonucleotides.

B-40) The single-stranded oligonucleotide described in any of B-35) to B-39), wherein the fifth oligonucleotide is DNA or RNA.

B-41) The single-stranded oligonucleotide described in any of B-35) to B-40), wherein the fifth oligonucleotide is RNA composed of 3 to 7 nucleotides.

B-42) The single-stranded oligonucleotide described in any of B-35) to B-41), wherein the fourth oligonucleotide contains a sugar-modified nucleotide bound adjacent to at least one of the 5'-side and 3'-side of the fourth nucleotide sequence portion.

B-43) The single-stranded oligonucleotide described in any of B-35) to B-42), wherein the fourth oligonucleotide contains sugar-modified nucleotides bound adjacent to the 5'-side and 3'-side of the fourth nucleotide sequence portion.

B-44) The single-stranded oligonucleotide described in any of B-35) to B-43), wherein the fourth oligonucleotide contains a phosphorothioate bond.

B-45) The single-stranded oligonucleotide described in any of B-35) to B-44), wherein the fourth nucleotide sequence is a sequence containing nucleotides mutually coupled through a phosphorothioate bond.

B-46) The single-stranded oligonucleotide described in any of B-35) to B-45), wherein nucleotides contained in the fourth oligonucleotide are mutually coupled through phosphorothioate bonds.

B-47) The single-stranded oligonucleotide described in any of B-35) to B-46), wherein the fourth nucleotide sequence portion is a sequence composed of 4 to 20 nucleotides including at least one deoxyribonucleotide.

B-48) The single-stranded oligonucleotide described in any of B-35) to B-47), wherein the fourth nucleotide sequence portion is a sequence composed of 4 to 20 deoxyribonucleotides.

B-49) The single-stranded oligonucleotide described in any B-1) to B-48), wherein the sugar-modified nucleotide is respectively and independently a 2'-O-methyl nucleotide, 2'-O-methoxyethyl nucleotide, 2'-O-aminopropyl nucleotide, 2'-fluoronucleotide, T-F-arabinonucleotide, bridged nucleotide or 2'-O-methylcarbamoylethyl nucleotide.

B-50) The single-stranded oligonucleotide described in any of B-1) to B-49), wherein the sugar-modified nucleotide is respectively and independently a 2'-O-methyl nucleotide or LNA.

B-51) The single-stranded oligonucleotide described in any of B-1) to B-50), wherein the base moiety in a deoxyribonucleotide, ribonucleotide and sugar-modified nucleotide is at least one type selected from the group consisting of adenine (A), guanine (G), thymine (T), cytosine (C), uracil (U) and 5-methylcytosine (5-me-C).

B-52) The single-stranded oligonucleotide described in any of B-1) to B-51), wherein the partial structure represented by the formula X— is represented by the formula $X^1$—$X^2$—$X^3$ (wherein, $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^2$ represents a group derived from an oligonucleotide of a first nucleotide sequence portion, and $X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide).

B-53) The single-stranded oligonucleotide described in B-52), wherein X' represents a group derived from an oligonucleotide composed of 2 or 3 sugar-modified nucleotides, $X^2$ represents a group derived from an oligonucleotide composed of 8 to 10 deoxyribonucleotides, and $X^3$ represents a group derived from an oligonucleotide composed of 2 or 3 sugar-modified nucleotides.

B-54) The single-stranded oligonucleotide described in B-52) or B-53), wherein $X^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide, and $X^3$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

B-55) The single-stranded oligonucleotide described in any of B-52) to B-54), wherein $X^1$ represents a group derived from an oligonucleotide composed of 2 or 3 LNA, and $X^3$ represents a group derived from an oligonucleotide composed of 2 or 3 nucleotides independently selected from LNA.

B-56) The single-stranded oligonucleotide described in any of B-1) to B-55), wherein the partial structure represented by formula —Y is represented by the formula —$Y^2$—$Y^1$ (wherein, $Y^2$ represents a group derived from an oligonucleotide of a second nucleotide sequence portion that is composed of 4 to 20 nucleotides independently selected from deoxyribonucleotides, ribonucleotides and sugar-modified nucleotides and includes at least one ribonucleotide, and the oligonucleotide covalently bonds with a third oligonucleotide, and $Y^1$ represents a group derived from an oligonucleotide that is composed of 1 to 10 nucleotides independently selected from deoxyribonucleotides, ribonucleotides and sugar-modified nucleotides and includes at least one sugar-modified nucleotide).

B-57) The single-stranded oligonucleotide described in B-56), wherein $Y^2$ represents a group derived from an oligonucleotide composed of 10 to 13 ribonucleotides, and $Y^1$ represents a group derived from an oligonucleotide composed of 2 or 3 sugar-modified nucleotides.

B-58) The single-stranded oligonucleotide described in B-56) or B-57), wherein $Y^1$ represents a group derived from an oligonucleotide composed of 2 or 3 nucleotides independently selected from LNA, 2'-O-methyl nucleotide, 2'-O-methoxyethyl nucleotide and 2'-O-methylcarbamoylethyl nucleotide.

B-59) The single-stranded oligonucleotide described in B-56) to B-58), wherein $Y^1$ represents a group derived from an oligonucleotide composed of 2 or 3 2'-O-methyl nucleotides.

B-60) The single-stranded oligonucleotide described in B-1) represented by the formula

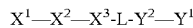

(wherein, $X^1$ represents a group derived from an oligonucleotide composed of 2 or 3 LNA, $X^2$ represents a group derived from an oligonucleotide of a first nucleotide sequence portion that is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^2$ represents a group derived from an oligonucleotide of a second nucleotide sequence portion that is composed of 10 to 13 ribonucleotides, and $Y^1$ represents a group derived from an oligonucleotide composed of 2 or 3 2'-O-methyl nucleotides; wherein, nucleotides contained in $X^1$, $X^2$, $X^3$ and $Y^1$ are mutually coupled through phosphorothioate bonds, and nucleotides contained in L and $Y^2$ are mutually coupled through phosphodiester bonds).

B-61) The single-stranded oligonucleotide described in B-24) represented by the formula

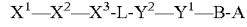

(wherein, $X^1$ represents a group derived from an oligonucleotide composed of 2 or 3 LNA, $X^2$ represents a group derived from an oligonucleotide of a first nucleotide sequence portion that is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^2$ represents a group derived from an oligonucleotide of a second nucleotide sequence portion that is composed of 10 to 13 ribonucleotides, $Y^1$ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —$NR^B$— (wherein, $R^B$ represents a hydrogen atom, C1-6 alkyl group or halo-C1-6 alkyl group), —S—, —S(O)— or —S(O)$_2$—), and A represents a group derived from a functional molecule; wherein, nucleotides contained in $X^1$, $X^2$, $X^3$ and $Y^1$ are mutually coupled through phosphorothioate bonds, and nucleotides contained in L and $Y^2$ are mutually coupled through phosphodiester bonds).

B-62) The single-stranded oligonucleotide described in B-61), wherein B represents a C2-20 alkylene group (methylene groups of the alkylene group are respectively and independently not-replaced or replaced with —O—, and unsubstituted methylene groups are respectively and independently unsubstituted or substituted with a hydroxyl group).

B-63) The single-stranded oligonucleotide described in any of B-60 to B-62), wherein each of the terminal nucleotides of X¹ and X², X² and X³, and Y² and Y¹ is coupled through a phosphorothioate bond, and each of the terminal nucleotides of X³ and L, and L and Y² is coupled through a phosphodiester bond.

B-64) The single-stranded oligonucleotide described in B-35) represented by the formula

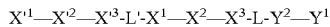

X'¹—X'²—X'³-L'-X¹—X²—X³-L-Y²—Y¹

(wherein, X¹ represents a group derived from an oligonucleotide composed of 2 or 3 LNA, X² represents a group derived from an oligonucleotide of a first nucleotide sequence portion that is composed of 8 to 10 deoxyribonucleotides, X³ represents a group derived from an oligonucleotide composed of 2 or 3 LNA, X'¹ represents a group derived from an oligonucleotide composed of 2 or 3 LNA, X'² represents a group derived from an oligonucleotide of a fourth nucleotide sequence portion that is composed of 8 to 10 deoxyribonucleotides, X'³ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, Y² represents a group derived from an oligonucleotide of a second nucleotide sequence portion that is composed of 10 to 13 ribonucleotides, and Y¹ represents a group derived from an oligonucleotide composed of 2 or 3 2'-O-methyl nucleotides; wherein, nucleotides contained in X¹, X², X³, X'¹, X'², X'³, and Y¹ are mutually coupled through phosphorothioate bonds, and nucleotides contained in L, L' and Y² are mutually coupled through phosphodiester bonds).

B-65) The single-stranded oligonucleotide described in B-35) represented by the formula

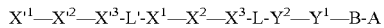

X'¹—X'²—X'³-L'-X¹—X²—X³-L-Y²—Y¹—B-A (wherein, X¹ represents a group derived from an oligonucleotide composed of 2 or 3 LNA, X² represents a group derived from an oligonucleotide of a first nucleotide sequence portion that is composed of 8 to 10 deoxyribonucleotides, X³ represents a group derived from an oligonucleotide composed of 2 or 3 LNA, X'¹ represents a group derived from an oligonucleotide composed of 2 or 3 LNA, X'² represents a group derived from an oligonucleotide of a fourth nucleotide sequence portion that is composed of 8 to 10 deoxyribonucleotides, X'³ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, Y² represents a group derived from an oligonucleotide of a second nucleotide sequence portion that is composed of 10 to 13 ribonucleotides, Y¹ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—), and A represents a group derived from a functional molecule; wherein, nucleotides contained in X¹, X², X³, X'¹, X'², X'³ and Y¹ are mutually coupled through phosphorothioate bonds, and nucleotides contained in L, L' and Y² are mutually coupled through phosphodiester bonds).

B-66) The single-stranded oligonucleotide described in B-65), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

B-67) The single-stranded oligonucleotide described in any of B-64) to B-66), wherein each of the terminal nucleotides of X¹ and X², X² and X³, X'¹ and X'², X'² and X'³ and Y² and Y¹ is coupled through a phosphorothioate bond, and each of the terminal nucleotides of X³ and L, L and Y², X'³ and L' and L' and X¹ is coupled through a phosphodiester bond.

B-68) The single-stranded oligonucleotide described in any of B-60) to B-67), wherein X¹ and Y¹ hybridize within a molecule thereof.

B-69) The single-stranded oligonucleotide described in any of B-60) to B-68), wherein complementarity between the base sequence of nucleotides composing X¹ and the base sequence of nucleotides composing Y¹ is 70% or more.

B-70) The single-stranded oligonucleotide described in any of B-60) to B-69), wherein X³ and Y² hybridize within a molecule thereof.

B-71) The single-stranded oligonucleotide described in any of B-60) to B-70), wherein complementarity between the base sequence of nucleotides composing X²—X³ and the base sequence of nucleotides composing Y² is 70% or more.

B-72) The single-stranded oligonucleotide described in B-35) represented by the formula

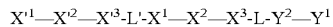

X'¹—X'²—X'³-L'-X¹—X²—X³-L-Y²—Y¹

(wherein, X¹ represents a group derived from an oligonucleotide composed of 2 or 3 LNA, X² represents a group derived from an oligonucleotide of a first nucleotide sequence portion that is composed of 8 to 10 deoxyribonucleotides, X³ represents a group derived from an oligonucleotide composed of 2 or 3 LNA, X'¹ represents a group derived from an oligonucleotide composed of 2 or 3 LNA, X'² represents a group derived from an oligonucleotide of a fourth nucleotide sequence portion that is composed of 8 to 10 deoxyribonucleotides, X'³ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, $Y^2$ represents a group derived from an oligonucleotide of a second nucleotide sequence portion that is composed of 25 to 36 ribonucleotides, and $Y^1$ represents a group derived from an oligonucleotide composed of 2 or 3 2'-O-methyl nucleotides; wherein, nucleotides contained in $X^1$, $X^2$, $X^3$, $X'^1$, $X'^2$, $X'^3$ and $Y^1$ are mutually coupled through phosphorothioate bonds, and nucleotides contained in L, L' and $Y^2$ are mutually coupled through phosphodiester bonds).

B-73) The single-stranded oligonucleotide described in B-35) represented by the formula $$X'^1\text{—}X'^2\text{—}X'^3\text{-L'-}X^1\text{—}X^2\text{—}X^3\text{-L-}Y^2\text{—}Y^1\text{—B-A}$$

(wherein, $X^1$ represents a group derived from an oligonucleotide composed of 2 or 3 LNA, $X^2$ represents a group derived from an oligonucleotide of a first nucleotide sequence portion that is composed of 8 to 10 deoxyribonucleotides, $X^3$ represents a group derived from an oligonucleotide composed of 2 or 3 LNA, $X'^1$ represents a group derived from an oligonucleotide composed of 2 or 3 LNA, $X'^2$ represents a group derived from an oligonucleotide of a fourth nucleotide sequence portion that is composed of 8 to 10 deoxyribonucleotides, $X'^3$ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, $Y^2$ represents a group derived from an oligonucleotide of a second nucleotide sequence portion that is composed of 25 to 36 ribonucleotides, $Y^1$ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—), and A represents a group derived from a functional molecule; wherein, nucleotides contained in $X^1$, $X^2$, $X^3$, $X'^1$, $X'^2$, $X'^3$ and $Y^1$ are mutually coupled through phosphorothioate bonds, and nucleotides contained in L, L and $Y^2$ are mutually coupled through phosphodiester bonds).

B-74) The single-stranded oligonucleotide described in B-73), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

B-75) The single-stranded oligonucleotide described in any of B-72) to B-74), wherein each of the terminal nucleotides of $X^1$ and $X^2$, $X^2$ and $X^3$, $X'^1$ and $X'^2$, $X'^2$ and $X'^3$ and $Y^2$ and $Y^1$ is coupled through a phosphorothioate bond, and each of the terminal nucleotides of $X^3$ and L, L and $Y^2$, $X'^3$ and L' and L' and $X^1$ is coupled through a phosphodiester bond.

B-76) The single-stranded oligonucleotide described in any of B-72) to B-75), wherein $X'^1$ and $Y'^1$ hybridize within a molecule thereof.

B-77) The single-stranded oligonucleotide described in any of B-72) to B-76), wherein complementarity between the base sequence of nucleotides composing and the base sequence of nucleotides composing $Y^1$ is 70% or more.

B-78) The single-stranded oligonucleotide described in any of B-72) to B-77), wherein $X'^2$—$X'^3$-L'-$X^1$ and $Y^2$ hybridize within a molecule thereof.

B-79) The single-stranded oligonucleotide described in any of B-72) to B-78), wherein complementarity between the base sequence of nucleotides composing $X'^2$—$X'^3$-L'-$X^1$—$X^2$—$X^3$ and the base sequence of nucleotides composing $Y^2$ is 70% or more.

B-80) The single-stranded oligonucleotide described in any of B-56) to B-79), wherein $Y^2$ is a group derived from RNA.

B-81 The single-stranded oligonucleotide described in any of B-56) to B-71), wherein $Y^2$ represents a group derived from RNA composed of 10 to 13 ribonucleotides.

B-82) The single-stranded oligonucleotide described in any of B-1) to B-81), wherein L represents a group derived from DNA or RNA composed of 4 to 7 nucleotides.

C-1) The single-stranded oligonucleotide described in 1) represented by the formula $$X^1\text{—}X^2\text{—}X^3\text{-L-}Y^2\text{—}Y^1$$

(wherein, $X^1$ represents a group derived from an oligonucleotide composed of 2 or 3 LNA, $X^2$ represents a group derived from an oligonucleotide of a first nucleotide sequence portion that is composed of 8 to 10 deoxyribonucleotides, is a sequence that contains at least four contiguous nucleotides recognized by RNase H when hybridizing with a target RNA, and has an antisense sequence in the form of the first nucleotide sequence, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^2$ represents a group derived from an oligonucleotide of a second nucleotide sequence portion that is composed of 10 to 13 ribonucleotides, and $Y^1$ represents a group derived from an oligonucleotide composed of 2 or 3 2'-O-methyl nucleotides).

C-2) The single-stranded oligonucleotide described in 106) represented by the formula $$X^1\text{—}X^2\text{—}X^3\text{-L-}Y^2\text{—}Y^1\text{—B-A}$$

(wherein, $X^1$ represents a group derived from an oligonucleotide composed of 2 or 3 LNA, $X^2$ represents a group derived from an oligonucleotide of a first nucleotide sequence portion that is composed of 8 to 10 deoxyribonucleotides, is a sequence that contains at least four contiguous nucleotides recognized by RNase H when hybridizing with a target RNA, and has an antisense sequence in the form of the first nucleotide sequence, X³ represents a group derived from an oligonucleotide composed of 2 or 3 LNA, L represents a group derived from an oligonucleotide composed of 4 to 7 nucleotides independently selected from deoxyribonucleotides and ribonucleotides, Y² represents a group derived from an oligonucleotide of a second nucleotide sequence portion that is composed of 10 to 13 ribonucleotides, Y¹ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—), and A represents a group derived from a functional molecule).

C-3) The single-stranded oligonucleotide described in C-2), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-4) The single-stranded oligonucleotide described in C-2) or C-3), wherein B is coupled to a terminal nucleotide of Y¹ through a phosphodiester bond.

C-5) The single-stranded oligonucleotide described in any of C-1) to C-4), wherein nucleotides contained in X¹, X², X³ and Y¹ are mutually coupled through phosphorothioate bonds, and nucleotides contained in L and Y² are mutually coupled through phosphodiester bonds.

C-6) The single-stranded oligonucleotide described in any of C-1) to C-5), wherein each of the terminal nucleotides of X¹ and X², X² and X³ and Y² and Y¹ is coupled through a phosphorothioate bond, and each of the terminal nucleotides of X³ and L, and L and Y² is coupled through a phosphodiester bond.

C-7) The single-stranded oligonucleotide described in 75) represented by the formula

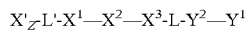

(wherein, X¹ represents a group derived from an oligonucleotide composed of 2 or 3 LNA, X² represents a group represented by an oligonucleotide that is a first nucleotide sequence portion, is composed of 8 to 10 deoxyribonucleotides, contains at least four contiguous nucleotides recognized by RNase H when hybridizing with a target RNA, and has an antisense sequence in the form of a first nucleotide sequence, X³ represents a group derived from an oligonucleotide composed of 2 or 3 LNA, X'$_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA, L represents a group derived from an oligonucleotide composed of 4 to 7 nucleotides independently selected from deoxyribonucleotides and ribonucleotides, L' represents a group derived from an oligonucleotide composed of 2 to 7 nucleotides independently selected from deoxyribonucleotides and ribonucleotides, Y² represents a group derived from an oligonucleotide that is a second nucleotide sequence portion and is composed of 10 to 13 ribonucleotides, and Y¹ represents a group derived from an oligonucleotide composed of 2 to 3 2'-O-methyl nucleotides).

C-8) The single-stranded oligonucleotide described in 106) represented by the formula

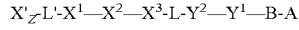

(wherein, X¹ represents a group derived from an oligonucleotide composed of 2 or 3 LNA, X² represents a group derived from an oligonucleotide that is a first nucleotide sequence portion, is composed of 8 to 10 deoxyribonucleotides, is a sequence containing at least four contiguous oligonucleotides recognized by RNase H when hybridizing with a target RNA, and has an antisense sequence in the form of a first nucleotide sequence, X³ represents a group derived from an oligonucleotide composed of 2 or 3 LNA, X'$_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA, L represents a group derived from an oligonucleotide composed of 4 to 7 nucleotides independently selected from deoxyribonucleotides and ribonucleotides, L' represents a group derived from an oligonucleotide composed of 2 to 7 nucleotides independently selected from deoxyribonucleotides and ribonucleotides, Y² represents a group derived from an oligonucleotide that is a second nucleotide sequence portion and is composed of 10 to 13 ribonucleotides, Y¹ represents a group derived from an oligonucleotide composed of 2 to 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—), and A represents a group derived from a functional molecule).

C-9) The single-stranded oligonucleotide described in C-8), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-10) The single-stranded oligonucleotide described in C-8) or C-9), wherein B is coupled to a terminal nucleotide of Y¹ through a phosphodiester bond.

C-11) The single-stranded oligonucleotide described in any of C-7) to C-10), wherein nucleotides contained in X¹, X², X³, X'$_Z$ and Y¹ are mutually coupled through phosphorothioate bonds, and nucleotides contained in L, L' and Y² are mutually coupled through phosphodiester bonds.

C-12) The single-stranded oligonucleotide described in any of C-7) to C-11), wherein each of the terminal nucleotides of $X^1$ and $X^2$, $X^2$ and $X^3$ and $Y^2$ and $Y^1$ is coupled through a phosphorothioate bond, and each of the terminal nucleotides of $X^3$ and L, L and $Y^2$ and L', $X'_Z$ and L' and L' and $X^1$ is coupled through a phosphodiester bond.

C-13) The single-stranded oligonucleotide described in any of C-7) to C-12), wherein $X_Z$ does not contain an oligonucleotide strand composed of four contiguous deoxyribonucleotides.

C-14) The single-stranded oligonucleotide described in C-13), wherein at least one nucleotide on the 3'-side and 5'-side of $X_Z$ is a nucleotide independently selected from a 2'-O-methyl nucleotide and LNA.

C-15) The single-stranded oligonucleotide described in C-13) or C-14), wherein nucleotides on the 3'-side and 5'-side of $X_Z$ are nucleotides independently selected from 2'-O-methyl nucleotides and LNA.

C-16) The single-stranded oligonucleotide described in any of C-13) to C-15), wherein $X_Z$ is a group derived from an oligonucleotide composed of nucleotides independently selected from 2'-O-methyl nucleotides and LNA.

C-17) The single-stranded oligonucleotide described in any of C-1) to C-16), wherein $X^1$ and $Y^1$ hybridize within a molecule thereof.

C-18) The single-stranded oligonucleotide described in any of C-1) to C-17), wherein complementarity between the base sequence of nucleotides composing $X^1$ and the base sequence of nucleotides composing $Y^1$ is 70% or more.

C-19) The single-stranded oligonucleotide described in any of C-1) to C-18), wherein $X^3$ and $Y^2$ hybridize within a molecule thereof.

C-20) The single-stranded oligonucleotide described in any of C-1) to C-19), wherein complementarity between the base sequence of nucleotides composing partial structure represented by the formula $X^2$—$X^3$ and the base sequence of nucleotides composing $Y^2$ is 70% or more.

C-21) The single-stranded oligonucleotide described in 75) represented by the formula

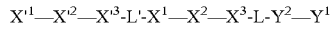

(wherein, $X^1$ represents a group derived from an oligonucleotide composed of 2 or 3 LNA, $X^2$ represents a group derived from an oligonucleotide that is a first nucleotide sequence portion, is composed of 8 to 10 deoxyribonucleotides, is a sequence containing at least four contiguous oligonucleotides recognized by RNase H when hybridizing with a target RNA, and has an antisense sequence in the form of a first nucleotide sequence, $X^3$ represents a group derived from an oligonucleotide composed of 2 or 3 LNA, $X'^1$ represents a group derived from an oligonucleotide composed of 2 or 3 LNA, $X'^2$ represents a group derived from an oligonucleotide that is an antisense sequence portion contained by X' in the form of a fourth nucleotide sequence portion, is composed of 8 to 10 deoxyribonucleotides, is a sequence containing at least four contiguous oligonucleotides recognized by RNase H when hybridizing with a target RNA, and has an antisense sequence in the form of a fourth nucleotide sequence, $X'^3$ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, $Y^2$ represents a group derived from an oligonucleotide that is a second nucleotide sequence portion and is composed of 10 to 13 ribonucleotides, and $Y^1$ represents a group derived from an oligonucleotide composed of 2 or 3 2'-O-methyl nucleotides).

C-22) The single-stranded oligonucleotide described in 106) represented by the formula

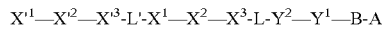

(wherein, $X^1$ represents a group derived from an oligonucleotide composed of 2 or 3 LNA, $X^2$ represents a group derived from an oligonucleotide that is a first nucleotide sequence portion, is composed of 8 to 10 deoxyribonucleotides, is a sequence containing at least four contiguous oligonucleotides recognized by RNase H when hybridizing with a target RNA, and has an antisense sequence in the form of a first nucleotide sequence, $X^3$ represents a group derived from an oligonucleotide composed of 2 or 3 LNA, $X'^1$ represents a group derived from an oligonucleotide composed of 2 or 3 LNA, $X'^2$ represents a group derived from an oligonucleotide that is an antisense sequence portion contained by X' in the form of a fourth nucleotide sequence portion, is composed of 8 to 10 deoxyribonucleotides, is a sequence containing at least four contiguous oligonucleotides recognized by RNase H when hybridizing with a target RNA, and has an antisense sequence in the form of a fourth nucleotide sequence, $X'^3$ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, $Y^2$ represents a group derived from an oligonucleotide of a second nucleotide sequence portion that is composed of 10 to 13 ribonucleotides, $Y^1$ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —$NR^B$— (wherein, $R^B$ represents a hydrogen atom, C1-6 alkyl group or halo-C1-6 alkyl group), —S—, —S(O)— or —S(O)$_2$—), and A represents a group derived from a functional molecule).

C-23) The single-stranded oligonucleotide described in C-22), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-24) The single-stranded oligonucleotide described in C-22) or C-23), wherein B is coupled to a terminal nucleotide of $Y^1$ through a phosphodiester bond.

C-25) The single-stranded oligonucleotide described in any of C-21) to C-24), wherein nucleotides contained in $X^1$, $X^2$, $X^3$, $X'^1$, $X'^2$, $X'^3$ and $Y^1$ are mutually coupled through phosphorothioate bonds, and nucleotides contained in L, L' and Y² are mutually coupled through phosphodiester bonds.

C-26) The single-stranded oligonucleotide described in any of C-21) to C-25), wherein each of the terminal nucleotides of $X^1$ and $X^2$, $X^2$ and $X^3$, $X'^1$ and $X'^2$, $X'^2$ and $X'^3$ and $Y^2$ and $Y^1$ is coupled through a phosphorothioate bond, and each of the terminal nucleotides of $X^3$ and L, L and $Y^2$, $X'^3$ and L' and L' and $X^1$ is coupled through a phosphodiester bond.

C-27) The single-stranded oligonucleotide described in any of C-21) to C-26), wherein $X^1$ and $Y^1$ hybridize within a molecule thereof.

C-28) The single-stranded oligonucleotide described in any of C-21) to C-27), wherein complementarity between the base sequence of nucleotides composing $X^1$ and the base sequence of nucleotides composing $Y^1$ is 70% or more.

C-29) The single-stranded oligonucleotide described in any of C-21) to C-28), wherein $X^3$ and $Y^2$ hybridize within a molecule thereof.

C-30) The single-stranded oligonucleotide described in any of C-21) to C-29), wherein complementarity between the base sequence of nucleotides composing partial structure represented by the formula $X^2$—$X^3$ and the base sequence of nucleotides composing $Y^2$ is 70% or more.

C-31) The single-stranded oligonucleotide described in 75) represented by the formula

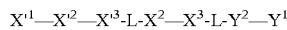

$$X'^1—X'^2—X'^3\text{-L-}X^2—X^3\text{-L-}Y^2—Y^1$$

(wherein, $X^1$ represents a group derived from an oligonucleotide composed of 2 or 3 LNA, $X^2$ represents a group derived from an oligonucleotide that is a first nucleotide sequence portion, is composed of 8 to 10 deoxyribonucleotides, is a sequence containing at least four contiguous oligonucleotides recognized by RNase H when hybridizing with a target RNA, and has an antisense sequence in the form of a first nucleotide sequence, $X^3$ represents a group derived from an oligonucleotide composed of 2 or 3 LNA, $X'^1$ represents a group derived from an oligonucleotide composed of 2 or 3 LNA, $X'^2$ represents a group derived from an oligonucleotide that is an antisense sequence portion contained by X' in the form of a fourth nucleotide sequence portion, is composed of 8 to 10 deoxyribonucleotides, is a sequence containing at least four contiguous oligonucleotides recognized by RNase H when hybridizing with a target RNA, and has an antisense sequence in the form of a fourth nucleotide sequence, $X'^3$ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, $Y^2$ represents a group derived from an oligonucleotide containing a second nucleotide sequence portion that is composed of 25 to 36 ribonucleotides, and $Y^1$ represents a group derived from an oligonucleotide composed of 2 or 3 2'-O-methyl nucleotides).

C-32) The single-stranded oligonucleotide described in 106) represented by the formula $$X'^1—X'^2—X'^3\text{-L-}X^2—X^3\text{-L-}Y^2—Y^1—B\text{-}A$$

(wherein, $X^1$ represents a group derived from an oligonucleotide composed of 2 or 3 LNA, $X^2$ represents a group derived from an oligonucleotide that is a first nucleotide sequence portion, is composed of 8 to 10 deoxyribonucleotides, is a sequence containing at least four contiguous oligonucleotides recognized by RNase H when hybridizing with a target RNA, and has an antisense sequence in the form of a first nucleotide sequence, $X^3$ represents a group derived from an oligonucleotide composed of 2 or 3 LNA, $X'^1$ represents a group derived from an oligonucleotide composed of 2 or 3 LNA, $X'^2$ represents a group derived from an oligonucleotide that is an antisense sequence portion contained by X' in the form of a fourth nucleotide sequence portion, is composed of 8 to 10 deoxyribonucleotides, is a sequence containing at least four contiguous oligonucleotides recognized by RNase H when hybridizing with a target RNA, and has an antisense sequence in the form of a fourth nucleotide sequence, $X'^3$ represents a group derived from an oligonucleotide composed of 2 or 3 LNA, L represents a group derived from an oligonucleotide composed of 4 to 7 nucleotides independently selected from deoxyribonucleotides and ribonucleotides, L' represents a group derived from an oligonucleotide composed of 3 to 7 nucleotides independently selected from deoxyribonucleotides and ribonucleotides, $Y^2$ represents a group derived from an oligonucleotide containing a second nucleotide sequence portion that is composed of 25 to 36 ribonucleotides, $Y^1$ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—), and A represents a group derived from a functional molecule).

C-33) The single-stranded oligonucleotide described in C-32), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-34) The single-stranded oligonucleotide described in C-32) or C-33), wherein B is coupled to a terminal nucleotide of $Y^1$ through a phosphodiester bond.

C-35) The single-stranded oligonucleotide described in any of C-31) to C-34), wherein nucleotides contained in $X^1$, $X^2$, $X^3$, $X'^1$, $X'^2$, $X'^3$ and $Y^1$ are mutually coupled through phosphorothioate bonds, and nucleotides contained in L, L' and $Y^2$ are mutually coupled through phosphodiester bonds.

C-36) The single-stranded oligonucleotide described in any of C-31) to C-35), wherein each of the terminal nucleotides of $X^1$ and $X^2$, $X^2$ and $X^3$, $X'^1$ and $X'^2$, $X'^2$ and $X'^3$ and $Y^2$ and $Y^1$ is coupled through a phosphorothioate bond, and each of the terminal nucleotides of $X^3$ and L, L and $Y^2$, $X'^3$ and L' and L' and $X^1$ is coupled through a phosphodiester bond.

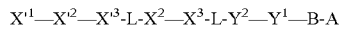

C-37) The single-stranded oligonucleotide described in any of C-31) to C-36), wherein $X^1$ and $Y^1$ hybridize within a molecule thereof.

C-38) The single-stranded oligonucleotide described in any of C-31) to C-37), wherein complementarity between the base sequence of nucleotides composing $X^1$ and the base sequence of nucleotides composing $Y^1$ is 70% or more.

C-39) The single-stranded oligonucleotide described in any of C-31) to C-38), wherein a partial structure represented by $X'^2$—$X'^3$-L'-$X'^1$—$X^2$ and $Y^2$ hybridize within a molecule thereof.

C-40) The single-stranded oligonucleotide described in any of C-31) to C-39), wherein complementarity between the base sequence of nucleotides composing a partial structure represented by the formula $X'^2$—$X'^3$-L'-$X^1$—$X^2$—$X^3$ and the base sequence of nucleotides composing $Y^2$ is 70% or more.

C-41) The single-stranded oligonucleotide described in any of C-1) to C-30), wherein $Y^2$ is a group derived from an oligonucleotide composed of 10 to 13 ribonucleotides.

C-42) The single-stranded oligonucleotide described in any of C-31) to C-40), wherein $Y^2$ is a group derived from RNA composed of 25 to 36 ribonucleotides.

C-43) The single-stranded oligonucleotide described in 1) represented by the formula $X^1$—$X^2$-L-$Y^0$—$Y_Z$ (wherein, $X^1$ represents a group derived from an oligonucleotide composed of 2 or 3 nucleotides independently selected from 2'-O-methyl nucleotides and LNA, $X^2$ represents a group derived from an oligonucleotide that is a first nucleotide sequence portion and is composed of 8 to 12 deoxyribonucleotides, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 10 to 15 ribonucleotides, and $Y_Z$ represents a group derived from an oligonucleotide that contains an antisense sequence portion, has at least one 2'-O-methyl nucleotide and LNA, and is composed of 10 to 20 nucleotides independently selected from deoxyribonucleotides, 2'-O-methyl nucleotides and LNA).

C-44) The single-stranded oligonucleotide described in 106) represented by the formula

A-B—$X^1$—$X^2$-L-$Y^0$—$Y_Z$ (wherein, A represents a group derived from a functional molecule, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —$NR^B$— (wherein, $R^B$ represents a hydrogen atom, C1-6 alkyl group or halo-C1-6 alkyl group), —S—, —S(O)— or —$S(O)_2$—), $X^1$ represents a group derived from an oligonucleotide composed of 2 or 3 nucleotides independently selected from 2'-O-methyl nucleotides and LNA, $X^2$ represents a group derived from an oligonucleotide that is a first nucleotide sequence portion and is composed of 8 to 12 deoxyribonucleotides, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 10 to 15 ribonucleotides, and $Y_Z$ represents a group derived from an oligonucleotide that contains an antisense sequence portion, has at least one 2'-O-methyl nucleotide and LNA, and is composed of 10 to 20 nucleotides independently selected from deoxyribonucleotides, 2'-O-methyl nucleotides and LNA).

C-45) The single-stranded oligonucleotide described in C-44), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-46) The single-stranded oligonucleotide described in C-44) or C-45), wherein B is coupled to a terminal nucleotide of $X^1$ through a phosphodiester bond.

C-47) The single-stranded oligonucleotide described in any of C-43) to C-46), wherein nucleotides contained in $X^1$, $X^2$ and $Y_Z$ are mutually coupled through a phosphorothioate bond, and nucleotides contained in L and $Y^0$ are mutually coupled through a phosphodiester bond.

C-48) The single-stranded oligonucleotide described in any of C-43) to C-47), wherein each of the terminal nucleotides of $X^1$ and $X^2$ is coupled through a phosphorothioate bond, and each of the terminal nucleotides of $X^2$ and L, L and $Y^0$, $Y^0$ and $Y_Z$ is coupled through a phosphodiester bond.

C-49) The single-stranded oligonucleotide described in any of C-43) to C-48), wherein $X^2$ and $Y^0$ hybridize within a molecule thereof.

C-50) The single-stranded oligonucleotide described in any of C-43) to C-49), wherein complementarity between the base sequence of nucleotides composing a partial structure represented by the formula $X^1$—$X^2$ and the base sequence of nucleotides composing $Y^0$ is 70% or more.

C-51) The single-stranded oligonucleotide described in any of C-43) to C-50), wherein $Y^0$ represents a group derived from RNA composed of 10 to 15 ribonucleotides.

C-52) The single-stranded oligonucleotide described in 1) represented by the formula $X^1$—$X^2$—$X^3$-L-$Y^0$—$Y_Z$ (wherein, $X^1$ represents a group derived from an oligonucleotide composed of 2 or 3 LNA, $X^2$ represents a group derived from an oligonucleotide that is a first nucleotide sequence portion and is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 12 to 16 ribonucleotides, and $Y_Z$ represents a group derived from an oligonucleotide that contains an antisense sequence portion, has at least one 2'-O-methyl nucleotide and LNA, and is composed of 10 to 20 nucleotides independently selected from deoxyribonucleotides, 2'-O-methyl nucleotides and LNA).

C-53) The single-stranded oligonucleotide described in C-52), wherein the first nucleotide sequence is an antisense sequence and is a sequence that contains at least four contiguous nucleotides recognized by RNase H when hybridizing with a target RNA.

C-54) The single-stranded oligonucleotide described in C-52) or C-53), wherein nucleotides contained in $X^1$, $X^2$, $X^3$ and $Y_Z$ are mutually coupled through phosphorothioate bonds, and nucleotides contained in L and $Y^0$ are mutually coupled through phosphodiester bonds.

C-55) The single-stranded oligonucleotide described in any of C-52) to C-54), wherein each of the terminal nucleotides of $X^1$ and $X^2$, and $X^2$ and $X^3$ is coupled through a phosphorothioate bond, and each of the terminal nucleotides of $X^3$ and L, L and $Y^0$ and $Y^0$ and $Y_Z$ is coupled through a phosphodiester bond.

C-56) The single-stranded oligonucleotide described in any of C-52) to C-55), wherein $X^2$ and $Y^0$ hybridize within a molecule thereof.

C-57) The single-stranded oligonucleotide described in any of C-52) to C-56), wherein complementarity between the base sequence of nucleotides composing a partial structure represented by the formula $X^1$—$X^2$—$X^3$ and the base sequence of nucleotides composing $Y^0$ is 70% or more.

C-58) The single-stranded oligonucleotide described in any of C-52) to C-57), wherein $Y^0$ represents a group derived from RNA composed of 12 to 16 ribonucleotides.

C-59) The single-stranded oligonucleotide described in any of C-43) to C-56), wherein a partial structure represented by the formula $Y_Z$ is represented by the formula $$Y_Z^3—Y_Z^2—Y_Z^1,$$

$Y_Z^1$ represents a group derived from an oligonucleotide composed of 2 or 3 LNA, $Y_Z^2$ represents a group derived from an oligonucleotide composed of 8 to 10 deoxyribonucleotides, and $Y_Z^3$ represents a group derived from an oligonucleotide composed or 2 or 3 LNA.

C-60) The single-stranded oligonucleotide described in any of C-43) to C-58), wherein $Y_Z$ does not contain an oligonucleotide strand composed of four contiguous deoxyribonucleotides.

C-61) The single-stranded oligonucleotide described in C-60), wherein a nucleotide of at least one of the 3'-side and 5'-side of $Y_Z$ is a nucleotide independently selected from a 2'-O-methyl nucleotide and LNA.

C-62) The single-stranded oligonucleotide described in C-60) or C-61), wherein nucleotides on the 3'-side and 5'-side of $Y_Z$ are nucleotides independently selected from 2'-O-methyl nucleotides and LNA.

C-63) The single-stranded oligonucleotide described in any of C-60) to C-62), wherein $Y_Z$ is a group derived from an oligonucleotide composed of nucleotides independently selected from 2'-O-methyl nucleotides and LNA.

C-64) The single-stranded oligonucleotide described in 1), represented by the formula $$X^4—X^5—X^1—X^2—X^3\text{-L-}Y^0—Y_Z^3—Y_Z^2—Y_Z^1$$

(wherein, $X^4$ represents a group derived from an oligonucleotide that is composed of 2 or 3 2'-O-methyl nucleotides, $X^5$ represents a group derived from an oligonucleotide composed of 10 to 13 ribonucleotides, $X^1$ represents a group derived from an oligonucleotide composed 2 or 3 LNA, $X^2$ represents a group derived from an oligonucleotide that is a first nucleotide sequence portion and is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 12 to 16 ribonucleotides, $Y_Z^3$ represents a group derived from an oligonucleotide composed of 2 or 3 LNA, $Y_Z^2$ represents a group derived from an oligonucleotide that is an antisense sequence portion contained by Y and is composed of 8 to 10 deoxyribonucleotides, and $Y_Z^1$ represents a group derived from an oligonucleotide composed or 2 or 3 LNA).

C-65) The single-stranded oligonucleotide described in C-64), wherein the first nucleotide sequence is an antisense sequence and is a sequence that contains at least four contiguous nucleotides recognized by RNase H when hybridizing with a target RNA.

C-66) The single-stranded oligonucleotide described in 106), represented by the formula $$\text{A-B}—X^4—X^5—X^1—X^2—X^3\text{-L-}Y^0—Y_Z^3—Y_Z^2—Y_Z^1$$

(wherein, A represents a group derived from a functional molecule,

B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —NR$^B$— (wherein, R$^B$ represents a hydrogen atom, C1-6 alkyl group or halo-C1-6 alkyl group), —S—, —S(O)— or —S(O)$_2$—), $X^4$ represents a group derived from an oligonucleotide that is composed of 2 or 3 2'-O-methyl nucleotides, $X^5$ represents a group derived from an oligonucleotide composed of 10 to 13 ribonucleotides, $X^1$ represents a group derived from an oligonucleotide composed 2 or 3 LNA, $X^2$ represents a group derived from an oligonucleotide that is a first nucleotide sequence portion and is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 12 to 16 ribonucleotides, $Y_Z^3$ represents a group derived from an oligonucleotide composed of 2 or 3 LNA, $Y_Z^2$ represents a group derived from an oligonucleotide that is an antisense sequence portion contained by Y and is composed of 8 to 10 deoxyribonucleotides, and $Y_Z^1$ represents a group derived from an oligonucleotide composed or 2 or 3 LNA).

C-67) The single-stranded oligonucleotide described in C-66), wherein the first nucleotide sequence is an antisense sequence and is a sequence that contains at least four contiguous nucleotides recognized by RNase H when hybridizing with a target RNA.

C-68) The single-stranded oligonucleotide described in C-66) or C-67), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-69) The single-stranded oligonucleotide described in any of C-66) or C-68), wherein B is coupled to a terminal nucleotide of $X^4$ through a phosphodiester bond.

C-70) The single-stranded oligonucleotide described in any of C-64) to C-69), wherein nucleotides contained in $X^4$, $X^1$, $X^2$, $X^3$, $Y_Z^3$, $Y_Z^2$ and $Y_Z^1$ are mutually coupled through phosphorothioate bonds, and nucleotides contained in $X^5$, L and $Y^0$ are mutually coupled through phosphodiester bonds.

C-71) The single-stranded oligonucleotide described in any of C-64) to C-70), wherein each of the terminal nucleotides of $X^4$ and $X^5$, $X^1$ and $X^2$ and $X^2$ and $X^3$ is coupled through a phosphorothioate bond, and each of the terminal nucleotides of $X^5$ and $X^1$, $X^3$ and L, L and $Y^0$ and $Y^0$ and $Y_Z^3$ is coupled through a phosphodiester bond.

C-72) The single-stranded oligonucleotide described in any of C-64) to C-71), wherein $X^2$ and $Y^0$ hybridize within a molecule thereof.

C-73) The single-stranded oligonucleotide described in any of C-64) to C-72), wherein complementarity between the base sequence of nucleotides composing a partial structure represented by the formula $X^1$—$X^2$—$X^3$ and the base sequence of nucleotides composing $Y^0$ is 70% or more.

C-74) The single-stranded oligonucleotide described in any of C-64) to C-73), wherein $X^5$ and $Y_Z^2$ hybridize within a molecule thereof.

C-75) The single-stranded oligonucleotide described in any of C-64) to C-74), wherein complementarity between the base sequence of nucleotides composing $X^5$ and the base sequence of nucleotides composing a partial structure represented by the formula $Y_Z^2$—$Y_Z^3$ is 70% or more.

C-76) The single-stranded oligonucleotide described in any of C-64) to C-75), wherein $X^4$ and $Y_Z^1$ hybridize within a molecule thereof.

C-77) The single-stranded oligonucleotide described in any of C-64) to C-76), wherein complementarity between the base sequence of nucleotides composing $X^4$ and the base sequence of nucleotides composing $Y_Z^1$ is 70% or more.

C-78) The single-stranded oligonucleotide described in any of C-64) to C-77), wherein $X^5$ represents a group derived from RNA composed of 10 to 13 ribonucleotides.

C-79) The single-stranded oligonucleotide described in any of C-52) to C-78), wherein $Y^0$ represents a group derived from RNA composed of 12 to 16 ribonucleotides.

C-80) The single-stranded oligonucleotide described in 1), represented by the formula $$X^4\text{—}X^5\text{—}X^1\text{—}X^2\text{—}X^3\text{-L-}Y^0\text{—}Y_Z^3\text{—}Y_Z^2\text{—}Y_Z^1$$

(wherein, $X^4$ represents a group derived from an oligonucleotide that is composed of 2 or 3 2'-O-methyl nucleotides, $X^5$ represents a group derived from an oligonucleotide composed of 12 to 19 ribonucleotides, $X^1$ represents a group derived from an oligonucleotide composed 2 or 3 LNA, $X^2$ represents a group derived from an oligonucleotide that is a first nucleotide sequence portion and is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 14 to 22 ribonucleotides, $Y_Z^3$ represents a group derived from an oligonucleotide composed of 2 or 3 LNA, $Y_Z^2$ represents a group derived from an oligonucleotide that is an antisense sequence portion contained by Y and is composed of 8 to 10 deoxyribonucleotides, and $Y_Z^1$ represents a group derived from an oligonucleotide composed or 2 or 3 LNA).

C-81) The single-stranded oligonucleotide described in C-74), wherein the first nucleotide sequence is an antisense sequence and is a sequence that contains at least four contiguous nucleotides recognized by RNase H when hybridizing with a target RNA.

C-82) The single-stranded oligonucleotide described in 106), represented by the formula $$\text{A-B—}X^4\text{—}X^5\text{—}X^1\text{—}X^2\text{—}X^3\text{-L-}Y^0\text{—}Y_Z^3\text{—}Y_Z^2\text{—}Y_Z^1$$

(wherein, A represents a group derived from a functional molecule,

B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —$NR^B$— (wherein, $R^B$ represents a hydrogen atom, C1-6 alkyl group or halo-C1-6 alkyl group), —S—, —S(O)— or —S(O)$_2$—), $X^4$ represents a group derived from an oligonucleotide that is composed of 2 or 3 2'-O-methyl nucleotides, $X^5$ represents a group derived from an oligonucleotide composed of 12 to 19 ribonucleotides, $X^1$ represents a group derived from an oligonucleotide composed 2 or 3 LNA, $X^2$ represents a group derived from an oligonucleotide that is a first nucleotide sequence portion and is composed of 8 to 10 deoxyribonucleotides, $X^3$ represents a group derived from an oligonucleotide composed of 2 or 3 LNA, L represents a group derived from an oligonucleotide composed of 4 to 7 nucleotides independently selected from deoxyribonucleotides and ribonucleotides, $Y^0$ represents a group derived from an oligonucleotide that is a second nucleotide sequence portion and is composed of 14 to 22 ribonucleotides, $Y_Z^3$ represents a group derived from an oligonucleotide composed of 2 or 3 LNA, $Y_Z^2$ represents a group derived from an oligonucleotide that is an antisense sequence portion contained by Y and is composed of 8 to 10 deoxyribonucleotides, and $Y_Z^1$ represents a group derived from an oligonucleotide composed or 2 or 3 LNA).

C-83) The single-stranded oligonucleotide described in C-82), wherein the first nucleotide sequence is an antisense sequence and is a sequence that contains at least four contiguous nucleotides recognized by RNase H when hybridizing with a target RNA.

C-84) The single-stranded oligonucleotide described in C-82) or C-83), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-85) The single-stranded oligonucleotide described in any of C-82) or C-84), wherein B is coupled to a terminal nucleotide of $X^4$ through a phosphodiester bond.

C-86) The single-stranded oligonucleotide described in any of C-80) to C-85), wherein nucleotides contained in $X^4$, $X^1$, $X^2$, $X^3$, $Y_Z^3$, $Y_Z^2$ and $Y_Z^1$ are mutually coupled through phosphorothioate bonds, and nucleotides contained in $X^5$, L and $Y^0$ are mutually coupled through phosphodiester bonds.

C-87) The single-stranded oligonucleotide described in any of C-80) to C-86), wherein each of the terminal nucleotides of $X^4$ and $X^5$, $X^1$ and $X^2$ and $X^2$ and $X^3$ is coupled through a phosphorothioate bond, and each of the terminal nucleotides of $X^5$ and $X^1$, $X^3$ and L, L and $Y^0$ and $Y^0$ and $Y_Z^3$ is coupled through a phosphodiester bond.

C-88) The single-stranded oligonucleotide described in any of C-80) to C-87), wherein $X^2$ and $Y^0$ hybridize within a molecule thereof.

C-89) The single-stranded oligonucleotide described in any of C-80) to C-88), wherein complementarity between the base sequence of nucleotides composing a partial structure represented by the formula $X^1$—$X^2$—$X^3$ and the base sequence of nucleotides composing $Y^0$ is 70% or more.

C-90) The single-stranded oligonucleotide described in any of C-80) to C-89), wherein $X^5$ and $Y_Z^2$ hybridize within a molecule thereof.

C-91) The single-stranded oligonucleotide described in any of C-80) to C-90), wherein complementarity between the base sequence of nucleotides composing $X^5$ and the base sequence of nucleotides composing a partial structure represented by the formula $Y_Z^2$—$Y_Z^3$ is 70% or more.

C-92) The single-stranded oligonucleotide described in any of C-80) to C-91), wherein a portion of $X^5$ and a portion of $Y^0$ hybridize within a molecule thereof.

C-93) The single-stranded oligonucleotide described in any of C-80) to C-92), wherein complementarity between the base sequence of nucleotides composing a portion of $X^5$ and the base sequence of nucleotides composing a portion of $Y^0$ is 70% or more.

C-94) The single-stranded oligonucleotide described in any of C-80) to C-93), wherein $X^4$ and $Y_Z^1$ hybridize within a molecule thereof.

C-95) The single-stranded oligonucleotide described in any of C-80) to C-94), wherein complementarity between the base sequence of nucleotides composing $X^4$ and the base sequence of nucleotides composing $Y_Z^1$ is 70% or more.

C-96) The single-stranded oligonucleotide described in any of C-80) to C-95), wherein $X^5$ represents a group derived from RNA composed of 12 to 19 ribonucleotides.

C-97) The single-stranded oligonucleotide described in any of C-80) to C-96), wherein $Y^0$ represents a group derived from RNA composed of 14 to 22 ribonucleotides.

C-98) The single-stranded oligonucleotide described in 1), represented by the formula $$X_Z\text{—}X^0\text{—}X^2\text{-L-}Y^2\text{—}Y^1$$

(wherein, $X_Z$ represents a group derived from an oligonucleotide that contains an antisense sequence portion, has at least one 2'-O-methyl nucleotide and LNA, and is composed of 10 to 20 nucleotides independently selected from deoxyribonucleotides, 2'-O-methyl nucleotides and LNA, $X^0$ represents a group derived from an oligonucleotide composed of 2 to 5 nucleotides independently selected from deoxyribonucleotides and ribonucleotides, $X^2$ represents a group derived from an oligonucleotide that is a first nucleotide sequence portion and is composed of 8 to 17 deoxyribonucleotides, L represents a group derived from an oligonucleotide composed of 4 to 7 nucleotides independently selected from deoxyribonucleotides and ribonucleotides, $Y^2$ represents a group derived from an oligonucleotide that is a second nucleotide sequence portion and is composed of 8 to 19 ribonucleotides, and $Y^1$ represents a group derived from an oligonucleotide composed of 2 or 3 2'-O-methyl nucleotides).

C-99) The single-stranded oligonucleotide described in 106), represented by the formula $$X_Z\text{—}X^0\text{—}X^2\text{-L-}Y^2\text{—}Y^1\text{—}B\text{-A}$$

(wherein, $X_Z$ represents a group derived from an oligonucleotide that contains an antisense sequence portion, has at least one 2'-O-methyl nucleotide and LNA, and is composed of 10 to 20 nucleotides independently selected from deoxyribonucleotides, 2'-O-methyl nucleotides and LNA, $X^0$ represents a group derived from an oligonucleotide composed of 2 to 5 nucleotides independently selected from deoxyribonucleotides and ribonucleotides, $X^2$ represents a group derived from an oligonucleotide that is a first nucleotide sequence portion and is composed of 8 to 17 deoxyribonucleotides, L represents a group derived from an oligonucleotide composed of 4 to 7 nucleotides independently selected from deoxyribonucleotides and ribonucleotides, $Y^2$ represents a group derived from an oligonucleotide that is a second nucleotide sequence portion and is composed of 8 to 19 ribonucleotides, $Y^1$ represents a group derived from an oligonucleotide composed of 2 or 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —$NR^B$— (wherein, $R^B$ represents a hydrogen atom, C1-6 alkyl group or halo-C1-6 alkyl group), —S—, —S(O)— or —S(O)$_2$—), and A represents a group derived from a functional molecule).

C-100) The single-stranded oligonucleotide described in C-99), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-101) The single-stranded oligonucleotide described in any of C-99) or C-100), wherein B is coupled to a terminal nucleotide of $Y^1$ through a phosphodiester bond.

C-102) The single-stranded oligonucleotide described in any of C-98) to C-101), wherein nucleotides contained in $X_Z$, $X^2$ and $Y^1$ are mutually coupled through phosphorothioate bonds, and nucleotides contained in $X^0$, L and $Y^2$ are mutually coupled through phosphodiester bonds.

C-103) The single-stranded oligonucleotide described in any of C-98) to C-102), wherein each of the terminal nucleotides of $Y^2$ and $Y^1$ is coupled through a phosphorothioate bond, and each of the terminal nucleotides of $X_Z$ and $X^0$, $X^0$ and $X^2$, $X^2$ and L, and L and $Y^2$ is coupled through a phosphodiester bond.

C-104) The single-stranded oligonucleotide described in any of C-98) to C-103), wherein $X^0$ and $Y^1$ hybridize within a molecule thereof.

C-105) The single-stranded oligonucleotide described in any of C-98) to C-104), wherein complementarity between the base sequence of nucleotides composing $X^0$ and the base sequence of nucleotides composing $Y^1$ is 70% or more.

C-106) The single-stranded oligonucleotide described in any of C-98) to C-105), wherein $X^2$ and $Y^2$ hybridize within a molecule thereof.

C-107) The single-stranded oligonucleotide described in any of C-98) to C-106), wherein complementarity between the base sequence of nucleotides composing $X^2$ and the base sequence of nucleotides composing $Y^2$ is 70% or more.

C-108) The single-stranded oligonucleotide described in any of C-98) to C-107), wherein $X_Z$ does not contain an oligonucleotide strand composed of four contiguous deoxyribonucleotides.

C-109) The single-stranded oligonucleotide described in any of C-98 to C-108), wherein a nucleotide of at least one of the 3'-end and 5'-end of $X_Z$ is a nucleotide independently selected from a 2'-O-methyl nucleotide and LNA.

C-110) The single-stranded oligonucleotide described in any of C-98) to C-109), wherein nucleotides on the 3'-end and 5'-end of $X_Z$ are nucleotides independently selected from 2'-O-methyl nucleotides and LNA.

C-111) The single-stranded oligonucleotide described in any of C-98) to C-107), wherein the partial structure represented by the formula $X_Z$— is represented by the formula

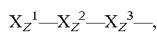

$X_Z^1$ represents a group derived from an oligonucleotide composed of 2 or 3 LNA, $X_Z^2$ represents a group derived from an oligonucleotide that is an antisense sequence portion and is composed of 8 to 10 deoxyribonucleotides, and $X_Z^3$ represents a group derived from an oligonucleotide composed of 2 or 3 LNA.

C-112) The single-stranded oligonucleotide described in any of C-98) to C-107), wherein $X_Z$ represents a group derived from an oligonucleotide composed of nucleotides independently selected from 2'-O-methyl nucleotides and LNA.

C-113) The single-stranded oligonucleotide described in any of C-98) to

C-112), wherein $Y^2$ represents a group derived from RNA composed of 8 to 19 ribonucleotides.

C-114) The single-stranded oligonucleotide described in 1) represented by the formula $$X_Z\text{—}X^2\text{—}X^3\text{-L-}Y^3\text{—}Y^2\text{—}Y^1$$

(wherein, $X_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA, $X^2$ represents a group represented by an oligonucleotide composed of 4 to 8 nucleotides independently selected from ribonucleotides, $X^3$ represents a group derived from an oligonucleotide that is a first nucleotide sequence portion and is composed of 4 to 8 deoxyribonucleotides, L represents a group derived from an oligonucleotide composed of 4 to 7 nucleotides independently selected from deoxyribonucleotides and ribonucleotides, $Y^3$ represents a group derived from an oligonucleotide that is a second nucleotide sequence portion and is composed of 4 to 8 ribonucleotides, $Y^2$ represents a group derived from an oligonucleotide composed of 4 to 8 deoxyribonucleotides, and $Y^1$ represents a group derived from an oligonucleotide composed of 2 to 3 2'-O-methyl nucleotides).

C-115) The single-stranded oligonucleotide described in 106), represented by the formula $$X_Z\text{—}X^2\text{—}X^3\text{-L-}Y^3\text{—}Y^2\text{—}Y^1\text{—}B\text{-A}$$

(wherein, $X_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA, $X^2$ represents a group represented by an oligonucleotide composed of 4 to 8 nucleotides independently selected from ribonucleotides, $X^3$ represents a group derived from an oligonucleotide that is a first nucleotide sequence portion and is composed of 4 to 8 deoxyribonucleotides, L represents a group derived from an oligonucleotide composed of 4 to 7 nucleotides independently selected from deoxyribonucleotides and ribonucleotides, $Y^3$ represents a group derived from an oligonucleotide that is a second nucleotide sequence portion and is composed of 4 to 8 ribonucleotides, $Y^2$ represents a group derived from an oligonucleotide composed of 4 to 8 deoxyribonucleotides, $Y^1$ represents a group derived from an oligonucleotide composed of 2 to 3 2'-O-methyl nucleotides, B represents a C2-20 alkylene group or C2-20 alkenylene group (methylene groups contained in the alkylene group and alkenylene group are respectively and independently unsubstituted or substituted with one or more substituents selected from the group consisting of a halogen atom, hydroxyl group, protected hydroxyl group, oxo group and thioxo group, and methylene groups of the alkylene group and alkenylene group are respectively and independently not-replaced or replaced with —O—, —$NR^B$— (wherein, $R^B$ represents a hydrogen atom, C1-6 alkyl group or halo-C1-6 alkyl group), —S—, —S(O)— or —S(O)$_2$—), and A represents a group derived from a functional molecule).

C-116) The single-stranded oligonucleotide described in C-99), wherein B represents a C2-20 alkylene group (methylene groups of the alkylene group are respectively and independently not-replaced or replaced with —O—, and not-replaced methylene groups are respectively and independently unsubstituted or substituted with a hydroxyl group), and A represents a group derived from tocopherol.

C-117) The single-stranded oligonucleotide described in any of C-115) or C-116), wherein B is coupled to a terminal nucleotide of $Y^1$ through a phosphodiester bond.

C-118) The single-stranded oligonucleotide described in any of C-114) to C-117), wherein nucleotides contained in $X_Z$, $X^3$, $Y^2$ and $Y^1$ are mutually coupled through phosphorothioate bonds, and nucleotides contained in $X^2$, L and $Y^3$ are mutually coupled through phosphodiester bonds.

C-119) The single-stranded oligonucleotide described in any of C-114) to C-118), wherein each of the terminal nucleotides of $Y^3$ and $Y^2$, $Y^2$ and $Y^1$, and $X^2$ and $X^3$ is coupled through a phosphorothioate bond, and each of the terminal nucleotides of $X_Z$ and $X^3$, $X^3$ and L, and L and $Y^3$ is coupled through a phosphodiester bond.

C-120) The single-stranded oligonucleotide described in any of C-114) to C-119), wherein $X^2$ and $Y^2$ hybridize within a molecule thereof.

C-121) The single-stranded oligonucleotide described in any of C-114) to C-120), wherein complementarity between the base sequence of nucleotides composing $X^2$ and the base sequence of nucleotides composing $Y^2$ is 70% or more, and complementarity between the base sequence of nucleotides composing $X^3$ and the base sequence of nucleotides composing $Y^3$ is 70% or more.

C-122) The single-stranded oligonucleotide described in any of C-114) to C-121), wherein $X^2$ and $Y^1$ hybridize within a molecule thereof.

C-123) The single-stranded oligonucleotide described in any of C-114) to C-122), wherein complementarity between the base sequence of nucleotides composing $X^2$ and the base sequence of nucleotides composing $Y^1$ is 70% or more.

C-124) The single-stranded oligonucleotide described in any of C-114) to C-123), wherein $X_Z$ does not contain an oligonucleotide strand composed of four contiguous deoxyribonucleotides.

C-125) The single-stranded oligonucleotide described in any of C-114 to C-124), wherein a nucleotide of at least one of the 3'-end and 5'-end of $X_Z$ is a nucleotide independently selected from a 2'-O-methyl nucleotide and LNA.

C-126) The single-stranded oligonucleotide described in any of C-114) to C-125), wherein nucleotides on the 3'-end and 5'-end of $X_Z$ are nucleotides independently selected from 2'-O-methyl nucleotides and LNA.

C-127) The single-stranded oligonucleotide described in any of C-114) to C-123), wherein the partial structure represented by the formula $X_Z-$ is represented by the formula

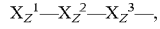

$X_Z^1-X_Z^2-X_Z^3-$, $X_Z^1$ represents a group derived from an oligonucleotide composed of 2 or 3 LNA, $X_Z^2$ represents a group derived from an oligonucleotide that is an antisense sequence portion and is composed of 8 to 10 deoxyribonucleotides, and $X_Z^3$ represents a group derived from an oligonucleotide composed of 2 or 3 LNA.

C-128) The single-stranded oligonucleotide described in any of C-114) to C-123), wherein $X_Z$ represents a group derived from an oligonucleotide composed of nucleotides independently selected from 2'-O-methyl nucleotides and LNA.

C-129) The single-stranded oligonucleotide described in any of 1) to 167) and C-1) to C-128), wherein the base moiety in a deoxyribonucleotide, ribonucleotide and sugar-modified nucleotide is at least one type selected from the group consisting of adenine (A), guanine (G), thymine (T), cytosine (C), uracil (U) and 5-methylcytosine (5-me-C).

C-130) The single-stranded oligonucleotide described in any of 1) to 167) and C-1) to C-129), wherein L represents a group derived from DNA or RNA composed of 4 to 7 nucleotides.

C-131) The single-stranded oligonucleotide described in any of 1) to 167) and C-1) to C-130), wherein the third oligonucleotide is composed of 4 or 5 nucleotides independently selected from deoxyribonucleotides and ribonucleotides.

C-132) The single-stranded oligonucleotide described in any of 1) to 167) and C-1) to C-131), wherein the third oligonucleotide is an oligonucleotide composed of adenosine.

D-1) A pharmaceutical containing as an active ingredient thereof the single-stranded oligonucleotide described in any of 1) to 167) and C-1) to C-132).

D-2) A pharmaceutical containing as an active ingredient thereof the single-stranded oligonucleotide described in any of B-1) to B-82).

A conceptual diagram of the single-stranded oligonucleotide described in B-60) or C-1), in which a first nucleotide sequence is an antisense sequence, and the first nucleotide sequence portion and a second nucleotide sequence portion hybridize within a molecule thereof, is shown in FIG. 1. In the single-stranded oligonucleotide shown in FIG. 1, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^2$ composed of 10 to 13 ribonucleotides and having the second nucleotide sequence, and $Y^1$ composed of 2 or 3 2'-O-methyl nucleotides, are bound in this order. The direction of bonding from $X^1$ to $Y^1$ may be in the 5' to 3' direction or in the 3' to 5' direction. In FIG. 1, $X^2$ having the first nucleotide sequence and $Y^2$ having the second nucleotide sequence form a double strand. Although $X^1$ and $Y^1$ may or may not form a double strand, they preferably form a double strand. Although $X^3$ and $Y^2$ may or may not form a double strand, they preferably form a double strand.

Figure 2:
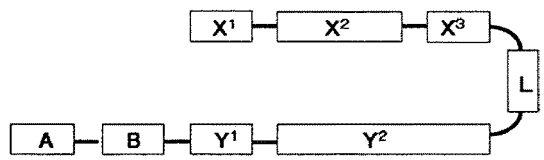
FIG. 2 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in B-61) or C-2), in which a first nucleotide sequence is an antisense sequence, and the first nucleotide sequence portion and a second nucleotide sequence portion hybridize within a molecule thereof, is shown in FIG. 2. In the single-stranded oligonucleotide shown in FIG. 2, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^2$ composed of 10 to 13 ribonucleotides and having the second nucleotide sequence, $Y^1$ composed of 2 or 3 2'-O-methyl nucleotides, B in the form of a C2-20 alkylene group and the like, and A in the form of a group derived from a functional molecule, are bound in this order. The direction of bonding from $X^1$ to $Y^1$ may be in the 5' to 3' direction or in the 3' to 5' direction. In FIG. 2, $X^2$ having the first nucleotide sequence and $Y^2$ having the second nucleotide sequence form a double strand. Although $X^1$ and $Y^1$ may or may not form a double strand, they preferably form a double strand. Although $X^3$ and $Y^2$ may or may not form a double strand, they preferably form a double strand.

Figure 3:
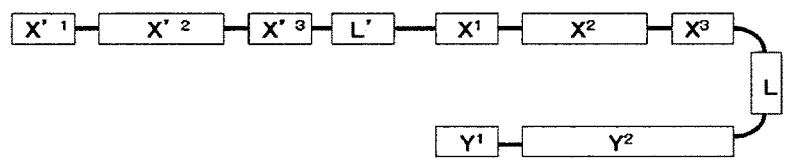
FIG. 3 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in B-64) or C-21), in which a first nucleotide sequence is an antisense sequence, and the first nucleotide sequence portion and a second nucleotide sequence portion hybridize within a molecule thereof, is shown in FIG. 3. In the single-stranded oligonucleotide shown in FIG. 3, $X'^1$ composed of 2 or 3 LNA, $X'^2$ composed of 8 to 10 deoxyribonucleotides and having a fourth nucleotide sequence, $X'^3$ composed of 2 or 3 LNA, L' composed of 3 to 7 nucleotides independently selected from deoxyribonucleotides and ribonucleotides, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^2$ composed of 10 to 13 ribonucleotides and having the second nucleotide sequence, and $Y^1$ composed of 2 or 3 2'-O-methyl nucleotides, are bound in this order. The direction of bonding from to $Y^1$ may be in the 5' to 3' direction or in the 3' to 5' direction. In FIG. 3, $X^2$ having the first nucleotide sequence and $Y^2$ having the second nucleotide sequence form a double strand.

Although $X^1$ and $Y^1$ may or may not form a double strand, they preferably form a double strand. Although $X^3$ and $Y^2$ may or may not form a double strand, they preferably form a double strand.

Figure 4:
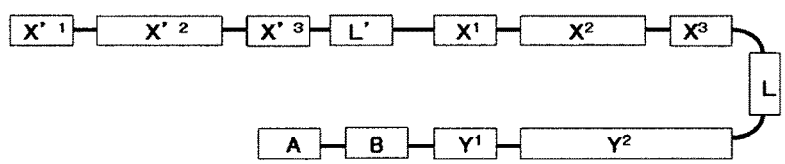
FIG. 4 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in B-65) or C-22), in which a first nucleotide sequence is an antisense sequence, and the first nucleotide sequence portion and a second nucleotide sequence portion hybridize within a molecule thereof, is shown in FIG. 4. In the single-stranded oligonucleotide shown in FIG. 4, $X'^1$ composed of 2 or 3 LNA, $X'^2$ composed of 8 to 10 deoxyribonucleotides and having a fourth nucleotide sequence, $X'^3$ composed of 2 or 3 LNA, L' composed of 3 to 7 nucleotides independently selected from deoxyribonucleotides and ribonucleotides, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^2$ composed of 10 to 13 ribonucleotides and having the second nucleotide sequence, $Y^1$ composed of 2 or 3 2'-O-methyl nucleotides, B in the form of a C2-20 alkylene group and the like, and A in the form of a group derived from a functional molecule, are bound in this order. The direction of bonding from $X'^1$ to $Y^1$ may be in the 5' to 3' direction or in the 3' to 5' direction. In FIG. 4, $X^2$ having the first nucleotide sequence and $Y^2$ having the second nucleotide sequence form a double strand. Although $X^1$ and $Y^1$ may or may not form a double strand, they preferably form a double strand. Although $X^3$ and $Y^2$ may or may not form a double strand, they preferably form a double strand.

Figure 5:
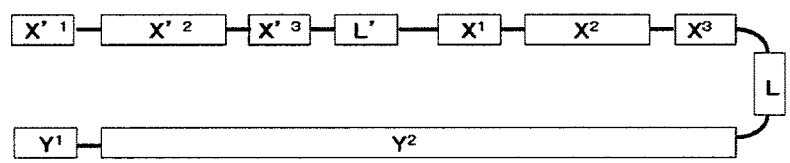
FIG. 5 is a conceptual diagram representing one aspect in which a first nucleotide sequence portion $X^2$ and an antisense sequence portion $X'^2$ contained by X' of an example of the present embodiment in the form of a single-stranded oligonucleotide respectively hybridize with a $Y^2$ containing a second nucleotide sequence portion and a sixth nucleotide sequence portion within a molecule thereof.

A conceptual diagram of the single-stranded oligonucleotide described in B-72) or C-31), in which a first nucleotide sequence is an antisense sequence, the first nucleotide sequence portion and a second nucleotide sequence portion hybridize within a molecule thereof, and a fourth nucleotide sequence and a sixth nucleotide sequence hybridize within a molecule thereof, is shown in FIG. 5. In the single-stranded oligonucleotide shown in FIG. 5, $X'^1$ composed of 2 or 3 LNA, $X'^2$ composed of 8 to 10 deoxyribonucleotides and having the fourth nucleotide sequence, $X'^3$ composed of 2 or 3 LNA, L' composed of 3 to 7 nucleotides independently selected from deoxyribonucleotides and ribonucleotides, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^2$ composed of 25 to 36 ribonucleotides and having the second nucleotide sequence and the sixth nucleotide sequence, and $Y^1$ composed of 2 or 3 2'-O-methyl nucleotides, are bound in this order. The direction of bonding from $X'^1$ to $Y^1$ may be in the 5' to 3' direction or in the 3' to 5' direction. In FIG. 5, $X^2$ having the first nucleotide sequence and a portion of $Y^2$ having the second nucleotide sequence form a double strand, and $X'^2$ having the fourth nucleotide sequence and a portion of $Y^2$ having the sixth nucleotide sequence form a double strand. Although $X'^1$ and $Y^1$ may or may not form a double strand, they preferably form a double strand. Although $X'^3$, $X^3$, L' and $X^1$ may or may not respectively and independently form a double strand with $Y^2$, they preferably form a double strand. In addition, the second nucleotide sequence and the sixth nucleotide sequence may be the same or different.

Figure 6:
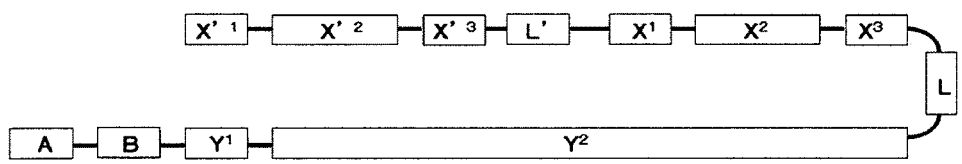
FIG. 6 is a conceptual diagram representing one aspect in which a first nucleotide sequence portion $X^2$ and an antisense sequence portion $X'^2$ contained by X' of an example of the present embodiment in the form of a single-stranded oligonucleotide respectively hybridize with a $Y^2$ containing a second nucleotide sequence portion and a sixth nucleotide sequence portion within a molecule thereof.

A conceptual diagram of the single-stranded oligonucleotide described in B-73) or C-32), in which a first nucleotide sequence is an antisense sequence, the first nucleotide sequence portion and a second nucleotide sequence portion hybridize within a molecule thereof, and a fourth nucleotide sequence and a sixth nucleotide sequence hybridize within a molecule thereof, is shown in FIG. 6. In the single-stranded oligonucleotide shown in FIG. 6, $X'^1$ composed of 2 or 3 LNA, $X'^2$ composed of 8 to 10 deoxyribonucleotides and having the fourth nucleotide sequence, $X'^3$ composed of 2 or 3 LNA, L' composed of 3 to 7 nucleotides independently selected from deoxyribonucleotides and ribonucleotides, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^2$ composed of 25 to 36 ribonucleotides and having the second nucleotide sequence, $Y^1$ composed of 2 or 3 2'-O-methyl nucleotides, B in the form of a C2-20 alkylene group and the like, and A in the form of a group derived from a functional molecule, are bound in this order. The direction of bonding from to $Y^1$ may be in the 5' to 3' direction or in the 3' to 5' direction. In FIG. 6, $X^2$ having the first nucleotide sequence and a portion of $Y^2$ having the second nucleotide sequence form a double strand, and $X'^2$ having the fourth nucleotide sequence and a portion of $Y^2$ having the sixth nucleotide sequence form a double strand. Although and $Y^1$ may or may not form a double strand, they preferably form a double strand. Although $X'^3$, $X^3$, L' and $X^1$ may or may not respectively and independently form a double strand with $Y^2$, they preferably form a double strand. In addition, the second nucleotide sequence and the sixth nucleotide sequence may be the same or different.

Figure 7:
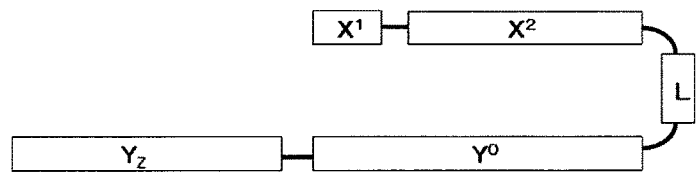
FIG. 7 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-43), in which a nucleotide sequence Y contains an antisense sequence, and a first nucleotide sequence portion and a second nucleotide sequence portion hybridize within a molecule thereof, is shown in FIG. 7. In the single-stranded oligonucleotide shown in FIG. 7, $X^1$ composed of 2 or 3 nucleotides selected from 2'-O-methyl nucleotides and LNA, $X^2$ composed of 8 to 12 deoxyribonucleotides and having the first nucleotide sequence, L composed of 4 to 7 nucleotides independently selected from deoxyribonucleotides and ribonucleotides, $Y^0$ composed of 10 to 15 ribonucleotides and having the second nucleotide sequence, and $Y_Z$ having at least one of a 2'-O-methyl nucleotide and LNA, composed of 10 to 20 nucleotides independently selected from deoxyribonucleotides, 2'-O-methyl nucleotides and LNA, and having an antisense sequence, are bound in this order. The direction of bonding from $X^1$ to $Y_Z$ may be in the 5' to 3' direction or in the 3' to 5' direction. In FIG. 7, $X^2$ having the first nucleotide sequence and $Y^0$ having the second nucleotide sequence form a double strand. Although $X^1$ and $Y^0$ may or may not form a double strand, they preferably form a double strand.

Figure 8:
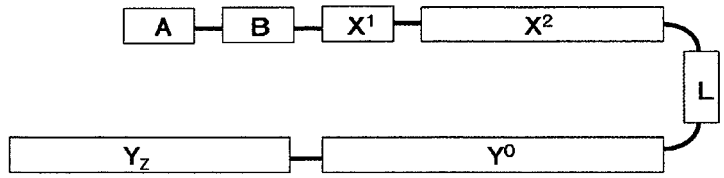
FIG. 8 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-44), in which a nucleotide sequence Y contains an antisense sequence, and a first nucleotide sequence portion and a second nucleotide sequence portion hybridize within a molecule thereof, is shown in FIG. 8. In the single-stranded oligonucleotide shown in FIG. 8, A in the form of a group derived from a functional molecule, B in the form of a C2-20 alkylene group and the like, $X^1$ composed of 2 or 3 nucleotides selected from 2'-O-methyl nucleotides and LNA, $X^2$ composed of 8 to 12 deoxyribonucleotides and having the first nucleotide sequence, L composed of 4 to 7 nucleotides independently selected from deoxyribonucleotides and ribonucleotides, $Y^0$ composed of 10 to 15 ribonucleotides and having the second nucleotide sequence, and $Y_Z$ having at least one of a 2'-O-methyl nucleotide and LNA, composed of 10 to 20 nucleotides independently selected from deoxyribonucleotides, 2'-O-methyl nucleotides and LNA, and having an antisense sequence, are bound in this order. The direction of bonding from $X^1$ to $Y_Z$ may be in the 5' to 3' direction or in the 3' to 5' direction. In FIG. 8, $X^2$ having the first nucleotide sequence and a portion of $Y^0$ having the second nucleotide sequence form a double strand. Although $X^1$ and $Y^0$ may or may not form a double strand, they preferably form a double strand.

Figure 9:
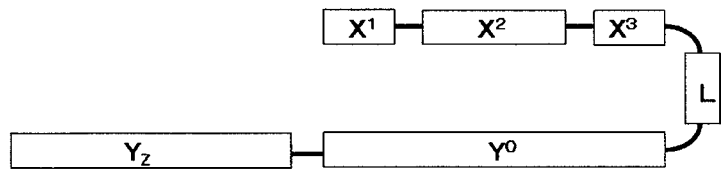
FIG. 9 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-52), in which a nucleotide sequence Y contains an antisense sequence, and a first nucleotide sequence portion and a second nucleotide sequence portion hybridize within a molecule thereof, is shown in FIG. 9. A first nucleotide sequence may contain an antisense sequence. In the single-stranded oligonucleotide shown in FIG. 9, $X^1$ composed of 2 or 3 LNA, $X^2$ composed of 8 to 12 deoxyribonucleotides and having the first nucleotide sequence, $X^3$ composed of 2 or 3 LNA, L composed of 4 to 7 nucleotides independently selected from deoxyribonucleotides and ribonucleotides, $Y^0$ composed of 12 to 16 ribonucleotides and having the second nucleotide sequence, and $Y_Z$ having at least one of a 2'-O-methyl nucleotide and LNA, composed of 10 to 20 nucleotides independently selected from deoxyribonucleotides, 2'-O-methyl nucleotides and LNA, and having an antisense sequence, are bound in this order. The direction of bonding from $X^1$ to $Y_Z$ may be in the 5' to 3' direction or in the 3' to 5' direction. In FIG. 9, $X^2$ having the first nucleotide sequence and $Y^0$ having the second nucleotide sequence form a double strand. Although $X^1$ and $X^3$ may or may not respectively and independently form a double strand with $Y^0$, they preferably form a double strand.

Figure 10:
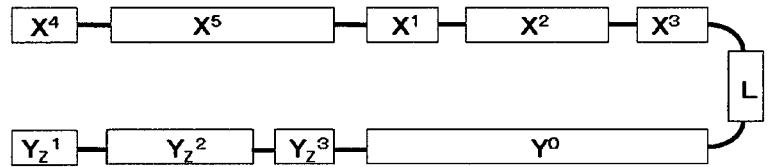
FIG. 10 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof, and an antisense sequence portion $Y_Z^2$ contained by Y and a nucleotide sequence portion $X^5$ contained by X hybridize within a molecule thereof.

A conceptual diagram of the single-stranded oligonucleotide described in C-64), in which a nucleotide sequence Y contains an antisense sequence, and a first nucleotide sequence portion and a second nucleotide sequence portion hybridize within a molecule thereof, is shown in FIG. 10. In the single-stranded oligonucleotide shown in FIG. 10, $X^4$ composed of 2 or 3 2'-O-methyl nucleotides, $X^5$ composed of 10 to 13 ribonucleotides and having a seventh nucleotide sequence, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^0$ composed of 12 to 16 ribonucleotides and having the second nucleotide sequence, $Y_Z^3$ having 2 or 3 LNA, $Y_Z^2$ composed of 8 to 10 deoxyribonucleotides and having an antisense sequence portion contained by Y, and $Y_Z^1$ composed of 2 or 3 LNA, are bound in this order. The direction of bonding from $X^4$ to $Y_Z^1$ may be in the 5' to 3' direction or in the 3' to 5' direction. The first nucleotide sequence may be an antisense sequence. In FIG. 10, $X^2$ having the first nucleotide sequence and $Y^0$ having the second nucleotide sequence form a double strand, and $Y_Z^2$ having the antisense sequence contained by Y and $X^5$ having the seventh nucleotide sequence form a double strand. Although $X^1$ and $X^3$ may or may not respectively and independently form a double strand with $Y^0$, they preferably form a double strand. Although $X^5$ and $Y_Z^3$ may or may not form a double strand, they preferably form a double strand. Although $X^4$ and $Y_Z^1$ may or may not form a double strand, they preferably form a double strand.

Figure 11:
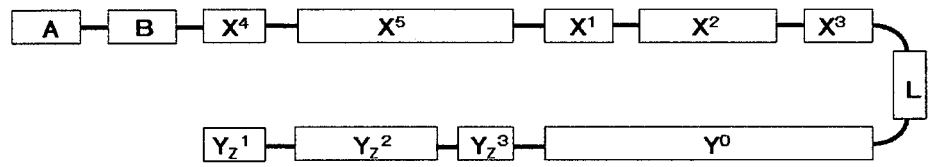
FIG. 11 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof, and an antisense sequence portion $Y_Z^2$ contained by Y and a nucleotide sequence portion $X^5$ contained by X hybridize within a molecule thereof.

A conceptual diagram of the single-stranded oligonucleotide described in C-66), in which a nucleotide sequence Y contains an antisense sequence, and a first nucleotide sequence portion and a second nucleotide sequence portion hybridize within a molecule thereof, is shown in FIG. 11. In the single-stranded oligonucleotide shown in FIG. 11, A in the form of a group derived from a functional molecule, B in the form of a C2-20 alkylene group and the like, $X^4$ composed of 2 or 3 2'-O-methyl nucleotides, $X^5$ composed of 10 to 13 ribonucleotides and having a seventh nucleotide sequence, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, composed of 12 to 16 ribonucleotides and having the second nucleotide sequence, $Y_Z^3$ having 2 or 3 LNA, $Y_Z^2$ composed of 8 to 10 deoxyribonucleotides and having an antisense sequence portion contained by Y, and $Y_Z^1$ composed of 2 or 3 LNA, are bound in this order. The direction of bonding from A to $Y_Z^1$ may be in the 5' to 3' direction or in the 3' to 5' direction. The first nucleotide sequence may be an antisense sequence. In FIG. 11, $X^2$ having the first nucleotide sequence and $Y^0$ having the second nucleotide sequence form a double strand, and $Y_Z^2$ having the antisense sequence contained by Y and $X^5$ having the seventh nucleotide sequence form a double strand. Although $X^1$ and $X^3$ may or may not respectively and independently form a double strand with $Y^0$, they preferably form a double strand. Although $X^5$ and $Y_Z^3$ may or may not form a double strand, they preferably form a double strand. Although $X^4$ and $Y_Z^1$ may or may not form a double strand, they preferably form a double strand.

Figure 12:
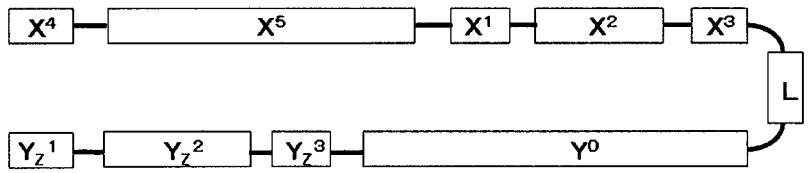
FIG. 12 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof, and an antisense sequence portion $Y_Z^2$ contained by Y and a nucleotide sequence portion $X^5$ contained by X hybridize within a molecule thereof.

A conceptual diagram of the single-stranded oligonucleotide described in C-80), in which a nucleotide sequence Y contains an antisense sequence, and a first nucleotide sequence portion and a second nucleotide sequence portion hybridize within a molecule thereof, is shown in FIG. 12. In the single-stranded oligonucleotide shown in FIG. 12, $X^4$ composed of 2 or 3 2'-O-methyl nucleotides, $X^5$ composed of 11 to 19 ribonucleotides and having a seventh nucleotide sequence, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^0$ composed of 14 to 22 ribonucleotides and having the second nucleotide sequence, $Y_Z^3$ having 2 or 3 LNA, $Y_Z^2$ composed of 8 to 10 deoxyribonucleotides and having an antisense sequence portion contained by Y, and $Y_Z^1$ composed of 2 or 3 LNA, are bound in this order. The direction of bonding from $X^4$ to $Y_Z^1$ may be in the 5' to 3' direction or in the 3' to 5' direction. The first nucleotide sequence may be an antisense sequence. In FIG. 12, $X^2$ having the first nucleotide sequence and $Y^0$ having the second nucleotide sequence form a double strand, $Y_Z^2$ having the antisense sequence contained by Y and $X^5$ having the seventh nucleotide sequence form a double strand, and $Y^0$ and $X^5$ partially form a double strand. Although $X^1$ and $X^3$ may or may not respectively and independently form a double strand with $Y^0$, they preferably form a double strand. Although $X^5$ and $Y_Z^3$ may or may not form a double strand, they preferably form a double strand. Although $X^4$ and $Y_Z^1$ may or may not form a double strand, they preferably form a double strand.

Figure 13:
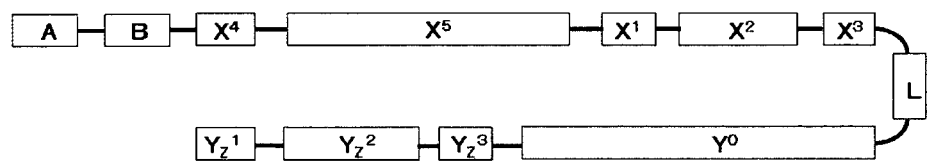
FIG. 13 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof, and an antisense sequence portion $Y_Z^2$ contained by Y and a nucleotide sequence portion $X^5$ contained by X hybridize within a molecule thereof.

A conceptual diagram of the single-stranded oligonucleotide described in C-82), in which a nucleotide sequence Y contains an antisense sequence, and a first nucleotide sequence portion and a second nucleotide sequence portion hybridize within a molecule thereof, is shown in FIG. 13. In the single-stranded oligonucleotide shown in FIG. 13, A in the form of a group derived from a functional molecule, B in the form of a C2-20 alkylene group and the like, $X^4$ composed of 2 or 3 2'-O-methyl nucleotides, $X^5$ composed of 11 to 19 ribonucleotides and having a seventh nucleotide sequence, $X^1$ composed of 2 or 3 LNA, $X^2$ composed of 8 to 10 deoxyribonucleotides and having the first nucleotide sequence, $X^3$ composed of 2 or 3 LNA, L composed of 4 to 7 nucleotides independently selected from deoxyribonucleotides and ribonucleotides, $Y^0$ composed of 14 to 22 ribonucleotides and having the second nucleotide sequence, $Y_Z^3$ having 2 or 3 LNA, $Y_Z^2$ composed of 8 to 10 deoxyribonucleotides and having an antisense sequence portion contained by Y, and $Y_Z^1$ composed of 2 or 3 LNA, are bound in this order. The direction of bonding from A to $Y_Z^1$ may be in the 5' to 3' direction or in the 3' to 5' direction. The first nucleotide sequence may be an antisense sequence. In FIG. 13, $X^2$ having the first nucleotide sequence and a portion of $Y^0$ having the second nucleotide sequence form a double strand, $Y_Z^2$ having the antisense sequence contained by Y and $X^5$ having the seventh nucleotide sequence form a double strand, and $Y^0$ and $X^5$ partially form a double strand. Although $X^1$ and $X^3$ may or may not respectively and independently form a double strand with $Y^0$, they preferably form a double strand. Although $X^5$ and $Y_Z^3$ may or may not form a double strand, they preferably form a double strand. Although $X^4$ and $Y_Z^1$ may or may not form a double strand, they preferably form a double strand.

Figure 14:
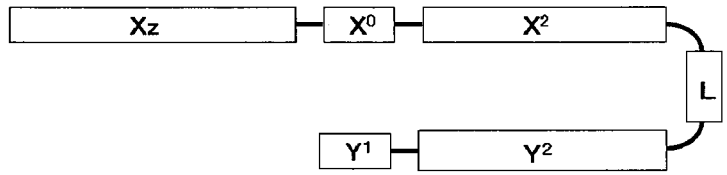
FIG. 14 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in C-98), in which a nucleotide sequence X contains an antisense sequence, and a first nucleotide sequence portion and a second nucleotide sequence portion hybridize within a molecule thereof, is shown in FIG. 14. In the single-stranded oligonucleotide shown in FIG. 14, $X_Z$ having at least one of a 2'-O-methyl nucleotide and LNA, composed of 10 to 20 nucleotides independently selected from deoxyribonucleotides, 2'-O-methyl nucleotides and LNA, and having an antisense sequence, $X^0$ composed of 2 to 5 nucleotides independently selected from deoxyribonucleotides and ribonucleotides, $X^2$ composed of 8 to 17 deoxyribonucleotides and having the first nucleotide sequence, L composed of 4 to 7 nucleotides independently selected from deoxyribonucleotides and ribonucleotides, $Y^2$ composed of 8 to 19 ribonucleotides and having the second nucleotide sequence, and $Y^1$ having 2 or 3 2'-O-methyl nucleotides, are bound in this order. The direction of bonding from $X_Z$ to $Y^1$ may be in the 5' to 3' direction or in the 3' to 5' direction. In FIG. 14, $X^2$ having the first nucleotide sequence and $Y^2$ having the second nucleotide sequence form a double strand. Although $X^0$ and $Y^1$ may or may not form a double strand, they preferably form a double strand.

Figure 15:
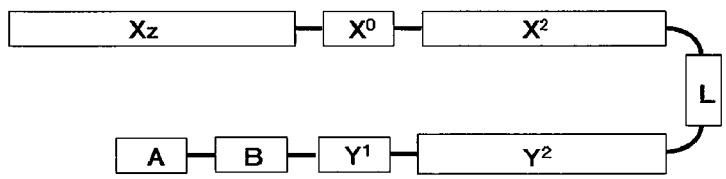
FIG. 15 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in C-99), in which a nucleotide sequence X contains an antisense sequence, and a first nucleotide sequence portion and a second nucleotide sequence portion hybridize within a molecule thereof, is shown in FIG. 15. In the single-stranded oligonucleotide shown in FIG. 15, $X_Z$ having at least one of a 2'-O-methyl nucleotide and LNA, composed of 10 to 20 nucleotides independently selected from deoxyribonucleotides, 2'-O-methyl nucleotides and LNA, and having an antisense sequence, $X^0$ composed of 2 to 5 nucleotides independently selected from deoxyribonucleotides and ribonucleotides, $X^2$ composed of 8 to 17 deoxyribonucleotides and having the first nucleotide sequence, L composed of 4 to 7 nucleotides independently selected from deoxyribonucleotides and ribonucleotides, $Y^2$ composed of 8 to 19 ribonucleotides and having the second nucleotide sequence, $Y^1$ having 2 or 3 2'-O-methyl nucleotides, B in the form of a C2-20 alkylene group and the like, and A in the form of a group derived from a functional molecule, are bound in this order. The direction of bonding from $X_Z$ to A may be in the 5' to 3' direction or in the 3' to 5' direction. In FIG. 15, $X^2$ having the first nucleotide sequence and $Y^2$ having the second nucleotide sequence form a double strand. Although $X^0$ and $Y^1$ may or may not form a double strand, they preferably form a double strand.

The following lists examples of preferable methods for using the single-stranded oligonucleotide of the present invention.

E-1) A method for controlling the function of a target RNA, comprising a step for contacting the single-stranded nucleotide described in any of 1) to 167) and C-1) to C-132) with a cell.

E-2) A method for controlling the function of a target RNA in a mammal, comprising a step for administering a pharmaceutical composition containing the single-stranded oligonucleotide described in any of 1) to 167) and C-1) to C-132) to the mammal.

E-3) The method described in E-2), wherein the mammal is a human.

E-4) The method described in E-2) or E-3), wherein the administration route is enteral.

E-5) The method described in E-2) or E-3), wherein the administration route is parenteral.

E-6) A use of the single-stranded oligonucleotide described in any of 1) to 167) and C-1) to C-132) for controlling the function of a target RNA in a mammal.

E-7) A use of the single-stranded oligonucleotide described in any of 1) to 167) and C-1) to C-132) for producing a drug for controlling a target RNA in a mammal.

E-8) The use described in E-6) or E-7), wherein the mammal is a human.

E-9) A method for controlling the function of a target RNA, comprising a step for contacting the single-stranded oligonucleotide described in any of B-1) to B-82) with a cell.

E-10) A method for decreasing expression of the function of a target RNA in a mammal, comprising a step for administering a pharmaceutical composition containing the single-stranded oligonucleotide described in any of B-1) to B-82) to the mammal.

E-11) The method described in E-10), wherein the mammal is a human.

E-12) The method described in E-10) or E-11), wherein the administration route is enteral.

E-13) The method described in E-10) or E-11), wherein the administration route is parenteral.

E-14) A use of the single-stranded oligonucleotide described in any of B-1) to B-82) for controlling the function of a target RNA in a mammal.

E-15) A use of the single-stranded oligonucleotide described in any of B-1) to B-82) for producing a drug for controlling the function of a target RNA in a mammal.

E-16) The use described in E-14) or E-15), wherein the mammal is a human.

Control of the function of a target RNA in the present invention refers to suppressing translation or regulating or converting a splicing function such as exon splicing that occurs by covering a portion of a target RNA due to hybridization by an antisense sequence portion, or degrading the target RNA that is able to occur as a result of recognition of a hybridized portion of an antisense sequence portion and the target RNA.

E-17) A method for controlling the expression of a target gene, comprising a step for contacting the single-stranded oligonucleotide described in any of 1) to 167) and C-1) to C-132) with a cell.

E-18) A method for controlling the expression of a target gene in a mammal, comprising a step for administering a pharmaceutical composition containing the single-stranded oligonucleotide described in any of 1) to 167) and C-1) to C-132) to the mammal.

E-19) The method described in E-18), wherein the mammal is a human.

E-20) The method described in E-18) or E-19), wherein the administration route is enteral.

E-21) The method described in E-18) or E-19), wherein the administration route is parenteral.

E-22) A use of the single-stranded oligonucleotide described in any of 1) to 167) and C-1) to C-117) for controlling the expression of a target gene in a mammal.

E-23) A use of the single-stranded oligonucleotide described in any of 1) to 167) and C-1) to C-132) for producing a drug for controlling the expression of a target gene in a mammal.

E-24) The use described in E-23) or E-24), wherein the mammal is a human.

E-25) A method for controlling the expression of a target gene, comprising a step for contacting the single-stranded oligonucleotide described in any of B-1) to B-82) with a cell.

E-26) A method for controlling the expression of a target gene in a mammal, comprising a step for administering a pharmaceutical composition containing the single-stranded oligonucleotide described in any of B-1) to B-82) to the mammal.

E-27) The method described in E-26), wherein the mammal is a human.

E-28) The method described in E-26) or E-27), wherein the administration route is enteral.

E-29) The method described in E-26) or E-27), wherein the administration route is parenteral.

E-30) A use of the single-stranded oligonucleotide described in any of B-1) to B-82) for controlling the expression of a target gene in a mammal.

E-31) A use of the single-stranded oligonucleotide described in any of B-1) to B-82) for producing a drug for controlling the expression of a target gene in a mammal.

E-32) The use described in E-30) or E-31), wherein the mammal is a human.

Although the above has provided an explanation of preferable aspects of single-stranded oligonucleotides, the single-stranded oligonucleotide of the present invention is not limited to the aforementioned aspects. The single-stranded oligonucleotide includes, for example that included therein which is present after having undergone tautomerism or geometrical isomerism regardless of whether endocyclical or exocyclical, as well as that present as mixtures thereof or as mixtures of respective isomers thereof. In addition, in the case of the presence of an asymmetric center or in the case of generating an asymmetric center as a result of isomerization, the single-stranded oligonucleotide includes that which is present as respective isomers thereof and mixtures of arbitrary ratios in the case an asymmetric center occurs. In addition, in the case of a compound having two or more asymmetric centers, diastereomers are also present due to their respective optical isomers. The present invention includes all of these forms in any ratio thereof.

The present invention also includes a pharmaceutically acceptable salt of the single-stranded nucleotide represented by formula (I).

The single-stranded oligonucleotide represented by formula (I) can also be converted to a pharmaceutically acceptable salt or released from a formed salt as necessary. Examples of pharmaceutically acceptable salts of the single-stranded oligonucleotide represented by formula (I) include salts formed with alkaline metals (such as lithium, sodium or potassium), alkaline earth metals (such as magnesium or calcium), ammonium, organic bases (such as triethylamine or trimethylamine), amino acids (such as glycine, lysine or glutamic acid), inorganic acids (such as hydrochloric acid, hydrobromic acid, phosphoric acid or sulfuric acid), and organic acids (such as acetic acid, citric acid, maleic acid, fumaric acid, tartaric acid, benzenesulfonic acid, methanesulfonic acid or p-toluenesulfonic acid).

In particular, a partial structure represented by —P(=O)(OH)— may be converted to an anionic partial structure represented by —P(=O)(O$^-$)— to form a salt with an alkaline metal (such as lithium, sodium or potassium), alkaline earth metal (such as magnesium or calcium) or ammonium. In addition, a partial structure represented by —P(=O)(SH)—, which forms a phosphorothioate bond, may be converted to an anionic partial structure represented by —P(=O)(S$^-$)— to similarly form a salt with an alkaline metal, alkaline earth metal or ammonium.

The present invention also includes a prodrug of the single-stranded oligonucleotide represented by formula (I).

A prodrug refers to derivative of a pharmaceutical compound having a group that can be chemically or metabolically degraded, and is a compound that is degraded by solvolysis or in vivo under physiological conditions and derived to a pharmacologically active pharmaceutical compound. Suitable methods for selecting and producing prodrug derivatives are described in, for example, Design of Prodrugs, (Elsevier, Amsterdam, 1985). In the case of the present invention, and in the case of having a hydroxyl group, an example of a prodrug is an acyloxy derivative produced by reacting the compound with a suitable acyl halide, suitable acid anhydride or suitable halogenated alkyloxycarbonyl compound. Particularly preferable examples of the structures of the prodrug include —O—COC$_2$H$_5$, —O—CO-(t-Bu), —O—COC$_{15}$H$_{31}$, —O—CO(m-CO$_2$Na-Ph), —O—COCH$_2$CH$_2$CO$_2$Na—OCOCH(NH$_2$)CH$_3$, —O—COCH$_2$N(CH$_3$)$_2$ and —O—CH$_2$OC(=O)CH$_3$. In the case the single-stranded oligonucleotide that forms the present invention has an amino group, examples of the prodrug include those produced by reacting the compound having an amino group with a suitable acid halide, suitable mixed acid anhydride or suitable halogenated alkyloxycarbonyl compound. Particularly preferable examples of the structure of the prodrug include —NH—CO(CH$_2$)$_{20}$OCH$_3$, —NH—COCH(NH$_2$)CH$_3$ and —NH—CH$_2$OC(=O)CH$_3$.

Although the single-stranded oligonucleotide indicated in formula (I) of the present invention, or a pharmaceutically allowable salt thereof, can be present in an arbitrary crystalline form or arbitrary hydrate according to the production conditions, these crystalline forms, hydrates and mixtures thereof are included within the scope of the present invention. In addition, although the single-stranded oligonucleotide indicated in formula (I) of the present invention, or a pharmaceutically allowable salt thereof, can also be present as a solvate of acetone, ethanol, 1-propanol or 2-propanol and the like, all of these forms are also included within the scope of the present invention.

The single-stranded oligonucleotide can be produced by suitably selecting a method known among persons with ordinary skill in the art. For example, a person with ordinary skill in the art is able to synthesize the single-stranded oligonucleotide by designing the nucleotide sequence of the single-stranded oligonucleotide based on nucleotide sequence data of a target RNA and then synthesizing the single-stranded oligonucleotide using a commercially available automated nucleic acid synthesizer (such as that manufactured by Applied Biosystems, Beckman or GeneDesign). In addition, the single-stranded oligonucleotide can also be synthesized by a reaction using enzymes. Examples of the aforementioned enzymes include, but are not limited to, polymerases, ligases and restriction enzymes. Namely, a method for producing the single-stranded oligonucleotide according to the present embodiment can comprise a step for extending a nucleotide strand at the 3'-end or 5'-end of an oligonucleotide containing at least one of X, L and Y.

Numerous methods are known in the art for bonding functional molecules with the oligonucleotide, and examples thereof can be referred to in, for example, the European Journal of Pharmaceuticals and Biopharmaceutics, Vol. 107, pp. 321-340 (2016), Advanced Drug Delivery Reviews, Vol. 104, pp. 78-92 (2016), or Expert Opinion of Drug Delivery, Vol. 11, pp. 791-822 (2014). For example, after bonding a functional molecule and a linker according to a known method, the resulting linker and functional molecule are derived to an amidite with an amidition reagent or derived to an H-phosphonate form with an H-phosphonate reagent followed by bonding to the oligonucleotide.

A single-stranded oligonucleotide can be prepared by purifying the resulting oligonucleotide by reversed phase column chromatography and the like. A single-stranded oligonucleotide that has hybridized within a molecule thereof can be prepared by mixing the prepared single-stranded oligonucleotide in a suitable buffer solution and denaturing for several minutes (such as 5 minutes) at 90° C. to 98° C. followed by hybridizing over the course of 1 to 8 hours at 30° C. to 70° C. There are cases in which the intramolecular hybridization step can be omitted.

The single-stranded oligonucleotide is able to effectively control expression of a target gene. Thus, the present invention is able to provide a composition containing the single-stranded oligonucleotide as an active ingredient thereof for, for example, controlling expression of a target gene based on an antisense effect. In particular, since the single-stranded oligonucleotide allows the obtaining of high pharmacological efficacy by administering at a low concentration, pharmaceutical compositions for the treatment, prevention and improvement of diseases such as metabolic diseases, tumors or infections associated with overexpression of a target gene can also be provided in several embodiments.

A composition containing the single-stranded oligonucleotide can be formulated according to a known pharmaceutical preparation method. For example, a composition containing the single-stranded oligonucleotide can be used either enterally (such as orally) or parenterally as a capsule, tablet, pill, liquid, powder, granule, fine granule, film-coated preparation, pellet, troche, sublingual preparation, chewed preparation, buccal preparation, paste, syrup, suspension, elixir, emulsion, coated preparation, ointment, plaster, poultice, transcutaneously absorbed preparation, lotion, inhalant, aerosol, injection preparation or suppository.

These preparations can be suitably combined with a pharmaceutically acceptable carrier or a carrier in the form of a food or beverage, specific examples of which include sterile water or physiological saline, vegetable oil, solvent, base, emulsifier, suspending agent, surfactant, pH adjuster, stabilizer, flavoring agent, fragrance, excipient, vehicle, preservative, binder, diluent, isotonic agent, analgesic, filler, disintegration agent, buffer, coating agent, lubricant, colorant, sweetener, thickening agents, corrective, solubilizing aid and other additives.

There are no particular limitations on the administration form of the composition containing the single-stranded oligonucleotide, and examples thereof include enteral (oral) and parenteral administration. More preferably, examples of administration forms include intravenous administration, intraarterial administration, intraperitoneal administration, subcutaneous administration, intradermal administration, intratracheal administration, rectal administration, intramuscular administration, intrathecal administration, intraventricular administration, transnasal administration and intravitreal administration.

There are no particular limitations on the disease able to be treated, prevented or improved by using the single-stranded oligonucleotide, and examples thereof include metabolic diseases, circulatory diseases, tumors, infections, ophthalmic diseases, inflammatory diseases, autoimmune diseases, hereditary rare diseases, and diseases caused by expression of a gene. Specific examples include hypercholesterolemia, hypertriglyceridemia, spinal muscular atrophy, muscular dystrophy (such as Duchenne muscular dystrophy, myotonic dystrophy, congenital muscular dystrophy (such as Fukuyama-type congenital muscular dystrophy, Ullrich-type congenital muscular dystrophy, merosin-deficient congenital muscular dystrophy, integrin deficiency or Walker Warburg syndrome), Becker muscular dystrophy, limb-girdle muscular dystrophy, Miyoshi muscular dystrophy or facioscapulohumeral muscular dystrophy), Huntington's disease, Alzheimer's disease, transthyretin amyloidosis, familial amyloid cardiomyopathy, multiple sclerosis, Crohn's disease, inflammatory bowel disease, acromegaly, type 2 diabetes, chronic renal disease, RS virus infection, Ebola hemorrhagic fever, Marburg virus, HIV, influenza, hepatitis B, hepatitis C, cirrhosis, chronic cardiac insufficiency, myocardial fibrosis, atrial fibrillation, prostate cancer, melanoma, breast cancer, pancreatic cancer, colon cancer, renal cell carcinoma, cholangiocarcinoma, cervical cancer, liver cancer, lung cancer, leukemia, non-Hodgkin's lymphoma, atopic dermatitis, glaucoma and age-related macular degeneration. The gene causing the aforementioned disease can be set for the aforementioned target gene corresponding to the type of disease, and the aforementioned expression control sequence (such as an antisense sequence) can be suitably set corresponding to the sequence of the aforementioned target gene.

Diseases of mammals such as humans as well as various other mammals can be treated, prevented or improved with a composition containing the single-stranded oligonucleotide. Although not limited thereto, various diseases of species of mammals, including cows, sheep, goats, horses, dogs, cats, guinea pigs and other bovines, ovines, equines, canines, felines and species of rodents such as mice can be treated. In addition, a composition containing the single-stranded oligonucleotide can also be applied to other species such as birds (such as chickens).

In the case of administering or feeding to animals including humans, although the dosage or ingested amount of a composition containing the single-stranded oligonucleotide can be suitably selected corresponding to the age, body weight, symptoms or health status of the subject or the type of composition (such as a pharmaceutical, food or beverage), the dosage or ingested amount thereof is preferably 0.0001 mg/kg/day to 100 mg/kg/day as the amount of the single-stranded oligonucleotide.

The single-stranded oligonucleotide is able to control expression of a target gene extremely effectively. Thus, a method for controlling expression of a target gene by an antisense effect can be provided by administering the single-stranded oligonucleotide to animals, including humans. In addition, a method can be provided for treating, preventing or improving various types of diseases associated with overexpression of a target gene that comprises administering a composition containing the single-stranded oligonucleotide to animals, including humans.

EXAMPLES

Although the following provides a more detailed explanation of the present invention based on examples and comparative examples, embodiments of the present invention are not limited to the following examples.

Examples 1 to 4 and Comparative Examples 1 to 5

The oligonucleotides shown in Table 1 were prepared using the nS-8II Automated Nucleic Acid Synthesizer (GeneDesign). The target gene was mouse Phosphatase and Tensin Homolog Deleted from Chromosome 10 (PTEN).

Furthermore, in the sequence notations shown in Table 1, "(L)" refers to LNA, "(M)" refers to 2'-O-methyl nucleotide, lower case letters refer to deoxyribonucleotides, upper case letters (excluding those having the aforementioned (L) and (M)) refers to ribonucleotides, "^" refers to a phosphorothioate bond, "5" indicates that the base of that nucleotide is 5-methylcytosine, and "C8Toc-" indicates that a moiety obtained by removing a hydrogen atom from the hydroxyl group of the tocopherol represented by the following formula (IV) is coupled to a single oxygen atom of the phosphate group on the 5'-end through a 1,8-octylene group. In addition, hydroxyl groups are present on the 3'-end and 5'-end of the oligonucleotides shown in Table 1.

(IV)

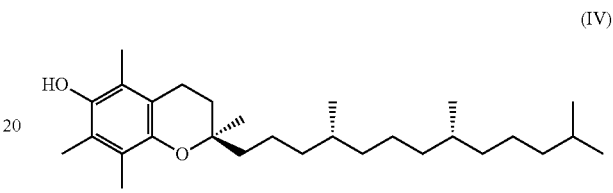

TABLE 1

| | Sequence (left side: 5'-end, right side: 3'-end) | Remarks |
|---|---|---|
| Example 1 (SEQ ID NO: 1) | 5(L)^T(L)^t^a^g^c^a^c^t^g^g^c^5 (L)^T(L)AAAAAGGCCAGUGCUA^A (M)^G(M) | Bases 1-14: X<br>Bases 15-18: L<br>Bases 19-32: Y |
| Example 2 (SEQ ID NO: 2) | A(M)^G(M)^GCCAGUGCUAAGAAAA5 (L)^T(L)^t^a^g^c^a^c^t^g^g^c^5(L)^T (L) | Bases 1-14: X<br>Bases 15-18: L<br>Bases 19-32: Y |
| Example 3 (SEQ ID NO: 3) | A(M)^G(M)^G(M)^CCAGUGCUAAAAAAT (L)^T(L)^a^g^c^a^c^t^g^g^5(L)^5(L) ^T (L) | Bases 1-13: X<br>Bases 14-17: L<br>Bases 18-30: Y |
| Example 4 | C8Toc-A(M)^G(M)GCCAGUGCUAAGAAA A5(L)^T(L)^t^a^g^c^a^c^t^g^g^c^5(L) ^T (L) | Functional molecule bound to sequence of Example 2 |
| Comparative Example 1 (SEQ ID NO: 4, 5) | 5(L)^T(L)^t^a^g^c^a^c^t^g^g^c^5(L) ^T (L)<br>A(M)^G(M)^GCCAGUGCUA^A(M)^G(M) | |
| Comparative Example 2 (SEQ ID NO: 6, 7) | T(L)^T(L)^a^g^c^a^c^t^g^g^5(L)^5 (L)^T(L)<br>A(M)^G(M)^G(M)^CCAGUGCU^A (M)^A(M) | |
| Comparative Example 3 | 5(L)^T(L)^t^a^g^c^a^c^t^g^g^c^5(L) ^T (L)<br>C8Toc-A(M)^G(M)^GCCAGUGCUA^A (M)^G(M) | Functional molecule bound to sequence of Comp. Ex. 1 |
| Comparative Example 4 (SEQ ID NO: 8) | 5(L)^T(L)^t^a^g^c^a^c^t^g^g^c^5(L) ^T (L) | |
| Comparative Example 5 (SEQ ID NO: 9) | T(L)^T(L)^a^g^c^a^c^t^g^g^5(L)^5 (L)^T(L) | |

Intramolecular hybridization in Examples 1 to 4 and intermolecular hybridization between two oligonucleotides in Comparative Examples 1 to 3 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 1

Figure 16:
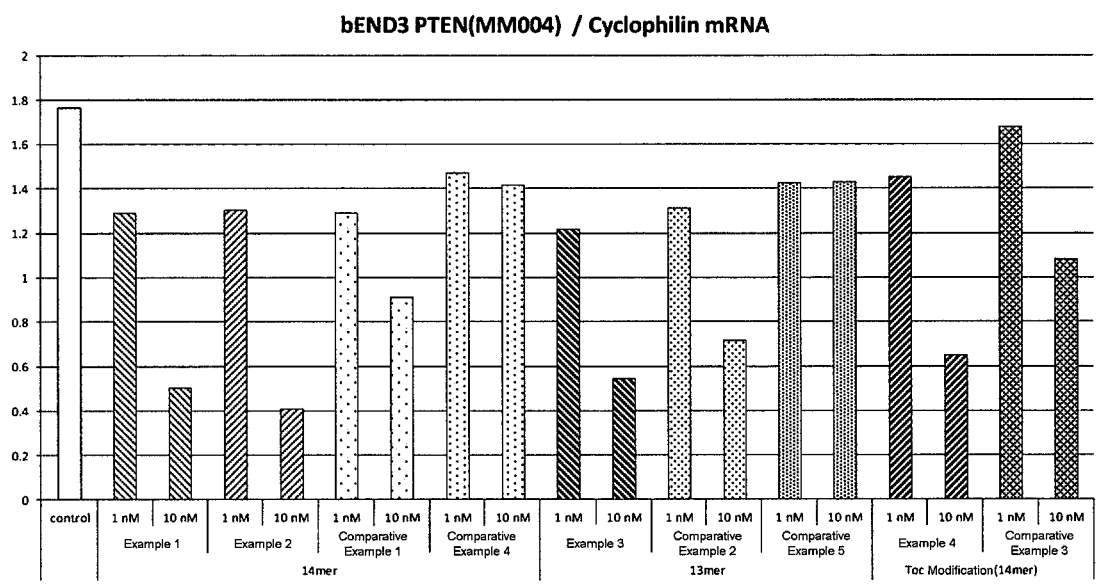
FIG. 16 is a graph indicating the effects of single-stranded oligonucleotides according to the present embodiment on the expression level of PTEN in mouse cerebral endothelial cells.

Mouse brain endothelial cell line bEND cells were disseminated in a 96-well plate at 2000 cells/well followed by culturing for 24 hours at 37° C. in 5% $CO_2$. Each of the oligonucleotides shown in Table 1 was added to each well to a concentration of 1 nM or 10 nM using Lipofectamine® RNAiMax (Thermo Fisher Scientific) (transfection). The medium was replaced after 4 hours and the cells were recovered after 20 hours followed by extracting total RNA from the cells using the RNeasy Mini Kit (Qiagen).

cDNA was obtained from the total RNA using PrimeScript RT Master Mix (Takara Bio). Real-time PCR was then carried out with the 7500 Real-Time PCR System (Applied Biosystems) using the resulting cDNA and TaqMan® Gene Expression ID (Applied Biosystems) to determine the amount of PTEN mRNA. During real-time PCR, the amount of mRNA of a housekeeping gene in the form of cyclophilin was simultaneously assayed, and the amount of PTEN mRNA relative to the amount of cyclophilin mRNA was evaluated as the expression level of PTEN. Cells that did not undergo the transfection procedure were used as a control. The results are shown in FIG. 16.

Furthermore, primers used are in the TaqMan Gene Expression Assays (Applied Biosystems) and the Assay ID were as indicated below.
  Mouse PTEN assay: Mm00477208_m1
  Mouse cyclophilin assay: Mm0234230_g1
As is clear from FIG. 16, single-stranded oligonucleotides according to the present invention (Examples 1 to 4) were confirmed to demonstrate a high antisense effect in comparison with HDO (Comparative Examples 1 to 3) and ASO (Comparative Examples 4 and 5).

Examples 5 and 6 and Comparative Examples 4, 6 and 7

The oligonucleotides shown in Table 2 were prepared using the nS-8II Automated Nucleic Acid Synthesizer (GeneDesign). The target genes consisted of human Phosphatase and Tensin Homolog Deleted from Chromosome 10 (PTEN) and human apolipoprotein B (ApoB). Furthermore, the sequence notations in Table 2 are the same as those of Table 1.

TABLE 2

| | Sequence (left side: 5'-end, right side: 3'-end) | Remarks |
|---|---|---|
| Example 5 (SEQ ID NO: 10) | G(L)^5(L)^a^t^t^g^g^t^a^t^T (L)^5(L)^A(L)AAAAUGAAUACC AAUGC5(L)^T (L)^t^a^g^c^a^c^t^g^g^c^5 (L)^T(L) | Bases 1-13: X ApoB target Bases 14-17: L Bases 15-44: Y Bases 31-44: PTEN target |
| Example 6 (SEQ ID NO: 11) | 5(L)^T(L)^t^a^g^c^a^c^t^g^g^c^5 (L)^T(L)UGAAUACCAAUGCAAAA G(L)^5(L)^a^t^t^g^g^t^a^t^T (L)^5(L)^A(L) | Bases 1-14: PTEN target Bases 1-27: Y Bases 28-31: L Bases 32-44: X ApoB target |
| Comparative Example 6 (SEQ ID NO: 12, 13) | U(M)^G(M)^A(M)^AUACCAAUGC5 (L)^T(L)^t^a^g^c^a^c^t^g^g^c^5 (L)^T(L)G(L) 5 (L)^a^t^t^g^g^t^a^t^T(L)^A(L) | |
| Comparative Example 4 (SEQ ID NO: 8) | 5(L)^T(L)^t^a^g^c^a^c^t^g^g^c^5 (L)^T(L) | PTEN target |
| Comparative Example 7 (SEQ ID NO: 14) | G(L)^5(L)^a^t^t^g^g^t^a^t^T (L)^5(L)^A(L) | ApoB target |

Intramolecular hybridization in Examples 5 to 6 and intermolecular hybridization between two oligonucleotides in Comparative Example 6 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 2

Human hepatoma cell line HuH-7 cells were disseminated in a 96-well plate at 3000 cells/well followed by culturing for 24 hours at 37° C. in 5% $CO_2$. Each of the oligonucleotides shown in Table 2 was added to each well so that their final concentration reached the set concentration using Lipofectamine® RNAiMax (Thermo Fisher Scientific) (transfection). The medium was replaced after 4 hours and the cells were recovered after 20 hours followed by extracting total RNA from the cells using the RNeasy Mini Kit (Qiagen).

cDNA was obtained from the total RNA using PrimeScript RT Master Mix (Takara Bio). Real-time PCR was then carried out with the 7500 Real-Time PCR System (Applied Biosystems) using the resulting cDNA and TaqMan® Gene Expression ID (Applied Biosystems) to determine the amount of PTEN and ApoB mRNA. During real-time PCR, the amount of mRNA of a housekeeping gene in the form of glyceraldehyde-3-phosphate dehydrogenase (GAPDH) was simultaneously assayed, and the amount of PTEN and ApoB mRNA relative to the amount of GAPDH mRNA was evaluated as the expression level of PTEN and ApoB, respectively. Cells that did not undergo the transfection procedure were used as a control. The results are shown in FIGS. 17 and 18.

Furthermore, primers used are in the TaqMan Gene Expression Assays (Applied Biosystems) and the Assay ID were as indicated below.

Human PTEN assay: Hs02621230
Human ApoB assay: Hs00181142
Human GAPDH assay: Hs99999905_m1

Figure 17:
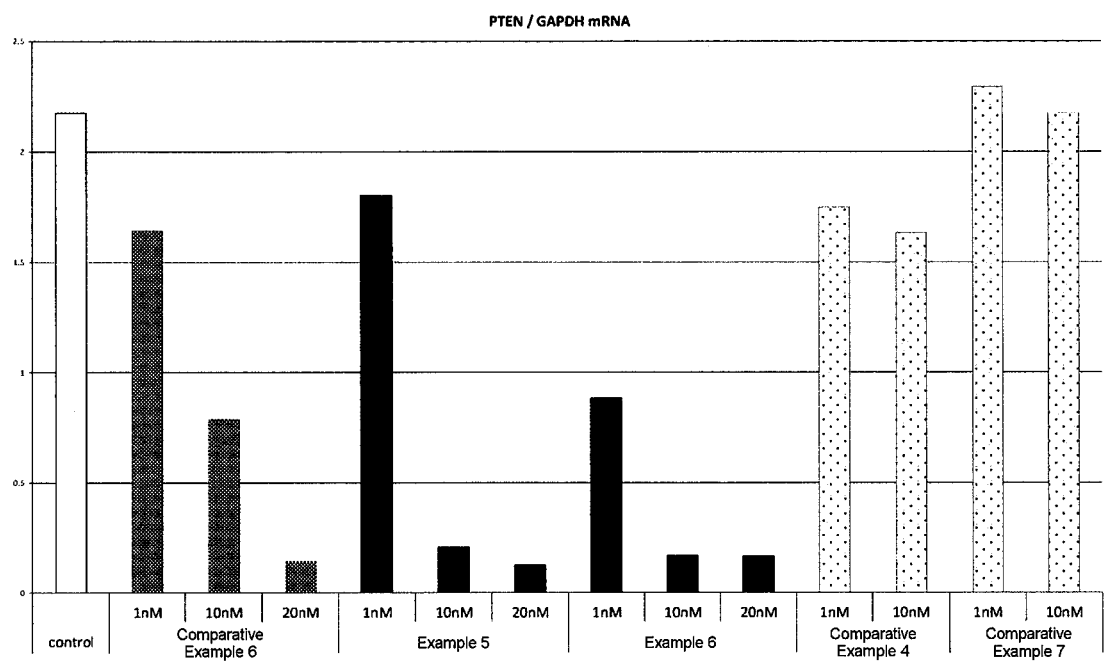
FIG. 17 is a graph indicating the effects of single-stranded oligonucleotides according to the present embodiment on the expression level of PTEN in human hepatoma-derived cells.
Figure 18:
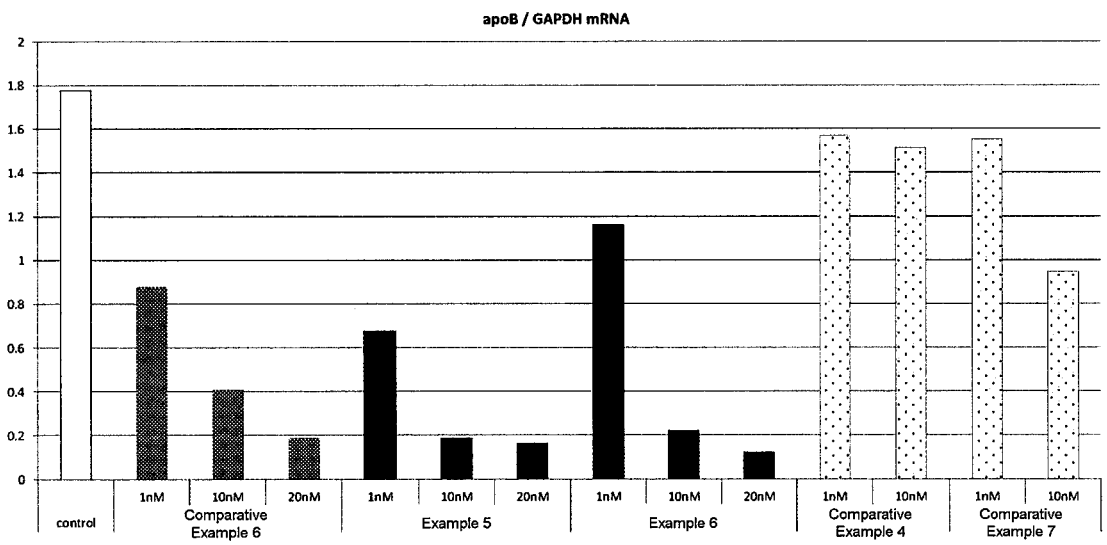
FIG. 18 is a graph indicating the effects of single-stranded oligonucleotides according to the present embodiment on the expression level of ApoB in human hepatoma-derived cells.

As is clear from FIGS. 17 and 18, single-stranded oligonucleotides according to the present invention (Examples 5 and 6) were confirmed to demonstrate a high antisense effect in comparison with HDO (Comparative Example 6) and ASO (Comparative Examples 4 and 7).

Examples 2 and 7 and Comparative Examples 1 and 4

The oligonucleotides shown in Table 3 were prepared using the nS-8II Automated Nucleic Acid Synthesizer (GeneDesign). The target gene consisted of mouse Phosphatase and Tensin Homolog Deleted from Chromosome 10 (PTEN). Furthermore, the sequence notations in Table 3 are the same as those of Table 1.

Intramolecular hybridization in Examples 2 and 7 and intermolecular hybridization between two oligonucleotides in Comparative Example 1 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 3

The final concentrations of each of the oligonucleotides of Table 3 were adjusted to the set concentration and the amount of PTEN mRNA relative to the amount of cyclophilin mRNA was evaluated as the expression level of PTEN using the same evaluation method as Evaluation Example 1. The results are shown in FIG. 19.

Figure 19:
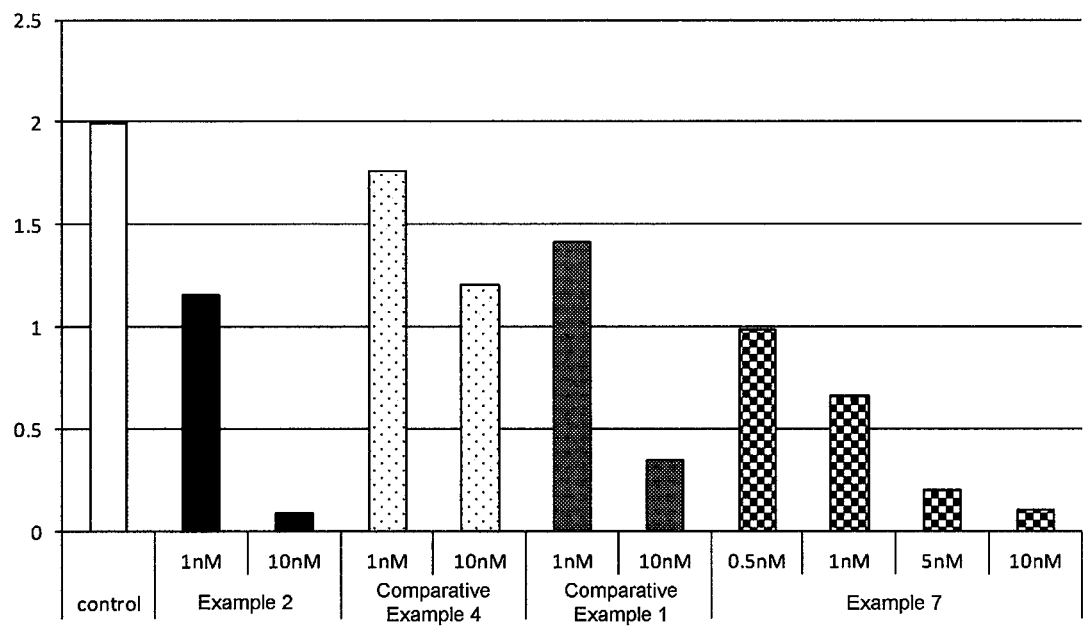
FIG. 19 is a graph indicating the effects of single-stranded oligonucleotides according to the present embodiment on the expression level of PTEN in mouse cerebral endothelial cells.

As is clear from FIG. 19, the single-stranded oligonucleotide according to the present invention (Example 7) was confirmed to demonstrate a high antisense effect in comparison with HDO (Comparative Example 1) and ASO (Comparative Example 4).

Examples 5, 6, 8 and 9 and Comparative Example 6

The oligonucleotides shown in Table 4 were prepared using the nS-8II Automated Nucleic Acid Synthesizer (GeneDesign). The target genes consisted of human Phosphatase and Tensin Homolog Deleted from Chromosome 10 (PTEN) and human apolipoprotein B (ApoB). Furthermore, the sequence notations in Table 4 are the same as those of Table 1.

TABLE 3

|  | Sequence (left side: 5'-end, right side: 3'-end) | Remarks |
| --- | --- | --- |
| Example 2 (SEQ ID NO: 2) | A(M)^G(M)^GCCAGUGCUA AGAAAA5(L)^T(L)^t C^a^g^a^c^t^g^g^c^5(L)^T(L) | Bases 1-14: Y Bases 15-18: L Bases 19-32: X |
| Example 7 (SEQ ID NO: 15) | A(M)^G(M)^GCCAGUGCUAAGU UUUAGGCCAGUGCUAAGAAAA5 (L)^T(L)^t^a^g^c^a^c^t^g^g^c^5 (L)^T(L)AAAA5(L)^T (L)^t^a^g^c^a^c^t^g^g^c^5(L)^T (L) | Bases 1-32: Y Bases 33-36: L Bases 37-50: X Bases 51-54: L' Bases 55-68: X' |
| Comparative Example 1 (SEQ ID NO: 4, 5) | 5(L)^T(L)^t^a^g^c^a^c^t^g^g^c^5 (L)^T(L)A(M)^G(M)^GCCAGUG CUA^A(M)^G(M) |  |
| Comparative Example 4 (SEQ ID NO: 8) | 5(L)^T(L)^t^a^g^c^a^c^t^g^g^c^5 (L)^T(L) |  |

TABLE 4

| | Sequence (left side: 5'-end, right side: 3'-end) | Remarks |
|---|---|---|
| Example 5 (SEQ ID NO: 10) | G(L)^5(L)^a^t^t^g^g^a^t^T (L)^(L)^A(L)AAAAUGAAU ACCAAUGC5(L)^T(L)^t^a^g ^c^a^c^a^c^t^g^g^c^5(L)^T(L) | Bases 1-13: X ApoB target Bases 14-17: L Bases 18-44: Y Bases 31-44: PTEN target |
| Example 6 (SEQ ID NO: 11) | 5(L)^T(L)^t^a^g^c^a^c^t^g^g^c^5 (L)^(L)UGAAUACCAAUGCAAA AG(L)^5(L)^a^t^t^g^g^t^a^t^T (L)^(L)^A(L) | Bases 1-14: PTEN target Bases 1-27: Y Bases 28-31: L Bases 32-44: X ApoB target |
| Example 8 (SEQ ID NO: 16) | U(M)^G(M)^A(M)^AUACCAAUGCA AAA5(L)^T(L)^t^a^g^c^a^c^t^g^g^c^5 (L)^T(L)AAAAAGGCCAGUGCUAAGU UUUG(L)^5(L)^a^t^t^g^g^t^a^t^T (L)^(L)^A(L) | Bases 1-31: X Bases 18-31: PTEN target Bases 32-35: L Bases 36-66: Y Bases 54-66: ApoB target |
| Example 9 (SEQ ID NO: 17) | U(M)^G(M)^A(M)^AUACCAAUGCUUU UAGGCCAGUGCUAAGAAAA5(L)^T (L)^t^a^g^c^a^c^t^g^g^c^5(L)^T(L) AAAAG(L)^5(L)^a^t^t^g^g^t^a^t^T (L)^5(L)^A(L) | Bases 1-31:Y Bases 32-35: L Bases 36-49: X PTEN target Bases 50-53: L' Bases 54-66: X' ApoB target |
| Comparative Example (SEQ ID NO: 12, 13) | U(M)^G(M)^A(M)^AUACCAAUGC5 (L)^5(L)^t^a^g^c^a^c^t^g^g^c^5(L)^5 (L)G(L)^5(L)^a^t^t^g^g^t^a^t^T (L)^5(L)^A(L) | |

Intramolecular hybridization in Examples 5, 6, 8 and 9 and intermolecular hybridization between two oligonucleotides in Comparative Example 6 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 4

The final concentrations of each of the oligonucleotides of Table 4 were adjusted to 1 nM or 10 nM and the amount of PTEN and ApoB mRNA relative to the amount of GAPDH mRNA was evaluated as the expression level of PTEN and ApoB, respectively, using the same evaluation method as Evaluation Example 2. Cells that did not undergo the transfection procedure were used as a control. The results are shown in FIGS. 20 and 21.

Figure 20:
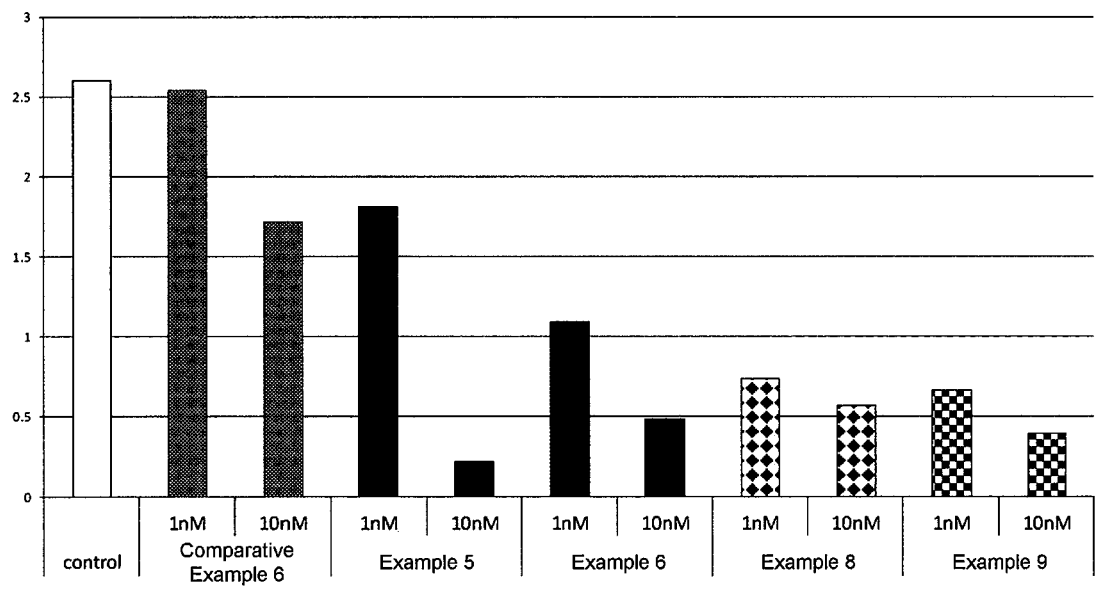
FIG. 20 is a graph indicating the effects of single-stranded oligonucleotides according to the present embodiment on the expression level of PTEN in human hepatoma-derived cells.
Figure 21:
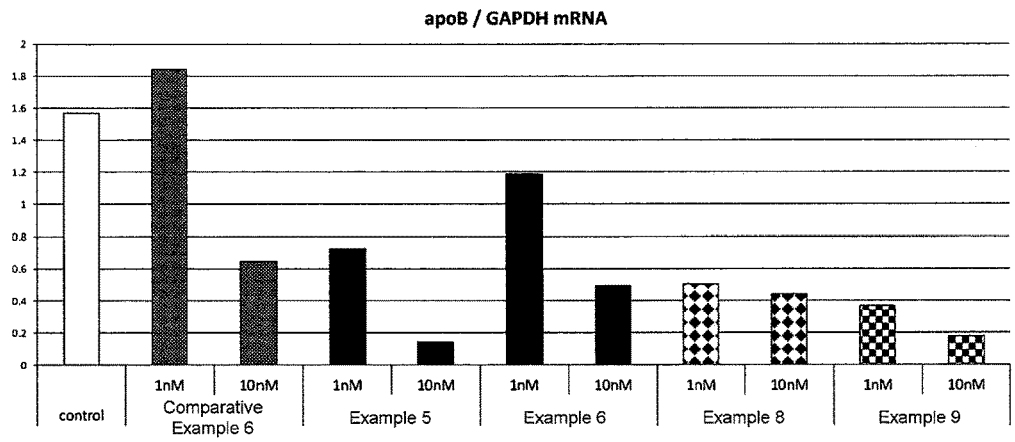
FIG. 21 is a graph indicating the effects of single-stranded oligonucleotides according to the present embodiment on the expression level of ApoB in human hepatoma-derived cells.

As is clear from FIGS. 20 and 21, the single-stranded oligonucleotides according to the present invention (Examples 5, 6, 8 and 9) were confirmed to demonstrate a high antisense effect in comparison with HDO (Comparative Example 6).

Examples 10 and 11 and Comparative Examples 4, 8 and 9

The oligonucleotides shown in Table 5 were prepared using the nS-8II Automated Nucleic Acid Synthesizer (GeneDesign). The target gene was mouse Phosphatase and Tensin Homolog Deleted from Chromosome 10 (PTEN). Furthermore, the sequence notations in Table 5 are the same as those of Table 1.

TABLE 5

| | Sequence (left side: 5'-end, right side: 3'-end) | Remarks |
|---|---|---|
| Example 10 (SEQ ID NO: 18) | C(M)^U(M)^a^t^a^c^t^a^t^g^t AAAAACAUAGUAAUAG5(L)^T (L)^t^a^g^c^a^c^t^g^g^c^5 (L)^T(L) | Bases 1-12: X Bases 13-16: L Bases 17-42: Y Bases 29-42: PTEN target |
| Example 11 (SEQ ID NO: 19) | 5(L)^T(L)^t^a^g^c^a^c^t^g^g^c^5 (L)^T(L)ACAUAGUAAUGAAAA t^c^a^t^t^a^c^t^a^t^G(M)^U(M) | Bases 1-14: PTEN target Bases 1-26: Y Bases 27-30: L Bases 31-42: X |

TABLE 5-continued

| | Sequence (left side: 5'-end, right side: 3'-end) | Remarks |
|---|---|---|
| Comparative Example 8 (SEQ ID NO: 20, 21) | A(M)^C(M)^AUAGUAAUAG5(L)^T (L)^t^a^g^c^a^c^t^g^g^c^5(L)^T (L) C(M)^U(M)^a^t^t^a^c^t^a^t^G(M)^U (M) | |
| Comparative Example 9 (SEQ ID NO: 22, 23) | 5(L)^T(L)^t^a^g^c^a^c^t^g^g^c^5 (L)^T(L)ACAUAGUAAU^G(M)^A(M) U(M)^C(M)^a^t^t^a^c^t^a^t^G(M)^U (M) | |
| Comparative Example 4 (SEQ ID NO: 8) | 5(L)^T(L)^t^a^g^c^a^c^t^g^g^c^5 (L)^T(L) | PTEN target |

Intramolecular hybridization in Examples 10 and 11 and intermolecular hybridization between two oligonucleotides in Comparative Examples 8 and 9 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 5

The final concentrations of each of the oligonucleotides of Table 5 were adjusted to 1 nM or 10 nM and the amount of PTEN mRNA relative to the amount of cyclophilin mRNA was evaluated as the expression level of PTEN using the same evaluation method as Evaluation Example 1. The results are shown in FIG. 22.

Figure 22:
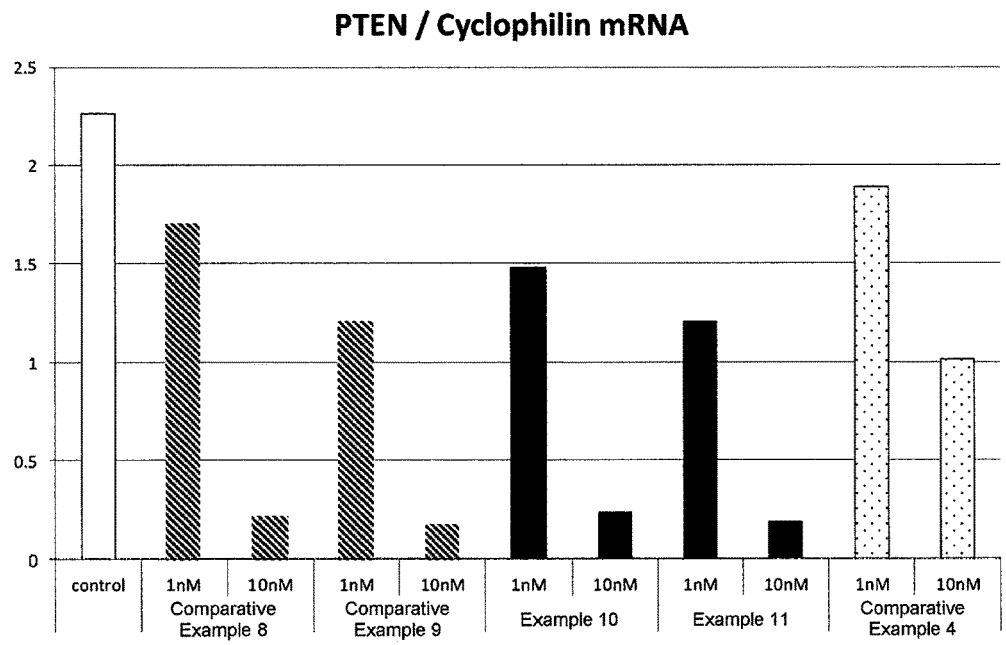
FIG. 22 is a graph indicating the effects of single-stranded oligonucleotides according to the present embodiment on the expression level of PTEN in mouse cerebral endothelial cells.

As is clear from FIG. 22, the single-stranded oligonucleotides according to the present invention (Examples 10 and 11) were confirmed to demonstrate a similar antisense effect in comparison with HCDO (Comparative Examples 8 and 9) and demonstrate a high antisense effect in comparison with ASO (Comparative Examples 4 and 7).

Evaluation Example 6

Figure 23:
FIG. 23 indicates the results of gel electrophoresis of single-stranded nucleotides according to the present embodiment before and after hybridization treatment.
Figure 24:
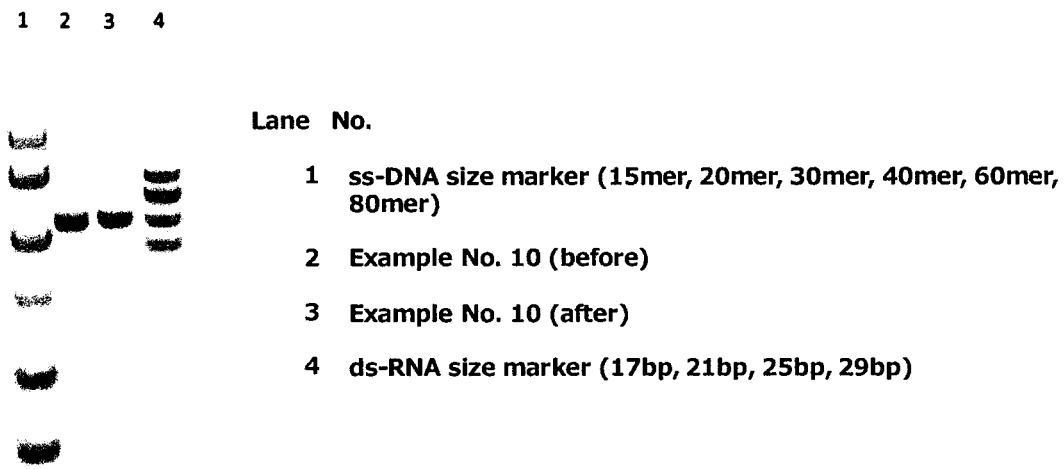
FIG. 24 indicates the results of gel electrophoresis of single-stranded nucleotides according to the present embodiment before and after hybridization treatment.

The results of non-denaturing polyacrylamide gel electrophoresis before and after the aforementioned intramolecular hybridization treatment in Examples 4 and 10 are shown in FIGS. 23 and 24. Single-stranded DNA size markers for electrophoresis, manufactured by GeneDesign Inc., were used as single-stranded DNA size markers. These include single-stranded DNA having 15, 20, 30, 40, 50, 60 and 80 as a number of nucleotides. Double-stranded RNA size markers for electrophoresis, manufactured by GeneDesign Inc., were used as double-stranded RNA size markers. These include double-stranded RNA having 17, 21, 25 and 29 as a number of base pairs. Furthermore, in FIGS. 23 and 24, "Lane No." indicates lane numbers in the aforementioned electrophoresis test, "Example No." indicates the example number, "before" indicates the results prior to the aforementioned hybridization treatment, "after" indicates the results after the aforementioned hybridization treatment, "ss-DNA size marker" indicates single-stranded DNA size markers, "ds-RNA size marker" indicates double-stranded RNA size markers, "mer" indicates the number of bases, and "bp" indicates the number of base pairs.

As is clear from FIGS. 23 and 24, single-stranded oligonucleotides according to the present invention were confirmed to have an intramolecular hybridization structure without going through a special hybridization step.

Examples 5 and 12 and Comparative Example 10

The oligonucleotides shown in Table 6 were prepared using the nS-8II Automated Nucleic Acid Synthesizer (GeneDesign). The target genes consisted of human Phosphatase and Tensin Homolog Deleted from Chromosome 10 (PTEN) and human apolipoprotein B (ApoB). Furthermore, the sequence notations in Table 6 are the same as those of Table 1.

TABLE 6

| | Sequence (left side: 5'-end, right side: 3'-end) | Remarks |
|---|---|---|
| Example 5 (SEQ ID NO: 10) | G(L)^5(L)^a^t^t^g^g^t^a^t^T(L)^5 (L)^A(L)AAAAUGAAUACCAUGC5 (L)^T(L)^t^a^g^c^a^c^t^g^g^c^5 (L)^T(L) | Bases 1-13: X ApoB target Bases 14-17: L Bases 18-44: Y Bases 31-44: PTEN target |

TABLE 6-continued

| | Sequence (left side: 5'-end, right side: 3'-end) | Remarks |
|---|---|---|
| Example 12 (SEQ ID NO: 24) | 5(L)^T(L)^t^a^g^c^a^c^t^g^g^c^5 (L)^T(L)AAAAAGGCCAGUGCUAAGG (L)^5(L)^a^t^t^g^g^t^a^t^T(L)^5 (L)^A(L) | Bases 1-14: X PTEN target Bases 15-18: L Bases 19-45: Y Bases 33-45: ApoB target |
| Comparative Example 10 (SEQ ID NO: 25, 26) | A(M)^G(M)^GCCAGUGCUAAGG(L)^5 (L)^a^t^t^g^g^t^a^t^T(L)^5(L)^A(L)5 (L)^T(L)^t^a^g^c^a^c^t^g^g^c^5 (L)^T(L) | |

Intramolecular hybridization in Examples 5 and 12 and intermolecular hybridization between two oligonucleotides in Comparative Example 10 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 7

The final concentrations of each of the oligonucleotides of Table 6 were adjusted to 1 nM or 10 nM and the amount of PTEN and ApoB mRNA relative to the amount of GAPDH mRNA was evaluated as the expression level of PTEN and ApoB, respectively, using the same evaluation method as Evaluation Example 2. Cells that did not undergo the transfection procedure were used as a control. The results are shown in FIGS. 25 and 26.

Figure 25:
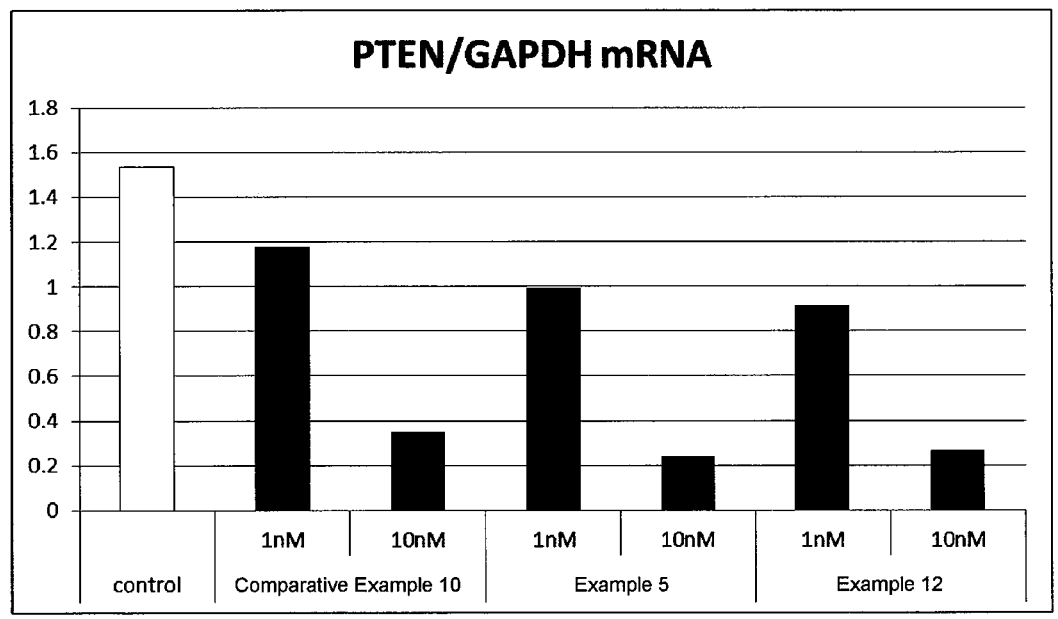
FIG. 25 is a graph indicating the effects of single-stranded oligonucleotides according to the present embodiment on the expression level of PTEN in human hepatoma-derived cells.
Figure 26:
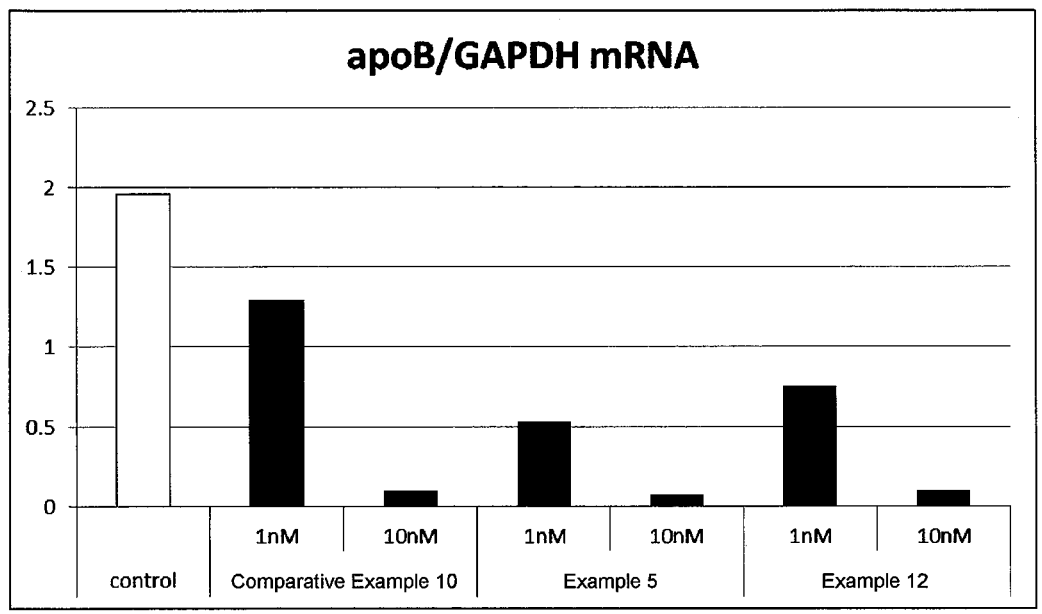
FIG. 26 is a graph indicating the effects of single-stranded oligonucleotides according to the present embodiment on the expression level of ApoB in human hepatoma-derived cells.

As is clear from FIGS. 25 and 26, the single-stranded oligonucleotides according to the present invention (Examples 5 and 12) were confirmed to demonstrate a high antisense effect in comparison with HDO (Comparative Example 10).

Examples 13 and 14 and Comparative Example 6

The oligonucleotides shown in Table 7 were prepared using the nS-8II Automated Nucleic Acid Synthesizer (GeneDesign). The target gene was human Phosphatase and Tensin Homolog Deleted from Chromosome 10 (PTEN). Furthermore, the sequence notations in Table 7 are the same as those of Table 1.

TABLE 7

| | Sequence (left side: 5'-end, right side: 3'-end) | Remarks |
|---|---|---|
| Example 13 (SEQ ID NO: 27) | 5(L)^T(L)^t^a^g^c^a^c^t^g^g^c^5 (L)^T(L)cta^t^t^a^c^t^a^t^g^tAA AAACAUAGUAAU^A(M)^G(M) | Bases 1-26: X Bases 1-14: PTEN target Bases 27-30: L Bases 31-42: Y |
| Example 14 (SEQ ID NO: 28) | C(M)^U(M)^a^t^t^a^c^UAUGUAAAA a^c^a^t^a^GUAAUAG5(L)^T (L)^t^a^g^c^a^c^t^g^g^c^5 (L)^T(L) | Bases 1-12: Y Bases 13-16: L Bases 17-42: Y Bases 29-42: PTEN target |
| Comparative Example 6 (SEQ ID NO: 12, 13) | U(M)^G(M)^A(M)^AUACCAAUGC5(L)^T (L)^t^a^g^c^a^c^t^g^g^c^5(L)^T(L) G(L)^5(L)^a^t^t^g^g^t^a^t^T(L)^5 (L)^A(L) | |

Intramolecular hybridization in Examples 13 and 14 and intermolecular hybridization between two oligonucleotides in Comparative Example 6 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 8

The final concentrations of each of the oligonucleotides of Table 7 were adjusted to 1 nM or 10 nM and the amount of PTEN mRNA relative to the amount of GAPDH mRNA was evaluated as the expression level of PTEN using the same evaluation method as Evaluation Example 2. Cells that did not undergo the transfection procedure were used as a control. The results are shown in FIG. 27.

Figure 27:
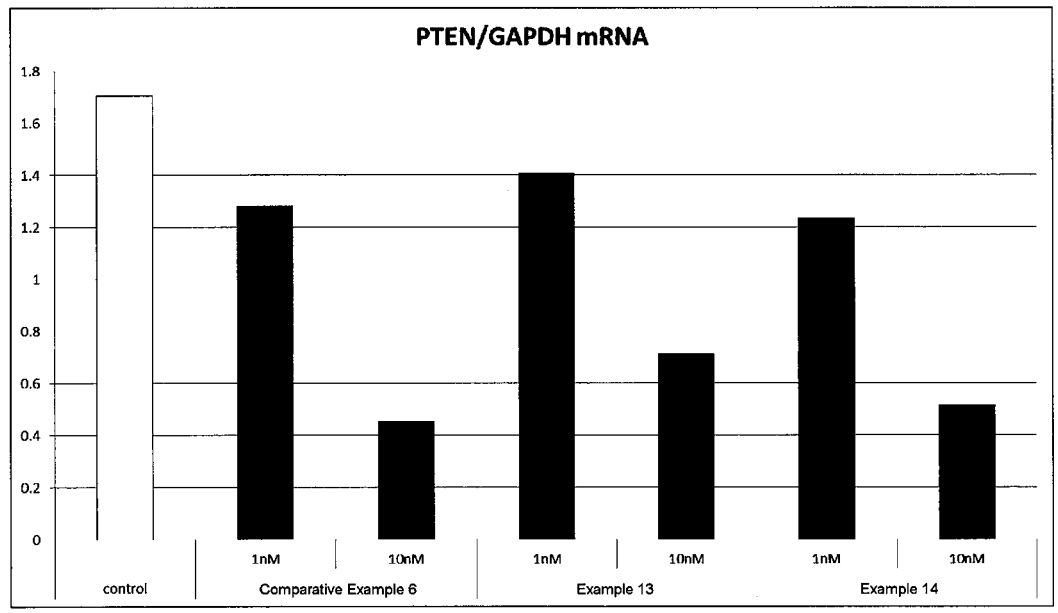
FIG. 27 is a graph indicating the effects of single-stranded oligonucleotides according to the present embodiment on the expression level of PTEN in human hepatoma-derived cells.

As is clear from FIG. 27, the single-stranded oligonucleotides according to the present invention (Examples 13 and 14) were confirmed to demonstrate antisense effect comparable to that of HDO (Comparative Example 6).

Example 15 and Comparative Example 11

The oligonucleotides shown in Table 8 were prepared using the nS-8II Automated Nucleic Acid Synthesizer (GeneDesign). The target gene was mouse apolipoprotein B (ApoB). Furthermore, "Toc-TEG-" in the sequence notations in Table 8 indicates that a moiety obtained by removing a hydrogen atom from the hydroxyl group of the tocopherol represented by the following formula (IV) is bound to a single oxygen atom of the phosphate group on the 5'-end through a group represented by the following formula (III-2):

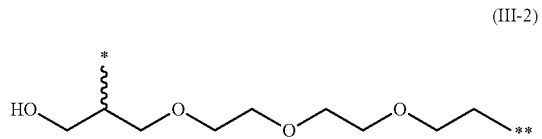

(III-2)

(wherein, one asterisk (*) represents a bonding site with the second oligonucleotide, while two asterisks (**) represent a bonding site with tocopherol).

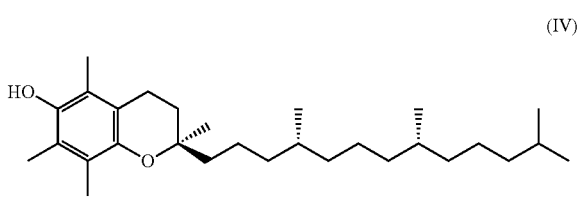 [SMILES: Cc1c(C)c2c(c(C)c1O)CC[C@@](C)(CCC[C@H](C)CCC[C@H](C)CCCC(C)C)O2]

(IV)

Other notations are the same as those of Table 1.

TABLE 8

| | Sequence (left side: 5'-end, right side: 3'-end) | Remarks |
|---|---|---|
| Example 15 (SEQ ID NO: 29) | Toc-TEG-U(M)^G(M)^A(M)^A UACCAAUGCAAAAG(L)^5 (L)^a^t^t^g^g^t^a^t^T(L)^5 (L)^A(L) | Bases 1-13: Y Bases 14-17: L Bases 18-30: X Functional molecule bound |
| Comparative Example 11 (SEQ ID NO: 30, 31) | G(L)^5(L)^a^t^t^g^g^t^a^t^T (L)^5(L)^A(L) Toc-TEG-U(M)^G(M)^A(M)^A UACCAAU^G(M)^C(M) | Functional molecule bound |

Intramolecular hybridization in Example 15 and intermolecular hybridization between two oligonucleotides in Comparative Example 11 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 9

Figure 28:
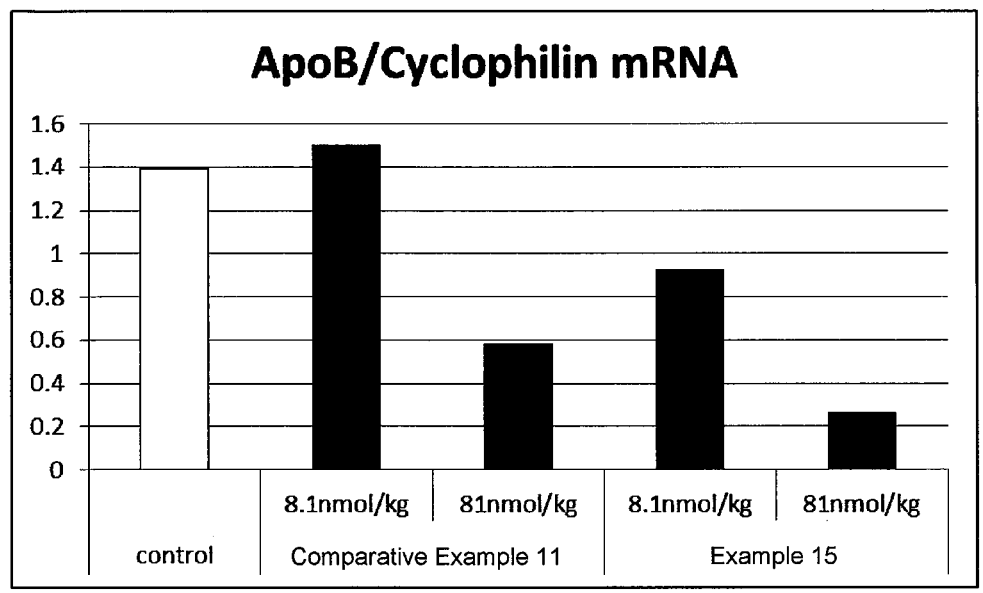
FIG. 28 is a graph indicating the effects of single-stranded oligonucleotides according to the present embodiment on the expression level of ApoB in mice.

Example 15 and Comparative Example 11 dissolved in physiological saline (Otsuka Normal Saline, Otsuka Pharmaceutical Factory) were intravenously administered to C57BL/6J mice (males, 5 weeks old, Japan Charles River) so that the dosage per mouse body weight was 8.1 nmol/kg or 81 nmol/kg as the amount of antisense oligonucleotide. Administration of physiological saline only (Otsuka Normal Saline, Otsuka Pharmaceutical Factory) was used as a control. After collecting blood from the orbital venous plexus 3 days after dosing, liver tissue was removed under isoflurane anesthesia. Extraction of RNA from the liver was carried out using the RNeasy Mini Kit (Qiagen) according to the recommended protocol of Qiagen. cDNA was obtained from total RNA using the PrimeScript RT Master Mix (Takara Bio). Real-time PCR was then carried out with the 7500 Real-Time PCR System (Applied Biosystems) using the resulting cDNA and TaqMan® Gene Expression ID (Applied Biosystems) to determine the amount of ApoB mRNA. During real-time PCR, the amount of mRNA of a housekeeping gene in the form of cyclophilin was simultaneously assayed, and the amount of ApoB mRNA relative to the amount of cyclophilin mRNA was evaluated as the expression level of ApoB. The results are shown in FIG. 28.

Furthermore, primers used are in the TaqMan Gene Expression Assays (Applied Biosystems) and the Assay ID were as indicated below.

Mouse ApoB assay: Mm1545150_m1

Mouse cyclophilin assay: Mm0234230_g1

Figure 29:
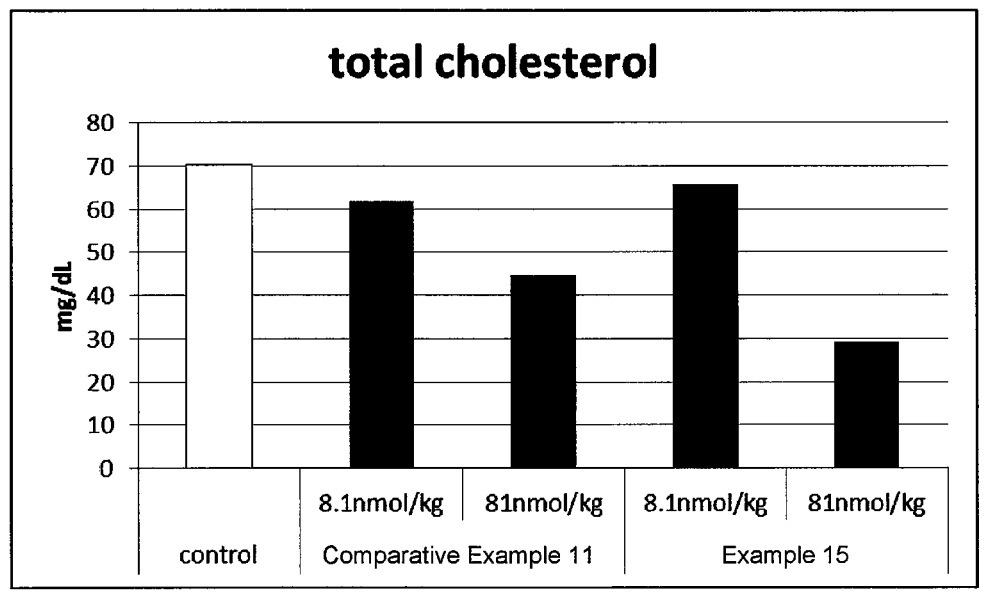
FIG. 29 is a graph indicating the effects of single-stranded oligonucleotides according to the present invention on plasma total cholesterol level in mice.

In addition, the collected blood was allowed to stand for 20 minutes at room temperature followed by separating the plasma by centrifuging for 15 minutes at 5000 rpm, 4° C. Total plasma cholesterol levels were measured for each of the plasma samples using Determiner L (Kyowa Medex). 240 μL of Reagent R-1 were added to 3.2 μL of plasma followed by heating for 5 minutes at 37° C. and then adding 80 μL of Reagent R-2 and heating for 5 minutes at 37° C. and measuring absorbance at 600 nm using a spectrophotometer. Values were then calculated using a calibration curve prepared using standard reagents. The results are shown in FIG. 29. Furthermore, in the figure, total cholesterol refers to the aforementioned total plasma cholesterol level.

As is clear from FIGS. 28 and 29, the single-stranded oligonucleotide according to the present invention (Example 15) was confirmed to demonstrate a high antisense effect in comparison with HDO (Comparative Example 11).

Examples 16, 17 and 18 and Comparative Examples 12 and 13

The oligonucleotides shown in Table 9 were prepared using the nS-8II Automated Nucleic Acid Synthesizer (GeneDesign). The target gene was miRNA-122. Furthermore, the sequence notations in Table 9 are the same as those of Table 1.

TABLE 9

|  | Sequence (left side: 5'-end, right side: 3'-end) | Remarks |
|---|---|---|
| Example 16 (SEQ ID NO: 32) | 5(L)^G(L)^a^t^t^g^g^t^a^t^c^g^c AAAAGCGAUACCAAUCG5 (L)^c^A(L)^t^t^G(L)^T(L)^c^a^5 (L)^a^5(L)^t^5(L)^5(L) | Bases 1-13: X<br>Bases 14-17: L<br>Bases 18-45: Y<br>Bases 31-45: miR-122 target |
| Example 17 (SEQ ID NO: 33) | 5(L)^c^A(L)^t^t^G(L)^T(L)^c ^a^5(L)^a^5(L)^t^5(L)^5(L) GCGAUACCAAUCGAAA A^c^g^a^t^t^g^g^t^a^t^5(L)^G (L)^5(L) | Bases 1-15: miR-122 target<br>Bases 1-28: Y<br>Bases 29-32: L<br>Bases 33-45: X |
| Example 18 (SEQ ID NO: 34) | A(M)^G(M)^GCCAGUGCUAAGAAAA5 (L)^T(L)^t^a^g^c^a^c^t^g^g^c^5(L)^T (L)AAAA5(L)^c^A(L)^t^t^G(L)^T (L)^c^a^5(L)^a^5(L)^t^5(L)^5(L) | Bases 1-14: Y<br>Bases 15-18: L<br>Bases 19-32: X<br>PTEN target<br>Bases 33-36: L'<br>Bases 37-51: X'<br>miR-122 target |
| Comparative Example 12 (SEQ ID NO: 35) | 5(L)^c^A(L)^t^t^G(L)^T (L)^c^a^5(L)^a^5(L)^t^5(L)^5(L) | |
| Comparative Example 13 (SEQ ID NO: 35, 37) | 5(L)^G(L)^a^t^t^g^g^t^a^t^5 (L)^G(L)^5(L) G(M)^C(M)^G(M)^AUACCAAU CG5(L)^c^A(L)^t^t^G(L)^T (L)^c^a^5(L)^a^5(L)^t^5(L)^5(L) | |

Intramolecular hybridization in Examples 16, 17 and 18 and intermolecular hybridization between two oligonucleotides in Comparative Example 13 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 10

Figure 30:
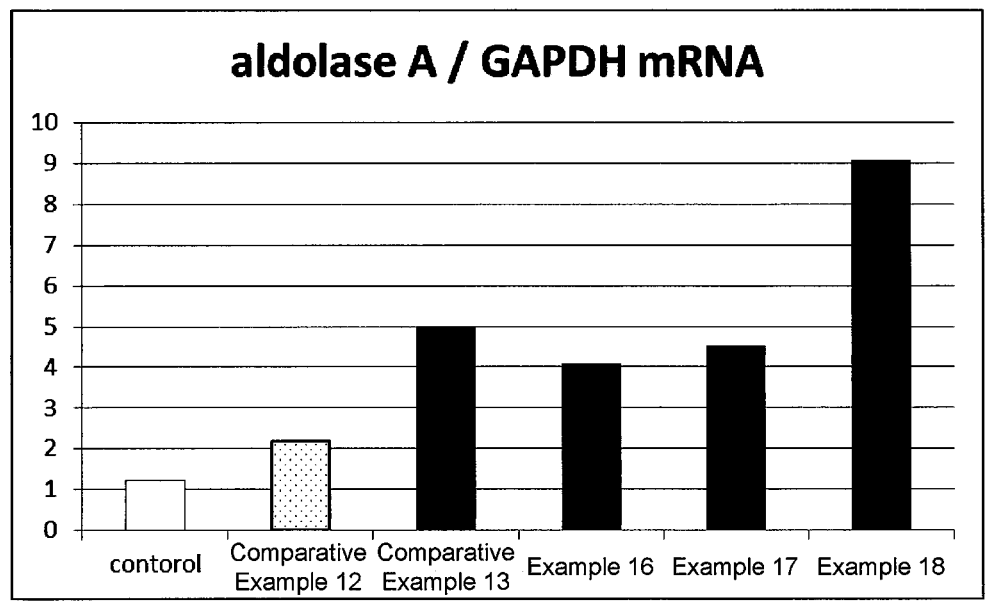
FIG. 30 is a graph indicating the effects of single-stranded oligonucleotides according to the present embodiment on the expression level of Aldolase A in human hepatoma-derived cells.

Human hepatoma cell line HuH-7 cells were disseminated in a 96-well plate at 2000 cells/well followed by culturing for 24 hours at 37° C. in 5% $CO_2$. Each of the oligonucleotides shown in Table 9 was added to each well to a final concentration of 0.4 nM using Lipofectamine® RNAiMax (Thermo Fisher Scientific) (transfection). The medium was replaced after 4 hours and the cells were recovered after 20 hours followed by extracting total RNA from the cells using the RNeasy Mini Kit (Qiagen).

cDNA was obtained from the total RNA using PrimeScript RT Master Mix (Takara Bio). Real-time PCR was then carried out with the 7500 Real-Time PCR System (Applied Biosystems) using the resulting cDNA and TaqMan® Gene Expression ID (Applied Biosystems) to determine the amount of Aldolase A mRNA which is the target gene of miRNA-122. During real-time PCR, the amount of mRNA of a housekeeping gene in the form of glyceraldehyde-3-phosphate dehydrogenase (GAPDH) was simultaneously assayed, and the amount of Aldolase A mRNA relative to the amount of GAPDH mRNA was evaluated as the expression level of Aldolase A. Cells that did not undergo the transfection procedure were used as a control. The results are shown in FIG. 30. At this time, a higher expression level of Aldolase A indicates a higher antisense effect.

Furthermore, primers used are in the TaqMan Gene Expression Assays (Applied Biosystems) and the Assay ID were as indicated below.

Human Aldolase A assay: Hs00605108_g1

Human GAPDH assay: Hs99999905_m1

As is clear from FIG. 30, single-stranded oligonucleotides according to the present invention (Examples 16 to 18) demonstrated a higher antisense effect than ASO (Comparative Example 12) and an antisense effect that was higher than or comparable to that of HDO (Comparative Example 13).

Example 15 and Comparative Examples 7 and 11

The oligonucleotides shown in Table 10 were prepared using the nS-8II Automated Nucleic Acid Synthesizer (GeneDesign). The target gene was mouse apolipoprotein B (ApoB). Furthermore, the sequence notations in Table 10 are the same as those of Tables 1 and 8.

TABLE 10

| | Sequence (left side: 5'-end, right side: 3'-end) | Remarks |
|---|---|---|
| Example 15 (SEQ ID NO: 29) | Toc-TEG-U(M)^G(M)^A (M)^AUACCAAUGCAAAAG (L)^5(L)^a^t^t^g^g^t^a^t^T (L)^5(L)^A(L) | Bases 1-13: Y Bases 14-17: L Bases 18-30: X Functional molecule bound |
| Comparative Example 11 (SEQ ID NO: 30, 31) | G(L)^5(L)^a^t^t^g^g^t^a^t^T (L)^5(L)^A(L) Toc-TEG-U(M)^G(M)^A (M)^AUACCAAU^G(M)^C(M) | Functional molecule bound |
| Comparative Example 7 (SEQ ID NO: 14) | G(L)^5(L)^a^t^t^g^g^t^a^t^T (L)^5(L)^A(L) | ApoB target |

Intramolecular hybridization in Example 15 and intermolecular hybridization between two oligonucleotides in Comparative Example 11 were carried out by heating for 5 minutes at 95° C. followed by allowing to stand for 1 hour at a constant temperature of 37° C. Hybridization was confirmed by non-denaturing polyacrylamide gel electrophoresis.

Evaluation Example 11

Figure 31:
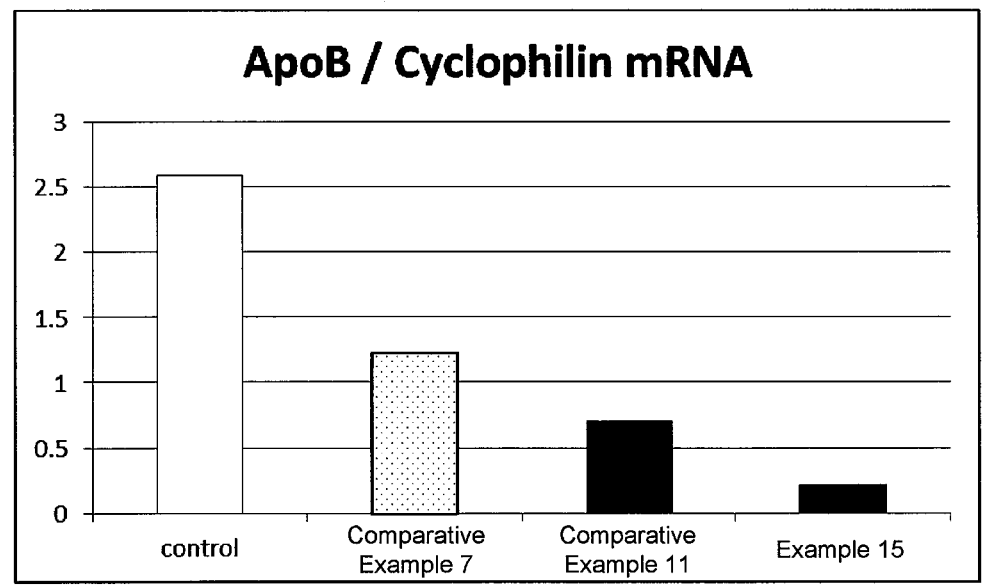
FIG. 31 is a graph indicating effects on the expression level of ApoB in the liver of C57BL/6J mice administered a single-stranded oligonucleotide according to the present embodiment.

Example 15, Comparative Example 11 and Comparative Example 7 dissolved in physiological saline (Otsuka Normal Saline, Otsuka Pharmaceutical Factory) were intravenously administered to C57BL/6J mice (males, 5 weeks old, Japan Charles River) so that the dosage per mouse body weight was 81 nmol/kg as the amount of antisense oligonucleotide. Administration of physiological saline only (Otsuka Normal Saline, Otsuka Pharmaceutical Factory) was used as a control. After collecting blood from the orbital venous plexus 3 days after dosing, liver tissue was removed under isoflurane anesthesia. Extraction of RNA from the liver was carried out using the RNeasy Mini Kit (Qiagen) according to the recommended protocol of Qiagen. cDNA was obtained from total RNA using the PrimeScript RT Master Mix (Takara Bio). Real-time PCR was then carried out with the 7500 Real-Time PCR System (Applied Biosystems) using the resulting cDNA and TaqMan® Gene Expression ID (Applied Biosystems) to determine the amount of ApoB mRNA. During real-time PCR, the amount of mRNA of a housekeeping gene in the form of cyclophilin was simultaneously assayed, and the amount of ApoB mRNA relative to the amount of cyclophilin mRNA was evaluated as the expression level of ApoB. The results are shown in FIG. 31.

Furthermore, primers used are in the TaqMan Gene Expression Assays (Applied Biosystems) and the Assay ID were as indicated below.

Mouse ApoB assay: Mm1545150_m1
Mouse cyclophilin assay: Mm0234230_g1

Figure 32:
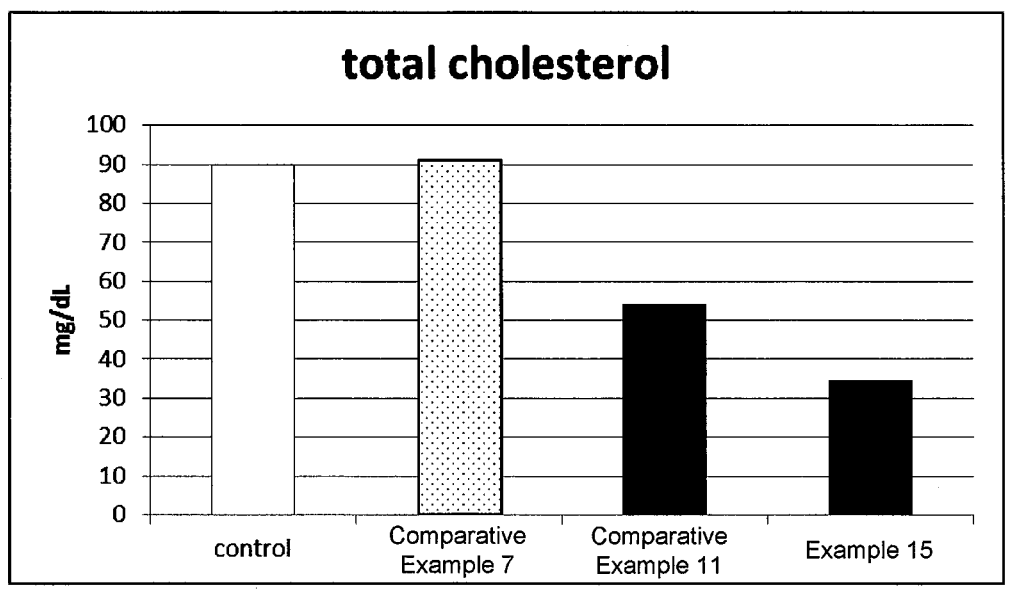
FIG. 32 is a graph indicating effects on plasma total cholesterol level in the liver of C57BL/6J mice administered a single-stranded oligonucleotide according to the present embodiment.

In addition, the collected blood was allowed to stand for 20 minutes at room temperature followed by separating the plasma by centrifuging for 15 minutes at 5000 rpm, 4° C. Total plasma cholesterol levels were measured for each of the plasma samples using Determiner L TC (Kyowa Medex). 240 μL of Reagent R-1 were added to 3.2 μL of plasma followed by heating for 5 minutes at 37° C. and then adding 80 μL of Reagent R-2 and heating for 5 minutes at 37° C. and measuring absorbance at 600 nm using a spectrophotometer. Values were then calculated using a calibration curve prepared using standard reagents. The results are shown in FIG. 32. Furthermore, in the figure, total cholesterol refers to the aforementioned total plasma cholesterol level.

As is clear from FIGS. 31 and 32, the single-stranded oligonucleotide according to the present invention (Example 15) was confirmed to demonstrate a high antisense effect in comparison with HDO (Comparative Example 11) and ASO (Comparative Example 7).

Evaluation Example 12

Figure 33:
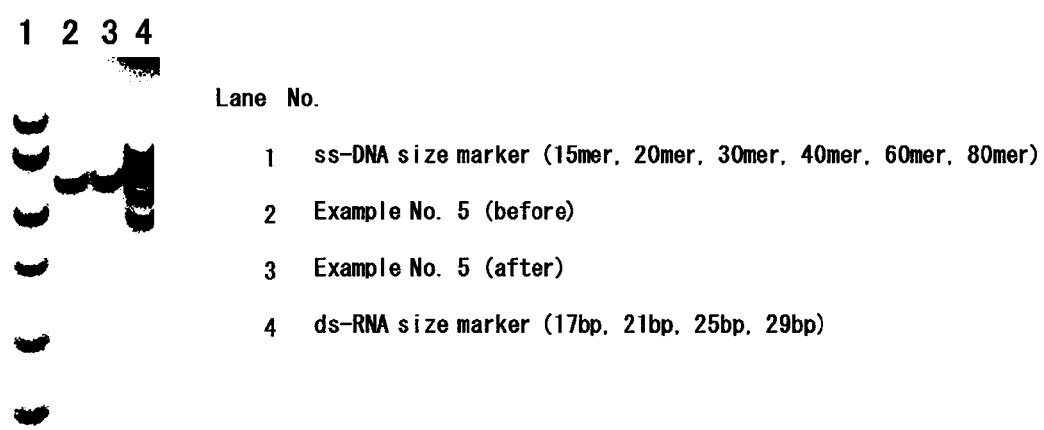
FIG. 33 indicates the results of gel electrophoresis of single-stranded oligonucleotides according to the present embodiment before and after hybridization treatment.

The results of non-denaturing polyacrylamide gel electrophoresis before and after the aforementioned intramolecular hybridization treatment in Example 5 are shown in FIG. 33. Single-stranded DNA size markers for electrophoresis, manufactured by GeneDesign Inc., were used as single-stranded DNA size markers. These include single-stranded DNA having 15, 20, 30, 40, 50, 60 and 80 as a number of nucleotides. Double-stranded RNA size markers for electrophoresis, manufactured by GeneDesign Inc., were used as double-stranded RNA size markers. These include double-stranded RNA having 17, 21, 25 and 29 as a number of base pairs. Furthermore, the notations used in FIG. 33 are the same as those used in FIGS. 23 and 24.

As is clear from FIG. 33, single-stranded oligonucleotides according to the present invention were confirmed to have an intramolecular hybridization structure without going through a special hybridization step.

INDUSTRIAL APPLICABILITY

In several embodiments thereof, use of the single-stranded oligonucleotide of the present invention makes it possible to efficiently deliver an antisense nucleic acid to a specific organ (or cell) with high specificity, effectively control the function of a target RNA with that nucleic acid, and/or effectively inhibit expression of a target gene. In addition, since the single-stranded oligonucleotide in several embodiments thereof is able to apply various molecules such as lipids (such as tocopherol or cholesterol), sugars (such as glucose or sucrose), protein, peptides or antibodies as functional molecules for delivering to a specific organ, the single-stranded oligonucleotide in several embodiments thereof is able to target various organs, tissues and cells. Moreover, since the antisense effect thereof does not decrease even if the single-stranded oligonucleotide in several embodiments thereof is modified in order to impart resistance to RNase and the like, the single-stranded oligonucleotide in several embodiments thereof can also be used in an aspects of enteral administration.

Thus, the single-stranded oligonucleotide in several embodiments thereof allows the obtaining of high pharmacological efficacy by administering at a low concentration, and since it is also superior in terms of reducing adverse side effects as a result of suppressing distribution in organs other than the target of the antisense nucleic acid, the single-stranded oligonucleotide is useful as a pharmaceutical composition and the like for treating and preventing diseases associated with function of a target RNA and/or overexpression of a target gene, such as metabolic diseases, tumors or infections.

The disclosures of Japanese Patent Application No. 2016-012804 (filing date: Jan. 26, 2016) and Japanese Patent Application No. 2016-158833 (filing date: Aug. 12, 2016) are incorporated in the present description in their entirety by reference. All documents, patent applications and technical standards described in the present description are incorporated in the present description by reference to the same degree as the case in which the incorporation of each document, patent application and technical standard by reference is specifically and individually described.

The invention claimed is:

1. A single-stranded oligonucleotide represented by the formula:

X-L-Y wherein

X represents a group derived from a first oligonucleotide composed of 8 to 100 nucleotides that are independently selected from a deoxyribonucleotide, ribonucleotide and sugar-modified nucleotide and that contains at least one sugar-modified nucleotide, Y represents a group derived from a second oligonucleotide composed of 8 to 100 nucleotides that are independently selected from a deoxyribonucleotide, ribonucleotide and sugar-modified nucleotide, and L represents a group derived from a third oligonucleotide that respectively covalently bonds with the first oligonucleotide and the second oligonucleotide at both ends thereof and is degraded under physiological conditions; wherein, the first oligonucleotide has a nucleotide sequence X, and the second oligonucleotide has a nucleotide sequence Y, the nucleotide sequence X contains a first nucleotide sequence that is capable of hybridizing with at least a portion of the second oligonucleotide and contains at least four contiguous nucleotides recognized by RNase H, the nucleotide sequence Y contains a second nucleotide sequence that is capable of hybridizing with at least a portion of the first oligonucleotide and contains at least one ribonucleotide, the nucleotide sequence X contains at least one antisense sequence capable of hybridizing with a target RNA and the first nucleotide sequence is the antisense sequence, and in the case of having two or more antisense sequences, the target RNA hybridized by each antisense sequence may be the same or different, wherein X and Y hybridize by the first nucleotide sequence portion and the second nucleotide sequence portion.

2. The single-stranded oligonucleotide according to claim 1, wherein X bonds to L on the 3'-side and Y bonds to L on the 5'-side.

3. The single-stranded oligonucleotide according to claim 1, wherein X bonds to L on the 5'-side and Y bonds to L on the 3'-side.

4. The single-stranded oligonucleotide according to claim 1, wherein nucleotides contained in the third oligonucleotide are mutually coupled through phosphodiester bonds.

5. The single-stranded oligonucleotide according to claim 1, wherein the third oligonucleotide is DNA or RNA.

6. The single-stranded oligonucleotide according to claim 1, wherein the first oligonucleotide contains a sugar-modified nucleotide bound adjacent to at least one of the 5'-side and 3'-side of the first nucleotide sequence portion.

7. The single-stranded oligonucleotide according to claim 1, wherein the first oligonucleotide contains a sugar-modified nucleotide bound adjacent to the 5'-side and 3'-side of the first nucleotide sequence portion.

8. The single-stranded oligonucleotide according to claim 1, wherein the first oligonucleotide contains a phosphorothioate bond.

9. The single-stranded oligonucleotide according to claim 1, wherein the first nucleotide sequence is composed of 4 to 20 nucleotides including at least one deoxyribonucleotide.

10. The single-stranded oligonucleotide according to claim 1, wherein the second nucleotide sequence is a sequence that contains at least four contiguous nucleotides cleaved by RNase H.

11. The single-stranded oligonucleotide according to claim 10, wherein the second oligonucleotide contains a sugar-modified nucleotide bound adjacent to at least one of the 5'-side and 3'-side of the second nucleotide sequence portion.

12. The single-stranded oligonucleotide according to claim 11, wherein at least one of the 5'-side and 3'-side of the second nucleotide sequence portion is coupled to an adjacent nucleotide through a phosphorothioate bond.

13. The single-stranded oligonucleotide according to claim 1, wherein the nucleotide sequence Y contains at least one antisense sequence.

14. The single-stranded oligonucleotide according to claim 13, wherein the Y has the second nucleotide sequence portion between the antisense sequence portion and L.

15. The single-stranded oligonucleotide according to claim 14, wherein the antisense sequence contained by the nucleotide sequence Y is a sequence that contains at least four contiguous nucleotides recognized by RNase H when hybridizing with a target RNA.

16. The single-stranded oligonucleotide according to claim 14, wherein the antisense sequence portion contained by the Y contains at least one sugar-modified nucleotide but does not contain an oligonucleotide strand composed of four contiguous deoxyribonucleotides.

17. The single-stranded oligonucleotide according to claim 16, wherein the nucleotide sequence X contains a sequence that is able to hybridize with at least a portion of the antisense sequence portion contained by the Y and contains at least four contiguous nucleotides cleaved by RNase H.

18. The single-stranded oligonucleotide according to claim 1, wherein X contains the 5'-end or 3'-end.

19. The single-stranded oligonucleotide according to claim 1, further containing a group represented by the formula:

X'-L'- wherein

X' is a group derived from a fourth oligonucleotide composed of 8 to 100 nucleotides that are independently selected from a deoxyribonucleotide, ribonucleotide and sugar-modified nucleotide and that contains at least one nucleotide of which at least one of the sugar moiety, base moiety and phosphate moiety has been modified, and L' represents a group derived from a fifth oligonucleotide that respectively covalently bonds with the first oligonucleotide and the fourth oligonucleotide at both ends thereof and is degraded under physiological conditions; wherein, the fourth oligonucleotide has an antisense sequence capable of hybridizing with a target RNA.

20. The single-stranded oligonucleotide according to claim 19, wherein X' contains at least one sugar-modified nucleotide, and the antisense sequence possessed by the fourth oligonucleotide contains at least four contiguous nucleotides recognized by RNase H when hybridizing with a target RNA.

21. The single-stranded oligonucleotide according to claim 19, wherein the antisense sequence portion contained by the fourth oligonucleotide contains at least one sugar-modified nucleotide, but does not contain an oligonucleotide strand composed of four contiguous deoxyribonucleotides.

22. The single-stranded oligonucleotide according to claim 21, wherein the antisense sequence portion contained by the fourth oligonucleotide hybridizes with at least a portion of the second oligonucleotide.

23. The single-stranded oligonucleotide according to claim 20, wherein nucleotides contained in the fifth oligonucleotide are mutually coupled through phosphodiester bonds.

24. The single-stranded oligonucleotide according to claim 20, wherein the fifth oligonucleotide is DNA or RNA.

25. The single-stranded oligonucleotide according to claim 1, containing a sugar-modified nucleotide bound adjacent to at least one of the 5'-side and 3'-side of the antisense sequence portion.

26. The single-stranded oligonucleotide according to claim 1, containing sugar-modified nucleotides bound adjacent to the 5'-side and 3'-side of the antisense sequence portion.

27. The single-stranded oligonucleotide according to claim 1, wherein the antisense sequence is composed of 4 to 20 nucleotides including at least one deoxyribonucleotide.

28. The single-stranded oligonucleotide according to claim 1, wherein the antisense sequence portion contains a phosphorothioate bond.

29. The single-stranded oligonucleotide according to claim 1, wherein Y contains the 5'-end or 3'-end.

30. The single-stranded oligonucleotide according to claim 1, further containing a group derived from a functional molecule having at least one function selected from the group consisting of a labeling function, a purifying function and a target site delivery function.

31. The single-stranded oligonucleotide according to claim 30, wherein the functional molecule is selected from the group consisting of sugars, lipids, peptides, proteins and derivatives thereof.

32. The single-stranded oligonucleotide according to claim 31, wherein the functional molecule is a lipid selected from the group consisting of cholesterol, tocopherol and tocotrienol.

33. The single-stranded oligonucleotide according to claim 31, wherein the functional molecule is a sugar derivative that interacts with an asialoglycoprotein receptor.

34. The single-stranded oligonucleotide according to claim 31, wherein the functional molecule is a peptide or protein selected from the group consisting of receptor ligands and antibodies.

35. A pharmaceutical composition containing the single-stranded oligonucleotide according to claim 1 and a pharmacologically acceptable carrier.

36. A method for controlling the function of a target RNA which hybridizes with a single-stranded oligonucleotide according to claim 1, comprising a step for contacting the single-stranded oligonucleotide with a cell, wherein a portion of the target RNA hybridizes with an antisense sequence portion of the single-stranded oligonucleotide as a result of the contacting.

37. A method for controlling the function of a target RNA which hybridizes with a single-stranded oligonucleotide according to claim 1 in a mammal, comprising a step for administering a pharmaceutical composition containing the single-stranded oligonucleotide to the mammal, wherein a portion of the target RNA hybridizes with an antisense sequence portion of the single-stranded oligonucleotide as a result of the administering.

38. A method for producing the single-stranded oligonucleotide according to claim 1, comprising a step for elongating the nucleotide strand at the 3'-end or 5'-end of an oligonucleotide containing at least one of X, L and Y.

39. The single-stranded oligonucleotide according to claim 1, wherein the sugar-modified nucleotide is at least one selected from the group consisting of hexitol nucleotides, cyclohexene nucleotides, peptide nucleic acids, glycol nucleic acids, threose nucleotides, morpholine nucleic acids, tricyclo-DNA, 2'-O-methyl nucleotides, 2'-O-methoxyethyl nucleotides, 2'-O-aminopropyl nucleotide, 2'-fluoronucleotide, 2'-F-arabinonucleotides, bridged nucleotides and 2'-O-methylcarbamoylethyl nucleotides.

40. The single-stranded oligonucleotide according to claim 1, wherein the partial structure represented by formula X— is represented by (a) the formula $X^1$—$X^2$—$X^3$— wherein $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^2$ represents a first nucleotide sequence portion, and the first nucleotide sequence is an antisense sequence that is a sequence containing at least four contiguous nucleotides recognized by RNase H when hybridizing with a target RNA, and $X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide, (b) the formula $X_Z^1$-$X_Z^2$-$X_Z^3$-$X^0$—$X^2$— wherein $X_Z^1$ represents a group derived from an oligonucleotide that is composed of 1 to 10 nucleotides independently selected from deoxyribonucleotides, ribonucleotides and sugar-modified nucleotides, and includes at least one sugar-modified nucleotide, $X_Z^2$ represents an antisense sequence portion contained by X, $X_Z^3$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^0$ represents a group derived from an oligonucleotide composed of 2 to 7 nucleotides independently selected from deoxyribonucleotides and ribonucleotides, and $X^2$ represents a first nucleotide sequence portion that covalently bonds with a third oligonucleotide, (c) the formula $X_Z$—$X^0$—$X^2$— wherein $X_Z$ represents an antisense sequence portion that contains at least one sugar-modified nucleotide but does not contain an oligonucleotide strand composed of four contiguous deoxyribonucleotides, $X^0$ represents a group derived from an oligonucleotide composed of 2 to 7 nucleotides independently selected from deoxyribonucleotides and ribonucleotides, and $X^2$ represents a first nucleotide sequence portion that covalently bonds with a third oligonucleotide, (d) the formula $X^1$—$X^2$— wherein $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, and $X^2$ represents a first nucleotide sequence portion that covalently bonds with a third oligonucleotide, or (e) the formula $X^4$—$X^5$—$X^1$—$X^2$—$X^3$— wherein $X^4$ represents a group derived from an oligonucleotide that is composed of 1 to 10 nucleotides independently selected from deoxyribonucleotides, ribonucleotides and sugar-modified nucleotides, and includes at least one sugar-modified nucleotide, $X^5$ represents a group derived from an oligonucleotide that is composed of 4 to 20 nucleotides independently selected from deoxyribonucleotides, ribonucleotides and sugar-modified nucleotides and includes at least one ribonucleotide, $X^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X^2$ represents a first nucleotide sequence portion, and the first nucleotide sequence is an antisense sequence that is a sequence containing at least four contiguous nucleotides recognized by RNase H when hybridizing with a target RNA, and $X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide.

41. The single-stranded oligonucleotide according to claim 1, wherein the partial structure represented by formula —Y is represented by
(a) the formula —$Y^2$-$Y^1$ wherein
$Y^2$ represents a group derived from an oligonucleotide that is a second nucleotide sequence portion composed of 4 to 20 nucleotides independently selected from deoxyribonucleotides, ribonucleotides and sugar-modified nucleotides and includes at least one ribonucleotide, and the oligonucleotide covalently bonds with a third oligonucleotide, and
$Y^1$ represents a group derived from an oligonucleotide that is composed of 1 to 10 nucleotides independently selected from deoxyribonucleotides, ribonucleotides and sugar-modified nucleotides and includes at least one sugar-modified nucleotide,
(b) the formula —$Y^2$-$Y^1$ wherein
$Y^2$ represents a group derived from an oligonucleotide that contains a second nucleotide sequence portion, is composed of 4 to 40 nucleotides independently selected from deoxyribonucleotides, ribonucleotides and sugar-modified nucleotides and includes at least one ribonucleotide, and the oligonucleotide covalently bonds with a third oligonucleotide, and
$Y^1$ represents a group derived from an oligonucleotide that is composed of 1 to 10 nucleotides independently selected from deoxyribonucleotides, ribonucleotides and sugar-modified nucleotides and includes at least one sugar-modified nucleotide,
(c) the formula —$Y^0$-$Y_Z^3$—$Y_Z^2$—$Y_Z^1$ wherein
$Y^0$ represents a second nucleotide sequence portion that covalently bonds with a third oligonucleotide,
$Y_Z^3$ represents a group derived from an oligonucleotide that is composed of 1 to 10 nucleotides independently selected from deoxyribonucleotides, ribonucleotides and sugar-modified nucleotides and includes at least one sugar-modified nucleotide,
$Y_Z^2$ represents an antisense sequence portion contained by Y, and
$Y_Z^1$ represents a group derived from an oligonucleotide that is composed of 1 to 10 nucleotides independently selected from deoxyribonucleotides, ribonucleotides and sugar-modified nucleotides and includes at least one sugar-modified nucleotide, or
(d) the formula —$Y^0$-$Y_Z$ wherein
$Y^0$ represents a second nucleotide sequence portion that covalently bonds with a third oligonucleotide, and
$Y_Z$ represents an antisense sequence portion that contains at least one sugar-modified nucleotide but does not contain an oligonucleotide strand composed of four contiguous deoxyribonucleotides.

42. The single-stranded oligonucleotide according to claim 1, wherein the third oligonucleotide is composed of 3 to 10 nucleotides independently selected from the group consisting of deoxyribonucleotides and ribonucleotides.

43. The single-stranded oligonucleotide according to claim 20 containing a partial structure represented by the formula X'-L'-X—, and the partial structure is represented by
(a) the formula $X'^1$—$X'^2$—$X'^3$-L'-$X^1$—$X^2$—$X^3$— wherein
$X'^1$ represents a group derived from an oligonucleotide that is composed of 1 to 10 nucleotides independently selected from deoxyribonucleotides, ribonucleotides and sugar-modified nucleotides and includes at least one sugar-modified nucleotide,
$X'^2$ represents an antisense sequence portion contained by X',
$X'^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a fifth oligonucleotide,
L' represents a group derived from an oligonucleotide composed of 2 to 7 nucleotides independently selected from deoxyribonucleotides and ribonucleotides,
$X^1$ represents a group derived from an oligonucleotide that is composed of 1 to 10 nucleotides independently selected from deoxyribonucleotides, ribonucleotides and sugar-modified nucleotides and includes at least one sugar-modified nucleotide,
$X^2$ represents a first nucleotide sequence portion, and the first nucleotide sequence is an antisense sequence that is a sequence containing at least four contiguous nucleotides recognized by RNase H when hybridizing with a target RNA, and
$X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide, or
(b) the formula $X'_Z$-L'-$X^1$—$X^2$—$X^3$— wherein
$X'_Z$ represents an antisense sequence portion that contains at least one sugar-modified nucleotide but does not contain an oligonucleotide strand composed of four contiguous nucleotides, and covalently binds with a fifth nucleotide,
L' represents a group derived from an oligonucleotide composed of 2 to 7 nucleotides independently selected from deoxyribonucleotides and ribonucleotides,
$X^1$ represents a group derived from an oligonucleotide that is composed of 1 to 10 nucleotides independently selected from deoxyribonucleotides, ribonucleotides and sugar-modified nucleotides and includes at least one sugar-modified nucleotide,
$X^2$ represents a first nucleotide sequence portion, and the first nucleotide sequence is an antisense sequence that is a sequence containing at least four contiguous nucleotides recognized by RNase H when hybridizing with a target RNA, and
$X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with a third oligonucleotide.

44. A method for controlling expression of a target gene corresponding to a target RNA which hybridizes with a single-stranded oligonucleotide according to claim 1, including a step for contacting the single-stranded oligonucleotide with a cell, wherein a portion of the target RNA hybridizes with an antisense sequence portion of the single-stranded oligonucleotide as a result of the contacting.

45. A method for controlling expression of a target gene corresponding to a target RNA which hybridizes with a single-stranded oligonucleotide according to claim 1 in a mammal, including a step for administering a pharmaceutical composition containing the single-stranded oligonucleotide to the mammal, wherein a portion of the target RNA hybridizes with an antisense sequence portion of the single-stranded oligonucleotide as a result of the administering.

* * * * *

UNITED STATES PATENT AND TRADEMARK OFFICE
CERTIFICATE OF CORRECTION

| | | |
|---|---|---|
| PATENT NO. | : 11,530,409 B2 | Page 1 of 1 |
| APPLICATION NO. | : 16/073114 | |
| DATED | : December 20, 2022 | |
| INVENTOR(S) | : Iriyama et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 89 days.

Signed and Sealed this
Thirty-first Day of December, 2024

Derrick Brent
*Acting Director of the United States Patent and Trademark Office*